(12) United States Patent
Knight et al.

(10) Patent No.: US 9,046,507 B2
(45) Date of Patent: Jun. 2, 2015

(54) METHOD, SYSTEM AND APPARATUS FOR INCORPORATING CAPACITIVE PROXIMITY SENSING IN AN AUTOMATED FLUID TRANSFER PROCEDURE

(75) Inventors: Byron J. Knight, San Diego, CA (US); David Opalsky, San Diego, CA (US); Brian Schroeter, San Diego, CA (US)

(73) Assignee: GEN-PROBE INCORPORATED, San Diego, CA (US)

( * ) Notice: Subject to any disclaimer, the term of this patent is extended or adjusted under 35 U.S.C. 154(b) by 636 days.

(21) Appl. No.: 13/192,828

(22) Filed: Jul. 28, 2011

(65) Prior Publication Data

US 2012/0024055 A1    Feb. 2, 2012

Related U.S. Application Data

(60) Provisional application No. 61/368,759, filed on Jul. 29, 2010, provisional application No. 61/423,254, filed on Dec. 15, 2010.

(51) Int. Cl.
*G01F 23/26* (2006.01)
*G01N 35/10* (2006.01)

(52) U.S. Cl.
CPC .......... *G01N 35/1011* (2013.01); *G01F 23/263* (2013.01); *G01N 2035/1013* (2013.01)

(58) Field of Classification Search
CPC ..... G01F 23/263; G01F 23/268; G01F 23/00; G01F 23/266; G01F 23/26; C12Q 1/6865; C12Q 1/6848; A61B 5/0452; A61B 5/0205; G01N 2035/1025; B01L 3/0275; B01L 2200/025; C12M 41/46

USPC .............................................. 73/304 C, 290 R
See application file for complete search history.

(56) References Cited

U.S. PATENT DOCUMENTS

| | | |
|---|---|---|
| 749,104 A | 1/1904 | Schoenefeldt |
| 1,010,016 A | 11/1911 | Campau |
| 2,313,045 A | 3/1943 | Brown |
| 3,504,376 A | 3/1970 | Bendnar et al. |
| 3,562,962 A | 2/1971 | Ohno |

(Continued)

FOREIGN PATENT DOCUMENTS

| | | |
|---|---|---|
| DE | 4128698 A1 | 3/1993 |
| DE | 9405224.7 | 5/1994 |

(Continued)

OTHER PUBLICATIONS

International Preliminary Examination Report issued in PCT/US2011/045890, 7 pages (Jan. 29, 2013).

(Continued)

*Primary Examiner* — Peter Macchiarolo
*Assistant Examiner* — Mohammed Karamet-Amircola
(74) *Attorney, Agent, or Firm* — Rothwell, Figg, Ernst & Manbeck PC

(57) ABSTRACT

A fluid transfer apparatus includes a fluid transfer probe, a fluid level detection system, and a tip detection system. The fluid level detection system is configured to detect contact by the fluid transfer probe with a fluid surface within a receptacle from a signal based on the capacitance of the fluid transfer probe. The tip detection system is configured to detect the presence or absence of a tip at a distal end of the fluid transfer probe from a signal based on the capacitance of the fluid transfer probe.

47 Claims, 25 Drawing Sheets

(56) References Cited

U.S. PATENT DOCUMENTS

| | | |
|---|---|---|
| 3,565,582 A | 2/1971 | Young |
| 3,626,190 A | 12/1971 | Cannon |
| 3,644,095 A | 2/1972 | Netheler et al. |
| 3,663,816 A | 5/1972 | Scherzer et al. |
| 3,676,076 A | 7/1972 | Grady |
| 3,754,444 A | 8/1973 | Ure et al. |
| 3,883,305 A | 5/1975 | Hoskins et al. |
| 3,985,649 A | 10/1976 | Eddelman |
| 4,039,288 A | 8/1977 | Moran |
| 4,054,415 A | 10/1977 | Seligson et al. |
| 4,169,125 A | 9/1979 | Rodriguez et al. |
| 4,170,625 A | 10/1979 | Welch |
| 4,234,539 A | 11/1980 | Ginsberg et al. |
| 4,235,840 A | 11/1980 | Mendoza et al. |
| 4,268,477 A | 5/1981 | Herzstark |
| 4,276,051 A | 6/1981 | Ginsberg et al. |
| 4,291,230 A | 9/1981 | Heiss |
| 4,298,571 A | 11/1981 | DiFulvio et al. |
| 4,305,668 A | 12/1981 | Bilbrey |
| 4,313,735 A | 2/1982 | Yamashita et al. |
| 4,315,891 A | 2/1982 | Sakurada |
| 4,344,768 A | 8/1982 | Parker et al. |
| 4,346,056 A | 8/1982 | Sakurada |
| RE31,108 E | 12/1982 | Ginsberg et al. |
| 4,366,119 A | 12/1982 | Takeuchi |
| RE31,150 E | 2/1983 | Ginsberg et al. |
| 4,408,492 A * | 10/1983 | Kossoff et al. .................. 73/631 |
| 4,451,433 A | 5/1984 | Yamashita et al. |
| 4,459,265 A | 7/1984 | Berglund |
| 4,478,095 A | 10/1984 | Bradley et al. |
| 4,479,720 A | 10/1984 | Mochida et al. |
| 4,483,823 A | 11/1984 | Umetsu et al. |
| 4,483,927 A | 11/1984 | Takekawa |
| 4,497,774 A | 2/1985 | Scordato |
| 4,501,164 A | 2/1985 | Stockdale et al. |
| 4,528,159 A | 7/1985 | Liston |
| 4,595,562 A | 6/1986 | Liston et al. |
| 4,612,289 A | 9/1986 | Furuta et al. |
| 4,647,199 A | 3/1987 | Ferber et al. |
| 4,647,432 A | 3/1987 | Wakatake |
| 4,678,752 A | 7/1987 | Thorne et al. |
| 4,683,195 A | 7/1987 | Mullis et al. |
| 4,683,202 A | 7/1987 | Mullis |
| 4,695,430 A | 9/1987 | Coville et al. |
| 4,699,766 A | 10/1987 | Yamashita |
| 4,699,767 A | 10/1987 | Aihara |
| 4,731,225 A | 3/1988 | Wakatake |
| 4,747,693 A | 5/1988 | Kahl |
| 4,755,055 A | 7/1988 | Johnson et al. |
| 4,761,268 A | 8/1988 | Anderson et al. |
| 4,764,342 A | 8/1988 | Kelln et al. |
| 4,774,055 A | 9/1988 | Wakatake et al. |
| 4,781,891 A | 11/1988 | Galle et al. |
| 4,818,492 A | 4/1989 | Shimizu |
| 4,826,660 A | 5/1989 | Smith et al. |
| 4,834,944 A | 5/1989 | Wakatake |
| 4,844,868 A | 7/1989 | Rokugawa |
| 4,848,917 A | 7/1989 | Benin et al. |
| 4,849,176 A | 7/1989 | Sakagami |
| 4,855,110 A | 8/1989 | Marker et al. |
| 4,863,690 A | 9/1989 | Berthold et al. |
| 4,865,986 A | 9/1989 | Coy et al. |
| 4,871,676 A | 10/1989 | Yamada |
| 4,883,644 A | 11/1989 | Perlman |
| 4,895,650 A | 1/1990 | Wang |
| 4,906,433 A | 3/1990 | Minekane |
| 4,908,186 A | 3/1990 | Sakamaki |
| 4,908,320 A | 3/1990 | Zakowski et al. |
| 4,919,887 A | 4/1990 | Wakatake |
| 4,961,906 A | 10/1990 | Anderson et al. |
| 4,965,049 A | 10/1990 | Lillig et al. |
| 4,981,801 A | 1/1991 | Suzuki et al. |
| 5,043,141 A | 8/1991 | Wilson et al. |
| 5,051,238 A | 9/1991 | Umetsu et al. |
| 5,075,079 A | 12/1991 | Kerr et al. |
| 5,082,628 A | 1/1992 | Andreotti et al. |
| 5,084,242 A | 1/1992 | Sakuma et al. |
| 5,086,233 A | 2/1992 | Stafford et al. |
| 5,089,233 A | 2/1992 | DeVaney et al. |
| 5,104,231 A | 4/1992 | Collier et al. |
| 5,104,621 A | 4/1992 | Pfost et al. |
| 5,104,807 A | 4/1992 | Mitsumaki et al. |
| 5,104,808 A | 4/1992 | Laska et al. |
| 5,122,343 A | 6/1992 | Ishizaka et al. |
| 5,128,103 A | 7/1992 | Wang et al. |
| 5,139,743 A | 8/1992 | Ishizaka et al. |
| 5,139,745 A | 8/1992 | Barr et al. |
| 5,141,871 A | 8/1992 | Kureshy et al. |
| 5,147,610 A | 9/1992 | Watanabe et al. |
| 5,154,888 A | 10/1992 | Zander et al. |
| 5,154,889 A | 10/1992 | Muraishi |
| 5,167,448 A | 12/1992 | Herold et al. |
| 5,183,638 A | 2/1993 | Wakatake |
| 5,186,827 A | 2/1993 | Liberti et al. |
| 5,192,505 A | 3/1993 | Sakagami |
| 5,192,506 A | 3/1993 | Kureshy et al. |
| 5,207,987 A | 5/1993 | Kureshy et al. |
| 5,213,761 A | 5/1993 | Sakagami |
| 5,215,714 A | 6/1993 | Okada et al. |
| 5,223,218 A | 6/1993 | Fukuoka et al. |
| 5,229,297 A | 7/1993 | Schnipelsky et al. |
| 5,232,665 A | 8/1993 | Burkovich et al. |
| 5,232,669 A | 8/1993 | Pardinas |
| 5,234,665 A | 8/1993 | Ohta et al. |
| 5,240,678 A | 8/1993 | Litsche |
| 5,240,679 A | 8/1993 | Stettler |
| 5,246,665 A | 9/1993 | Tyranski et al. |
| 5,250,261 A | 10/1993 | Porte |
| 5,254,315 A | 10/1993 | Nurse et al. |
| 5,260,028 A | 11/1993 | Astle |
| 5,270,210 A * | 12/1993 | Weyrauch et al. .............. 436/43 |
| 5,277,871 A | 1/1994 | Fuji et al. |
| 5,288,463 A | 2/1994 | Chemelli |
| 5,290,513 A | 3/1994 | Berthold et al. |
| 5,294,404 A | 3/1994 | Grandone et al. |
| 5,306,510 A | 4/1994 | Meltzer |
| 5,314,663 A | 5/1994 | Mimura |
| 5,314,825 A | 5/1994 | Weyrauch et al. |
| 5,316,726 A | 5/1994 | Babson et al. |
| 5,318,914 A | 6/1994 | Matte et al. |
| 5,320,809 A | 6/1994 | Dunn et al. |
| 5,320,966 A | 6/1994 | Mitsumaki et al. |
| 5,324,481 A | 6/1994 | Dunn et al. |
| 5,330,916 A | 7/1994 | Williams et al. |
| 5,332,549 A | 7/1994 | MacIndoe, Jr. |
| 5,340,747 A | 8/1994 | Eden |
| 5,346,303 A | 9/1994 | Heinonen et al. |
| 5,358,691 A | 10/1994 | Clark et al. |
| 5,360,741 A | 11/1994 | Hunnell |
| 5,374,395 A | 12/1994 | Robinson et al. |
| 5,380,666 A | 1/1995 | Wuerschum |
| 5,384,094 A | 1/1995 | Schacher |
| 5,389,339 A | 2/1995 | Petschek et al. |
| 5,397,709 A | 3/1995 | Berndt |
| 5,401,465 A | 3/1995 | Smethers et al. |
| 5,403,711 A | 4/1995 | Walder et al. |
| 5,415,839 A | 5/1995 | Zaun et al. |
| 5,415,840 A | 5/1995 | Sano et al. |
| 5,419,871 A | 5/1995 | Musak et al. |
| 5,422,271 A | 6/1995 | Chen et al. |
| 5,424,212 A | 6/1995 | Pinsl-Ober et al. |
| 5,434,083 A | 7/1995 | Mitsumaki et al. |
| 5,439,646 A | 8/1995 | Tanimizu et al. |
| 5,443,791 A | 8/1995 | Cathcart et al. |
| 5,445,794 A | 8/1995 | Wihlborg |
| 5,447,687 A | 9/1995 | Lewis et al. |
| 5,451,528 A | 9/1995 | Raymoure et al. |
| 5,460,780 A | 10/1995 | Devaney, Jr. et al. |
| 5,465,629 A | 11/1995 | Waylett, Jr. |
| 5,466,574 A | 11/1995 | Liberti et al. |
| 5,470,744 A | 11/1995 | Astle |
| 5,482,834 A | 1/1996 | Gillespie |
| 5,482,839 A | 1/1996 | Ashihara et al. |
| 5,482,861 A | 1/1996 | Clark et al. |

(56) References Cited

U.S. PATENT DOCUMENTS

| | | | |
|---|---|---|---|
| 5,507,410 | A | 4/1996 | Clark et al. |
| 5,512,247 | A | 4/1996 | Bonacina et al. |
| 5,525,300 | A | 6/1996 | Danssaert et al. |
| 5,527,673 | A | 6/1996 | Reinhartz et al. |
| 5,536,471 | A | 7/1996 | Clark et al. |
| 5,536,475 | A | 7/1996 | Moubayed et al. |
| 5,538,848 | A | 7/1996 | Livak et al. |
| 5,538,849 | A | 7/1996 | Uematsu et al. |
| 5,548,826 | A | 8/1996 | Sayers |
| 5,558,839 | A | 9/1996 | Matte et al. |
| 5,567,595 | A | 10/1996 | Kok |
| 5,571,325 | A | 11/1996 | Ueyama et al. |
| 5,571,481 | A | 11/1996 | Powell et al. |
| 5,575,976 | A | 11/1996 | Choperena et al. |
| 5,576,215 | A | 11/1996 | Burns et al. |
| 5,578,269 | A | 11/1996 | Yaremko et al. |
| 5,578,270 | A | 11/1996 | Reichler et al. |
| 5,580,524 | A | 12/1996 | Forrest et al. |
| 5,582,796 | A | 12/1996 | Carey et al. |
| 5,585,068 | A | 12/1996 | Panetz et al. |
| 5,587,129 | A | 12/1996 | Kurosaki et al. |
| 5,595,707 | A | 1/1997 | Copeland et al. |
| 5,599,501 | A | 2/1997 | Carey et al. |
| 5,605,665 | A | 2/1997 | Clark et al. |
| 5,610,069 | A | 3/1997 | Clark et al. |
| 5,620,898 | A | 4/1997 | Yaremko et al. |
| 5,635,364 | A | 6/1997 | Clark et al. |
| 5,637,275 | A | 6/1997 | Carey et al. |
| 5,639,425 | A | 6/1997 | Komiyama et al. |
| 5,646,049 | A | 7/1997 | Tayi |
| 5,653,940 | A | 8/1997 | Carey et al. |
| 5,656,493 | A | 8/1997 | Mullis et al. |
| 5,658,532 | A | 8/1997 | Kurosaki et al. |
| 5,658,799 | A | 8/1997 | Choperena et al. |
| 5,670,114 | A | 9/1997 | Sakazume et al. |
| 5,670,120 | A | 9/1997 | Degenhardt et al. |
| 5,670,375 | A | 9/1997 | Seaton et al. |
| 5,677,188 | A | 10/1997 | Mitsumaki et al. |
| 5,679,309 | A | 10/1997 | Bell |
| 5,681,530 | A | 10/1997 | Kuster et al. |
| 5,686,046 | A | 11/1997 | Malek et al. |
| 5,691,146 | A | 11/1997 | Mayrand |
| 5,693,292 | A | 12/1997 | Choperena et al. |
| 5,698,450 | A | 12/1997 | Ringrose et al. |
| 5,702,950 | A | 12/1997 | Tajima |
| 5,705,062 | A | 1/1998 | Knobel |
| 5,714,380 | A | 2/1998 | Neri et al. |
| 5,716,583 | A | 2/1998 | Smethers et al. |
| 5,720,377 | A | 2/1998 | Lapeus et al. |
| 5,720,923 | A | 2/1998 | Haff et al. |
| 5,730,938 | A | 3/1998 | Carbonari et al. |
| 5,730,939 | A | 3/1998 | Kurumada et al. |
| 5,736,105 | A | 4/1998 | Astle |
| 5,738,827 | A | 4/1998 | Marquiss |
| 5,741,461 | A | 4/1998 | Takahashi et al. |
| 5,746,977 | A | 5/1998 | Imai et al. |
| 5,746,978 | A | 5/1998 | Bienhaus et al. |
| 5,750,338 | A | 5/1998 | Collins et al. |
| 5,750,881 | A | 5/1998 | Dorenkott et al. |
| 5,762,872 | A | 6/1998 | Bûler et al. |
| 5,762,873 | A | 6/1998 | Fanning et al. |
| 5,773,268 | A | 6/1998 | Korenberg et al. |
| 5,773,662 | A | 6/1998 | Imai et al. |
| 5,779,981 | A | 7/1998 | Danssaert et al. |
| 5,786,182 | A | 7/1998 | Catanzariti et al. |
| 5,789,252 | A | 8/1998 | Fujita et al. |
| 5,795,547 | A | 8/1998 | Moser et al. |
| 5,795,784 | A | 8/1998 | Arnquist et al. |
| 5,800,989 | A | 9/1998 | Linn et al. |
| 5,807,523 | A | 9/1998 | Watts et al. |
| 5,814,277 | A | 9/1998 | Bell et al. |
| 5,826,129 | A | 10/1998 | Hasebe et al. |
| 5,827,478 | A | 10/1998 | Carey et al. |
| 5,827,479 | A | 10/1998 | Yamazaki et al. |
| 5,827,653 | A | 10/1998 | Sammes et al. |
| 5,837,195 | A | 11/1998 | Malek et al. |
| 5,843,376 | A | 12/1998 | Ishihara et al. |
| 5,846,491 | A | 12/1998 | Choperena et al. |
| 5,849,247 | A | 12/1998 | Uzan et al. |
| 5,855,847 | A | 1/1999 | Oonuma et al. |
| 5,863,506 | A | 1/1999 | Farren |
| 5,876,668 | A | 3/1999 | Kawashima et al. |
| 5,876,930 | A | 3/1999 | Livak et al. |
| 5,882,594 | A | 3/1999 | Kawaguchi et al. |
| 5,882,596 | A | 3/1999 | Breeser et al. |
| 5,882,918 | A | 3/1999 | Goffe |
| 5,885,353 | A | 3/1999 | Strodtbeck et al. |
| 5,885,529 | A | 3/1999 | Babson et al. |
| 5,885,530 | A | 3/1999 | Babson et al. |
| 5,888,454 | A | 3/1999 | Leistner et al. |
| 5,897,783 | A | 4/1999 | Howe et al. |
| 5,919,622 | A | 7/1999 | Macho et al. |
| 5,928,869 | A | 7/1999 | Nadeau et al. |
| 5,935,791 | A | 8/1999 | Nadeau et al. |
| 5,948,691 | A | 9/1999 | Ekiriwang et al. |
| 5,958,763 | A | 9/1999 | Goffe |
| 5,985,670 | A | 11/1999 | Markin |
| 5,985,671 | A | 11/1999 | Leistner et al. |
| 5,985,672 | A | 11/1999 | Kegelman et al. |
| 5,988,869 | A | 11/1999 | Davidson et al. |
| 5,994,056 | A | 11/1999 | Higuchi |
| 6,027,691 | A | 2/2000 | Watts et al. |
| 6,033,574 | A | 3/2000 | Siddiqi |
| 6,033,880 | A | 3/2000 | Haff et al. |
| 6,042,786 | A | 3/2000 | Oonuma et al. |
| 6,043,880 | A | 3/2000 | Andrews et al. |
| 6,051,101 | A | 4/2000 | Ohtani et al. |
| 6,056,923 | A | 5/2000 | Diamond et al. |
| 6,066,455 | A | 5/2000 | Kruse-Mueller et al. |
| 6,068,978 | A | 5/2000 | Zaun et al. |
| 6,071,395 | A | 6/2000 | Lange |
| 6,086,827 | A | 7/2000 | Horner et al. |
| 6,096,272 | A | 8/2000 | Clark et al. |
| 6,103,193 | A | 8/2000 | Iwahashi et al. |
| 6,110,676 | A | 8/2000 | Coull et al. |
| 6,110,678 | A | 8/2000 | Weisburg et al. |
| 6,117,392 | A | 9/2000 | Hanawa et al. |
| 6,117,398 | A | 9/2000 | Bienhaus et al. |
| 6,117,683 | A | 9/2000 | Kodama et al. |
| 6,124,138 | A | 9/2000 | Woudenberg et al. |
| 6,129,428 | A | 10/2000 | Helwig et al. |
| 6,140,054 | A | 10/2000 | Wittwer et al. |
| 6,143,578 | A | 11/2000 | Bendele et al. |
| 6,146,592 | A | 11/2000 | Kawashima et al. |
| 6,156,565 | A | 12/2000 | Maes et al. |
| 6,165,778 | A | 12/2000 | Kedar |
| 6,180,408 | B1 | 1/2001 | Kwok et al. |
| 6,193,892 | B1 | 2/2001 | Krueger et al. |
| 6,214,293 | B1 | 4/2001 | Pantoliano et al. |
| 6,277,332 | B1 | 8/2001 | Sucholeiki |
| 6,300,068 | B1 | 10/2001 | Berg et al. |
| 6,335,166 | B1 | 1/2002 | Ammann et al. |
| 6,346,384 | B1 | 2/2002 | Poliner |
| 6,377,342 | B1 | 4/2002 | Coeurveille |
| 6,379,888 | B1 | 4/2002 | Nadeau et al. |
| 6,387,621 | B1 | 5/2002 | Wittwer |
| 6,396,581 | B1 | 5/2002 | Hayashi et al. |
| 6,399,952 | B1 | 6/2002 | Maher et al. |
| 6,409,925 | B1 | 6/2002 | Gombinsky et al. |
| 6,410,235 | B1 | 6/2002 | Weindel et al. |
| 6,436,349 | B1 | 8/2002 | Carey et al. |
| 6,472,156 | B1 | 10/2002 | Wittwer et al. |
| 6,503,751 | B2 | 1/2003 | Hugh |
| 6,517,777 | B2 | 2/2003 | Liljestrand et al. |
| 6,517,782 | B1 | 2/2003 | Horner et al. |
| 6,517,783 | B2 * | 2/2003 | Horner et al. ............ 422/549 |
| 6,577,580 | B2 | 6/2003 | Haga |
| 6,586,234 | B1 | 7/2003 | Burg et al. |
| 6,597,450 | B1 | 7/2003 | Andrews et al. |
| 6,605,213 | B1 | 8/2003 | Ammann et al. |
| 6,617,138 | B1 | 9/2003 | Rudi et al. |
| 6,699,661 | B1 | 3/2004 | Kurane et al. |
| 6,730,501 | B2 | 5/2004 | Eyre et al. |
| 6,764,649 | B2 | 7/2004 | Ammann |

(56) References Cited

U.S. PATENT DOCUMENTS

| | | |
|---|---|---|
| 6,790,623 B2 | 9/2004 | Weindel et al. |
| 6,815,164 B2 | 11/2004 | Kurn |
| 6,825,921 B1 | 11/2004 | Modlin et al. |
| 6,890,742 B2 | 5/2005 | Ammann et al. |
| 6,902,900 B2 | 6/2005 | Davies et al. |
| 6,919,058 B2 | 7/2005 | Andersson et al. |
| 6,919,175 B1 | 7/2005 | Bienhaus et al. |
| 6,943,029 B2 | 9/2005 | Copeland et al. |
| 6,961,948 B2 | 11/2005 | Seki et al. |
| 7,081,226 B1 | 7/2006 | Wittwer et al. |
| 7,081,339 B2 | 7/2006 | Siepnev |
| 7,087,414 B2 | 8/2006 | Gerdes et al. |
| 7,115,384 B2 | 10/2006 | Clark et al. |
| 7,118,982 B2 | 10/2006 | Govyadinov et al. |
| 7,183,084 B2 | 2/2007 | Jaeger |
| 7,220,385 B2 | 5/2007 | Blecka et al. |
| 7,252,937 B2 | 8/2007 | Kaltenboeck |
| 7,262,008 B2 | 8/2007 | Catanzariti et al. |
| 7,267,945 B2 | 9/2007 | Baskin et al. |
| 7,273,749 B1 | 9/2007 | Wittwer et al. |
| 7,354,707 B2 | 4/2008 | Kurane et al. |
| 7,373,253 B2 | 5/2008 | Eyre |
| 7,390,459 B2 | 6/2008 | Lebl et al. |
| 7,498,164 B2 | 3/2009 | Oldham et al. |
| 7,635,588 B2 | 12/2009 | King et al. |
| 7,794,659 B2 | 9/2010 | Lair et al. |
| 7,897,337 B2 | 3/2011 | Macioszek et al. |
| 7,932,081 B2 | 4/2011 | Lair et al. |
| 7,964,413 B2 | 6/2011 | Macioszek et al. |
| 8,008,066 B2 | 8/2011 | Lair et al. |
| 2001/0007643 A1* | 7/2001 | Horner et al. ............... 422/102 |
| 2001/0012492 A1* | 8/2001 | Acosta et al. ............... 3-502167 |
| 2001/0019826 A1* | 9/2001 | Ammann ....................... 435/6 |
| 2002/0028489 A1 | 3/2002 | Ammann et al. |
| 2002/0031446 A1 | 3/2002 | Friedlander et al. |
| 2002/0031768 A1 | 3/2002 | McMillan et al. |
| 2002/0064867 A1 | 5/2002 | Clark et al. |
| 2002/0086417 A1 | 7/2002 | Chen et al. |
| 2002/0090320 A1 | 7/2002 | Burow et al. |
| 2002/0098117 A1* | 7/2002 | Ammann et al. ............... 422/64 |
| 2002/0123156 A1 | 9/2002 | Tajima |
| 2002/0137039 A1 | 9/2002 | Gessner |
| 2002/0137194 A1 | 9/2002 | Ammann et al. |
| 2002/0137197 A1 | 9/2002 | Ammann et al. |
| 2002/0155619 A1 | 10/2002 | Kurihara et al. |
| 2002/0197611 A1 | 12/2002 | Chagovetz |
| 2003/0027206 A1 | 2/2003 | Ammann et al. |
| 2003/0054542 A1 | 3/2003 | Burns et al. |
| 2003/0087240 A1 | 5/2003 | Whitcombe |
| 2003/0087397 A1 | 5/2003 | Klein et al. |
| 2003/0129614 A1 | 7/2003 | Parameswaran et al. |
| 2004/0014202 A1 | 1/2004 | King et al. |
| 2004/0033518 A1 | 2/2004 | Wittwer et al. |
| 2004/0076983 A1 | 4/2004 | Karisen |
| 2004/0115796 A1 | 6/2004 | Burns |
| 2004/0208795 A1 | 10/2004 | Toi et al. |
| 2005/0064582 A1 | 3/2005 | Wittwer et al. |
| 2005/0123445 A1 | 6/2005 | Blecka et al. |
| 2005/0130198 A1 | 6/2005 | Ammann et al. |
| 2005/0178795 A1* | 8/2005 | Inoue ............................ 222/23 |
| 2005/0220669 A1 | 10/2005 | Malyarov et al. |
| 2005/0220670 A1 | 10/2005 | Palmieri et al. |
| 2006/0051246 A1 | 3/2006 | Toi et al. |
| 2006/0211130 A1 | 9/2006 | Macioszek et al. |
| 2007/0009392 A1 | 1/2007 | Tajima et al. |
| 2008/0096214 A1* | 4/2008 | Ammann et al. ............... 435/6 |
| 2008/0102527 A1* | 5/2008 | Ammann et al. ............... 436/43 |
| 2009/0301189 A1* | 12/2009 | Ross et al. ............... 73/304 |
| 2010/0075336 A1 | 3/2010 | Knight et al. |
| 2010/0288395 A1* | 11/2010 | Hagen et al. ............... 141/234 |
| 2010/0294047 A1* | 11/2010 | Davis et al. ............... 73/863.21 |
| 2011/0270542 A1* | 11/2011 | Chappell et al. ............... 702/55 |
| 2012/0010844 A1* | 1/2012 | Landry et al. ............... 702/127 |

FOREIGN PATENT DOCUMENTS

| | | |
|---|---|---|
| EP | 0136126 A2 | 4/1985 |
| EP | 0171140 A2 | 2/1986 |
| EP | 0272055 A2 | 6/1988 |
| EP | 0293782 A1 | 12/1988 |
| EP | 0336309 A2 | 10/1989 |
| EP | 0409126 A2 | 1/1991 |
| EP | 0411620 A2 | 2/1991 |
| EP | 0435481 A2 | 7/1991 |
| EP | 0458138 A2 | 11/1991 |
| EP | 0502638 A2 | 9/1992 |
| EP | 0513618 A2 | 11/1992 |
| EP | 0525577 A2 | 2/1993 |
| EP | 0542422 A1 | 5/1993 |
| EP | 0569214 A2 | 11/1993 |
| EP | 0571033 A1 | 11/1993 |
| EP | 0628824 A1 | 12/1994 |
| EP | 0640828 B1 | 3/1995 |
| EP | 0885958 A1 | 12/1998 |
| EP | 1024355 A1 | 8/2000 |
| EP | 1138784 A2 | 10/2001 |
| GB | 2081118 A | 2/1982 |
| GB | 2131168 A | 6/1984 |
| JP | 57171266 | 10/1982 |
| JP | 61-241884 A | 11/1985 |
| JP | 61-274697 A | 12/1986 |
| JP | 62-000863 A | 1/1987 |
| JP | 62-044663 A | 2/1987 |
| JP | 63003265 A | 1/1988 |
| JP | 02-066461 A | 3/1990 |
| JP | 03-007571 A | 1/1991 |
| JP | 03-105251 A2 | 5/1991 |
| JP | 3-502167 A | 5/1991 |
| JP | 04-328467 A | 11/1992 |
| JP | 04-359154 A | 12/1992 |
| JP | 05-010957 A | 1/1993 |
| JP | 05-317030 A | 12/1993 |
| JP | 06-197797 A | 7/1994 |
| JP | 6-509647 A | 10/1994 |
| JP | 07-075544 A | 3/1995 |
| JP | 7-501933 A | 3/1995 |
| JP | 7/107975 A2 | 4/1995 |
| JP | 7/107999 A2 | 4/1995 |
| JP | 7-191042 A | 7/1995 |
| JP | 7-506184 A | 7/1995 |
| JP | 8-9957 A | 1/1996 |
| JP | 8/320274 A | 12/1996 |
| JP | 9-503660 A | 4/1997 |
| JP | 9-121899 A | 5/1997 |
| JP | 9-504428 A | 5/1997 |
| JP | 9-504610 A | 5/1997 |
| JP | 9-224644 A | 9/1997 |
| JP | 10311840 A | 11/1998 |
| JP | 11-503315 A | 3/1999 |
| JP | 2000-500331 A | 1/2000 |
| JP | 2000-214090 A | 8/2000 |
| JP | 2001-059848 A | 3/2001 |
| JP | 2001-503730 A | 3/2001 |
| JP | 2004-520574 A | 7/2004 |
| WO | WO 90/08840 A1 | 8/1990 |
| WO | WO 9115768 A1 | 10/1991 |
| WO | WO 93/03383 A1 | 2/1993 |
| WO | WO 93/07292 A1 | 4/1993 |
| WO | WO 93/20450 A1 | 10/1993 |
| WO | WO 93/25912 A2 | 12/1993 |
| WO | WO 95/11454 A1 | 4/1995 |
| WO | WO 96/31781 A1 | 10/1996 |
| WO | WO 97/16561 A1 | 5/1997 |
| WO | WO 9731105 A1 | 8/1997 |
| WO | WO 97/34908 A1 | 9/1997 |
| WO | WO 9746707 A2 | 12/1997 |
| WO | WO 98/00697 A1 | 1/1998 |

(56) References Cited

FOREIGN PATENT DOCUMENTS

WO        WO 01/04608 A1     1/2001
WO        WO 2005-059568 A1     6/2005

OTHER PUBLICATIONS 5,998,201, 12/1999, Maes et al. (withdrawn).

Anonymous, "Cup and Tip Supply Ring," Research Disclosure, Mason Publications, Emsworth GB, No. 318, 3 pages (Oct. 1990).

Bowie et al., "α-Thalassemia Subtyping the the Detection of Silent Mutations by High-Resolution Fragment Analysis and DNA Sequencing", Mol. Diagn., 3: 43-53 (Mar. 1998).

Kristensen et al., "High-Throughput Screening for Known Mutations by Automated Analysis of Single Sequencing Reactions", BioTechniques, 24: 832-835 (May 1998).

Leonard et al., "Preparation of PCR Products for DNA Sequencing", BioTechniques, 24: 314-317 (Feb. 1998).

Schmitz et al., "Recent Advances in Molecular Genetics of Cardiovascular Disorders—Implications for Atherosclerosis and Diseases of Cellular Lipid Metabolism", Pathol. Oncol. Res. 4: 153-161 (1998).

Van Gemen, et al., "The One-tube Quantitative HIV-1 RNA NASBA: Precision, Accuracy, and Application", PCR Methods and Applications, 4:S177-S184, Cold Spring Harbor Laboratory (1995).

Wu et al., "Strategies for Unambiguous Detection of Allelic Heterozygosity via Direct DNA Sequencing of PCR Products: Application to the HLA DRB1 Locus", Mol. Diagn., 1: 89-98 (Jun. 1996).

EPO Search Report, European Patent Application No. 08003851.6, 10 pages. (Aug. 19, 2008).

International Search Report and Written Opinion in PCT/US2011/045890, 13 pages (mailed Oct. 4, 2011).

Notice of Reasons for Rejection and English translation in Japanese Application No. 2008-501021, 11 pages (mailed Sep. 7, 2011).

\* cited by examiner

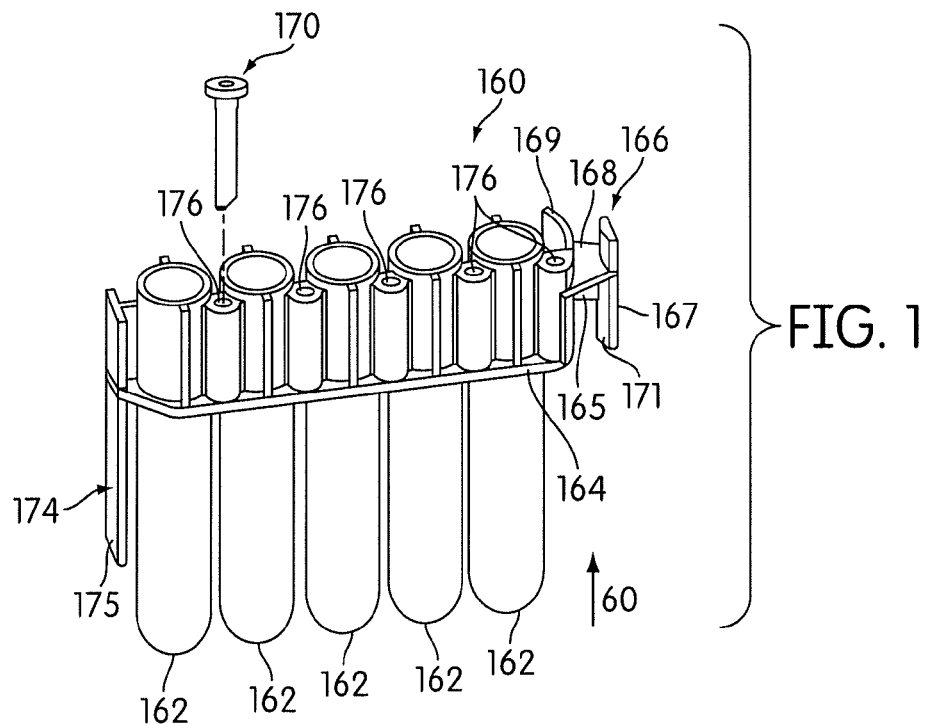
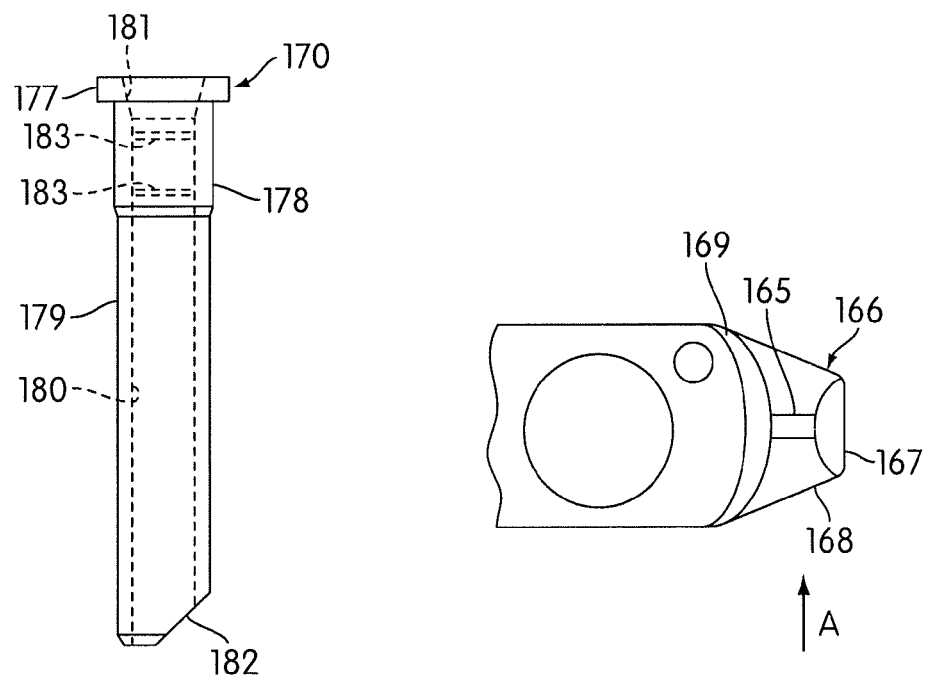
FIG. 1
FIG. 2
FIG. 3

METHOD, SYSTEM AND APPARATUS FOR INCORPORATING CAPACITIVE PROXIMITY SENSING IN AN AUTOMATED FLUID TRANSFER PROCEDURE

CROSS-REFERENCE TO RELATED APPLICATIONS

This application claims the benefit under 35 U.S.C. §119 (e) of U.S. Provisional Application No. 61/368,759, filed Jul. 29, 2010 and U.S. Provisional Application No. 61/423,254, filed Dec. 15, 2010 the disclosures of which are hereby incorporated by reference in their entirety.

FIELD OF THE INVENTION

The present invention relates to automated fluid transfer in an automated analyzer for performing multiple diagnostic assays simultaneously and, more specifically, to means for detecting fluid level within a receptacle as well as for confirming the presence or absence of a protective tip at a distal end of a fluid transfer probe.

BACKGROUND OF THE INVENTION

None of the references described or referred to herein are admitted to be prior art to the claimed invention.

Nucleic acid-based assays and other reactions (e.g., chemical or biological) are frequently performed on automated, computer-controlled analyzers that include an automated fluid transfer apparatus configured to transfer fluids into and/ or out of one or more receptacles by means of one or more fluid transfer probes. Each fluid transfer probe will typically be used to transfer fluids into and out of multiple different receptacles. Therefore, to prevent or limit cross-contamination between different receptacles accessed by the same fluid transfer probe, the fluid transfer probe is preferably covered during fluid transfer operations at its distal end by a protective conduit, such as a disposable tip. A tip is engaged by a fluid transfer probe prior to commencing fluid transfer with respect to a particular receptacle and is then discarded when fluid transfer is complete for that receptacle. Thus, residual fluid that may otherwise remain on the distal end of a fluid transfer probe, and get carried over into subsequent receptacles, i.e. cross-contamination, instead remains on the end of a tip and is discarded with the tip.

In an automated system, automated determinations of certain conditions or parameters affecting the fluid transfer apparatus must be made. For example automated determination of fluid level in the receptacle provides verification that the amount of fluid dispensed into or removed from the receptacle is correct. Automated confirmation of the presence of a tip on the fluid transfer probe ensures that a tip has been properly engaged prior to commencing fluid transfer for a particular receptacle. Similarly, automated confirmation of the absence of a tip at the end of the fluid transfer probe ensures that the tip has been properly discarded following the fluid transfer for the receptacle.

Known systems for detecting a fluid level within a receptacle in an automated analyzer include capacitive level sensing systems. In one implementation of such a system, the fluid transfer probe and the receptacle and its fluid contents comprise components of a system for which the electrical capacitance can be measured. When the probe contacts a fluid level surface within the receptacle, a measurable change of the capacitance occurs, so that contact with the fluid level surface can be detected.

The presence or absence of a protective tip on a fluid transfer probe can be detected by means of an optical detector. For example, the optical detector may comprise an emitter component and a detector component, and the fluid transfer probe can be moved into the optical path so as to place the protective tip between the emitter component and the detector component. If the tip is present, the optical path is blocked, and if the tip is absent, the optical path is unblocked.

The use of an optical detector to detect the presence or absence of a protective tip adds another layer of complexity to the fluid transfer apparatus, especially if the apparatus includes multiple fluid transfer probes, each of which requiring confirmation of the presence and absence of a protective tip. Furthermore, optical detectors are vulnerable to performance degradation due to dust or spillage on the emitter and/or detector component.

SUMMARY OF THE INVENTION

Aspects of the invention are embodied in a fluid transfer apparatus configured to transfer fluids into and/or out of one or more receptacles by means of one or more fluid transfer probes. In one embodiment, one fluid transfer probe is associated with each reaction receptacle.

A fluid transfer apparatus embodying aspects of the present invention incorporates a capacitive proximity sensor system configured to detect contact by the fluid transfer probe with fluid within the receptacle and to detect the presence or absence of the tip at a distal end of the fluid transfer probe. Thus, the same capacitive proximity sensor system that is employed to verify fluid volume within the receptacle by detecting the fluid level in the receptacle is also employed to verify the engagement and removal of a tip at the distal end of the fluid transfer probe.

The use of a unified capacitive sensing system that can test both for presence of fluid in a receptacle as well as the presence of a conduit on the distal end of a fluid transfer probe allows the construction of a fluid transfer apparatus without the use of optical sensors which would otherwise verify the level of fluid in a receptacle device or verify the presence or removal of conduits. The capacitive sensing system described herein thus addresses a need to avoid the risk of inaccuracy or errors caused when optical sensors in sufficiently close proximity to fluids become wet or corroded and do not accurately and consistently detect fluid or detect the presence of absence of protective conduits on fluid transfer probes.

Thus, aspects of the invention are embodied in a method for monitoring the status of a fluid transfer probe. The method comprises the steps of moving a fluid transfer probe known to have a protective tip on its distal end with respect to a secondary structure, measuring a first reference signal from the fluid transfer probe with the protective tip disposed on its distal end, moving a fluid transfer probe known to lack a protective tip on its distal end with respect to the secondary structure, and measuring a second reference signal from the fluid transfer probe lacking a protective tip. A reference value is derived from either or both of the first reference signal and the second reference signal. Whether or not a fluid transfer probe has a protective tip engaged on its end is determined by moving the fluid transfer probe with respect to the secondary structure, measuring a signal from the fluid transfer probe as the fluid transfer probe is moved with respect to the secondary structure, and comparing at least one characteristic of the measured signal with the reference value.

In one embodiment, the reference value comprises a value between a mean of the first reference signal and a mean of the second reference signal.

In one embodiment, the amplitude of the measured signal from the fluid transfer probe is based on the capacitance between the fluid transfer probe and the secondary structure, and the capacitance between the fluid transfer probe and the secondary structure depends on whether a protective tip is disposed on the fluid transfer probe.

In one embodiment, the method further comprises the step of detecting when the fluid transfer probe contacts a fluid surface within a receptacle by lowering the fluid transfer probe with a protective tip disposed thereon into the receptacle, measuring a signal from the fluid transfer probe while lowering the fluid transfer probe into the receptacle, and detecting a change in a characteristic of the signal exceeding a threshold value by comparing a value of the characteristic with the threshold value to indicate that the protective tip on the fluid transfer probe has contacted the fluid surface.

In one embodiment, the threshold value comprises a predetermined change in amplitude occurring within a predetermined movement distance of the fluid transfer probe, and detecting a change in a characteristic of the signal comprises comparing the amplitude of the signal during movement of the fluid transfer probe into the receptacle with the threshold value.

In one embodiment, the threshold value comprises a predetermined rate of change in amplitude, and detecting a change in a characteristic of the signal comprises comparing the rate of change of the amplitude of the signal during movement of the fluid transfer probe into the receptacle with the threshold value.

In one embodiment, comparing at least one characteristic of the measured signal with the reference value comprises comparing the amplitude of the measured signal with a reference amplitude, wherein the reference amplitude is derived from an amplitude of the first reference signal and an amplitude of the second reference signal.

In one embodiment, comparing at least one characteristic of the measured signal with the reference value comprises comparing a rate of change of the measured signal with a reference rate, wherein the reference rate is derived from a rate of change of the first reference signal and a rate of change of the second reference signal. Specifically, in another embodiment, the reference rate is derived by determining a mean rate of change of the first reference signal, determining a mean rate of change of the second reference signal, and setting as the reference rate a value between the mean rate of change of the first reference signal and the mean rate of change of the second reference signal.

Further aspects of the invention are embodied in a method for monitoring the status of a fluid transfer probe comprising the steps of moving the fluid transfer probe with respect to a secondary structure, measuring a first signal related to capacitance of a group of components including the fluid transfer probe while moving the fluid transfer probe with respect to the secondary structure, and determining if a protective tip is disposed on the fluid transfer probe based on the first signal.

In one embodiment, determining if a protective tip is disposed on the fluid transfer probe comprises comparing the amplitude of the first signal with a reference amplitude, wherein the reference amplitude is derived from (a) a first reference signal measured from a fluid transfer probe with a protective tip on its distal end as the fluid transfer probe and protective tip are moved with respect to the secondary structure and (b) a second reference signal measured from a fluid transfer probe lacking a protective tip on its distal end as the fluid transfer probe is moved with respect to the secondary structure and/or comparing the amount of variation of the first signal with a reference variation, wherein the reference variation is derived from the first reference signal and the second reference signal.

In one embodiment, the method further comprises the steps of lowering the fluid transfer probe with a protective tip disposed thereon into a receptacle, measuring a second signal related to the capacitance of a group of components including the fluid transfer probe while lowering the fluid transfer probe into the receptacle, and detecting if the protective tip disposed on the fluid transfer probe has contacted a fluid surface within the receptacle based on the second signal.

In one embodiment, detecting if the protective tip disposed on the fluid transfer probe has contacted a fluid surface comprises detecting at least one of: (1) a change in the amplitude of the second signal exceeding a predefined threshold or (2) a change in the rate of change in the amplitude of the second signal exceeding a predefined threshold, to indicate that the fluid transfer probe has contacted a fluid surface.

In one embodiment, two or more fluid transfer probes are moved simultaneously with respect to the secondary structure. For each fluid transfer probe moved with respect to the secondary structure, a first signal related to capacitance of a group of components including that fluid transfer probe is measured. Whether a protective tip is disposed on each fluid transfer probe is determined based on the first signal measured for that fluid transfer probe. In another embodiment, each of the two or more fluid transfer probes is lowered simultaneously into a receptacle, and, for each fluid transfer probe, a second signal related to capacitance of a group of components including that fluid transfer probe is measured while lowering the fluid transfer probes into the receptacle, and if each fluid transfer probe has contacted a fluid surface within the receptacle is determined based on the second signal measured for that fluid transfer probe.

In one embodiment, the fluid transfer probe is moved with respect to the secondary structure, and the first signal is measured two or more times, for example, three times, before the presence of a protective tip is determined based on the first signal. The first signals measured two or more times may be averaged, and whether a protective tip is disposed on the fluid transfer probe may be determined based on an average first signal.

In one embodiment, the position of the fluid transfer probe is monitored while determining if the protective tip has contacted a fluid level surface to determine an amount of fluid contained within the receptacle when contact with the fluid surface is detected.

In one embodiment, moving the fluid transfer probe with respect to the secondary structure comprises moving the fluid transfer probe one or more times between a first position with respect to the secondary structure and a second position with respect to the secondary structure. Determining if a protective tip is disposed on the fluid transfer probe based on the first signal may comprise subtracting the first signal measured at the first position with respect to the secondary structure and the first signal measured at the second position with respect to the secondary structure and comparing the difference to a predetermined threshold.

In one embodiment, determining if a protective tip is disposed on the fluid transfer probe based on the first signal comprises determining the slope of the first signal and comparing the slope of the first signal to a predetermined threshold.

In one embodiment, the predetermined threshold is determined by moving a fluid transfer probe known to have a protective tip on its distal end with respect to the secondary structure, measuring a first reference signal related to capacitance of the fluid transfer probe and protective tip while moving the fluid transfer probe and protective tip with respect to the secondary structure, moving a fluid transfer probe known to lack a protective tip on its distal end with respect to the secondary structure, measuring a second reference signal related to capacitance of the fluid transfer probe while moving the fluid transfer probe with respect to the secondary structure, determining a mean slope of the first reference signal, determining a mean slope of the second reference signal, and setting as the threshold a value between the mean slope of the first reference signal and the mean slope of the second reference signal.

Other aspects of the invention are embodied in a fluid transfer system comprising a fluid transfer probe configured to aspirate fluid from a receptacle and/or dispense fluid into a receptacle, a probe control module constructed and arranged to enable the probe to engage a protective tip at a distal end of the fluid transfer probe, and a tip detection system. The tip detection system is configured to determine if a fluid transfer probe has a protective tip engaged on its distal end by (a) measuring a signal related to capacitance of a group of components including the fluid transfer probe as the fluid transfer probe is moved with respect to a secondary structure and (b) determining if a protective tip is engaged on the fluid transfer probe based on the measured signal.

In one embodiment, the system further comprises a liquid level detection system configured to detect if the fluid transfer probe has contacted a fluid surface within a receptacle by (a) measuring a second signal related to capacitance of a group of components including the fluid transfer probe while the fluid transfer probe is being lowered into the receptacle and (b) detecting if the protective tip engaged on the fluid transfer probe has contacted a fluid surface within the receptacle based on the second signal.

In one embodiment, the system further comprises a protective tip removal structure configured to be engaged by the fluid transfer probe and to remove a protective tip from the fluid transfer probe, and the probe control module is further constructed and arranged to cause the fluid transfer probe to move into engagement with the protective tip removal structure.

In one embodiment, the protective tip detection system comprises a proximity sensor circuit configured to propagate a signal to the fluid transfer probe, and the proximity sensor circuit may include an electric field imaging device. The proximity sensor circuit may be configured to propagate a sine wave signal to the fluid transfer probe.

In one embodiment, the probe control module comprises a threaded drive screw, a threaded drive sleeve directly or indirectly connected to the fluid transfer probe and with which the drive screw is operatively coupled, and a motor operatively coupled to the drive screw and configured to effect powered rotation of the drive screw. Engagement between the drive screw and the drive sleeve converts rotation of the drive screw into translation of the fluid transfer probe.

In one embodiment, the secondary structure comprises a block with an opening formed therein, and the fluid transfer probe extends into the opening when the fluid transfer probe is moved with respect to the secondary structure. In another embodiment, the opening comprises a hole formed through the block, the hole is formed to have two different diameters, and the diameter of an upper portion of the hole is smaller than the diameter of a lower portion of the hole.

In one embodiment, the system comprises two or more fluid transfer probes and the tip detection system is configured to determine if each fluid transfer probe has a protective tip engaged on its distal end by, for each fluid transfer probe, (a) measuring a signal related to capacitance of a group of components including the fluid transfer probe as the fluid transfer probe is moved with respect to a secondary structure and (b) determining if a protective tip is engaged on the fluid transfer probe based on the measured signal for that fluid transfer probe.

In one embodiment, the tip detection system is configured to determine if a fluid transfer probe has a protective tip engaged on its distal end by comparing the amplitude of the measured signal with a reference amplitude, wherein the reference amplitude is derived from (a) a first reference signal measured from a fluid transfer probe with a protective tip on its distal end as the fluid transfer probe and protective tip are moved with respect to the secondary structure and (b) a second reference signal measured from a fluid transfer probe lacking a protective tip on its distal end as the fluid transfer probe is moved with respect to the secondary structure and/or by comparing the amount of variation of the measured signal with a reference variation, wherein the reference variation is derived from the first reference signal and the second reference signal.

Further aspects of the invention are embodied in a method for removing a protective tip from a fluid transfer probe. The fluid transfer probe with a protective tip secured to a distal end thereof is moved into engagement with a tip removal structure and a relative movement between the fluid transfer probe and the tip removal structure is effected to remove the tip from the distal end of the fluid transfer probe. Removal of the protective tip from the distal end of the fluid transfer probe is confirmed by (1) measuring a signal related to capacitance of a group of components including the fluid transfer probe and (2) confirming that the protective tip is absent from the fluid transfer probe based on the signal.

Further aspects of the invention are embodied in a method for transferring a fluid to and/or from a receptacle with a fluid transfer probe. The fluid transfer probe is lowered into engagement with a protective tip to removably secure the protective tip on a distal end of the fluid transfer probe. Whether the protective tip was successfully secured to the distal end of the fluid transfer probe is confirmed by moving the fluid transfer probe with respect to a secondary structure, measuring a first signal related to capacitance of a group of components including the fluid transfer probe while moving the fluid transfer probe with respect to the secondary structure, and confirming that the protective tip is secured to the fluid transfer probe based on the first signal. After securing the protective tip to the fluid transfer probe, the fluid transfer probe is lowered into the receptacle and fluid is withdrawn from or dispensed into the receptacle. A level of fluid within the receptacle is detected by (1) lowering the fluid transfer probe with the protective tip secured thereto into the receptacle, (2) measuring a second signal related to the capacitance of a group of components including the fluid transfer probe while lowering the fluid transfer probe into the receptacle, and (3) detecting if the protective tip secured to the fluid transfer probe has contacted a fluid surface within the receptacle based on the second signal. After detecting a fluid level, the fluid transfer probe and protective tip are moved into engagement with a tip removal structure and a relative movement between the fluid transfer probe and the tip removal structure is effected to remove the tip from the distal end of the fluid transfer probe. Removal of the protective tip from the distal end of the fluid transfer probe is confirmed by (1) measuring a third signal related to capacitance of a group of components including the fluid transfer probe and (2) confirming that the protective tip is absent from the fluid transfer probe based on the third signal.

In one embodiment, confirming removal of the protective tip comprises moving the fluid transfer probe with respect to a secondary structure and measuring the third signal while the fluid transfer probe is moved with respect to the secondary structure.

In one embodiment, confirming removal of the protective tip comprises measuring the third signal while moving the fluid transfer probe with respect to the tip removal structure to detect a change in the third signal that is indicative of the absence of the protective tip from the fluid transfer probe after effecting the relative movement between the fluid transfer probe and the tip removal structure.

In one embodiment, the tip removal structure comprises a plate having a keyhole-shaped opening formed therein, the keyhole-shaped opening having a first portion and a second portion, and the diameter of the first portion is larger than the diameter of the second portion. Moving the fluid transfer probe with respect to the tip removal structure comprises moving the fluid transfer probe with the protective tip secured to the distal end thereof into the first portion of the keyhole-shaped opening, effecting a lateral relative movement between the plate and the fluid transfer probe to move the fluid transfer probe into the second portion of the key-hole shaped opening, whereby at least one of the fluid transfer probe or the protective tip contacts the plate when the fluid transfer probe is moved into the second portion of the key-hole shaped opening thereby causing a detectable change in the measured third signal, and moving the fluid transfer probe out of the keyhole-shaped opening. Confirming removal of the protective tip comprises determining from the third signal if the protective tip is still in contact with the plate after moving the fluid transfer probe out of the keyhole-shaped opening by a distance that is less than a length of the protective tip.

These and other features, aspects, and advantages of the present invention will become apparent to those skilled in the art after considering the following detailed description, appended claims and accompanying drawings.

DESCRIPTION OF THE DRAWINGS

FIG. 3 is an enlarged bottom view of a portion of the multiple receptacle device, viewed in the direction of arrow "60" in FIG. 1;

DETAILED DESCRIPTION

The present invention is embodied in methods, systems, and apparatus for incorporating capacitive proximity sensing into an automated process for transferring fluid to and/or from a receptacle. Automated fluid transfer may be effected by a pipetting device under microprocessor control (i.e., a robotic pipetter). Such automated pipetting may involve the use of protective, contamination-limiting tips on the pipetting probe to isolate the probe from the materials being transferred by the pipetting device. Also, it is necessary, in a fully automated process, to provide confirmation of the transfer (i.e., dispense and/or removal) of the proper amounts of fluid. Accordingly, aspects of the present invention include the use of a capacitive proximity sensor system for detecting the level of a fluid in a receptacle—for verifying that the correct amount of fluid is in the receptacle—and for confirming that a protective tip is disposed on the fluid transfer probe prior to beginning the transfer and that the tip has been stripped from the probe following the transfer (so that a new probe can be placed on the probe for the next transfer).

Such a system is described in the present disclosure in the context of a magnetic separation wash station configured to automatically perform a magnetic separation isolation of a target substance from a fluid sample contained within a receptacle comprising a multiple receptacle device. Such a station may be one module of a diagnostic analyzer—for example, an analyzer for performing nucleic acid diagnostic assays—that also includes, among other modules, incubators, signal detectors, transfer mechanisms for automatically transferring receptacles between the various modules, and a microprocessor controller for controlling the operation and interoperation of the modules. The disclosure in this context, however, is provided as a non-limiting example. Capacitive proximity sensing for fluid level and tip detection as described herein may be incorporated into any automated fluid transfer instrument or process.

Multiple Receptacle Device

Figure 23A:
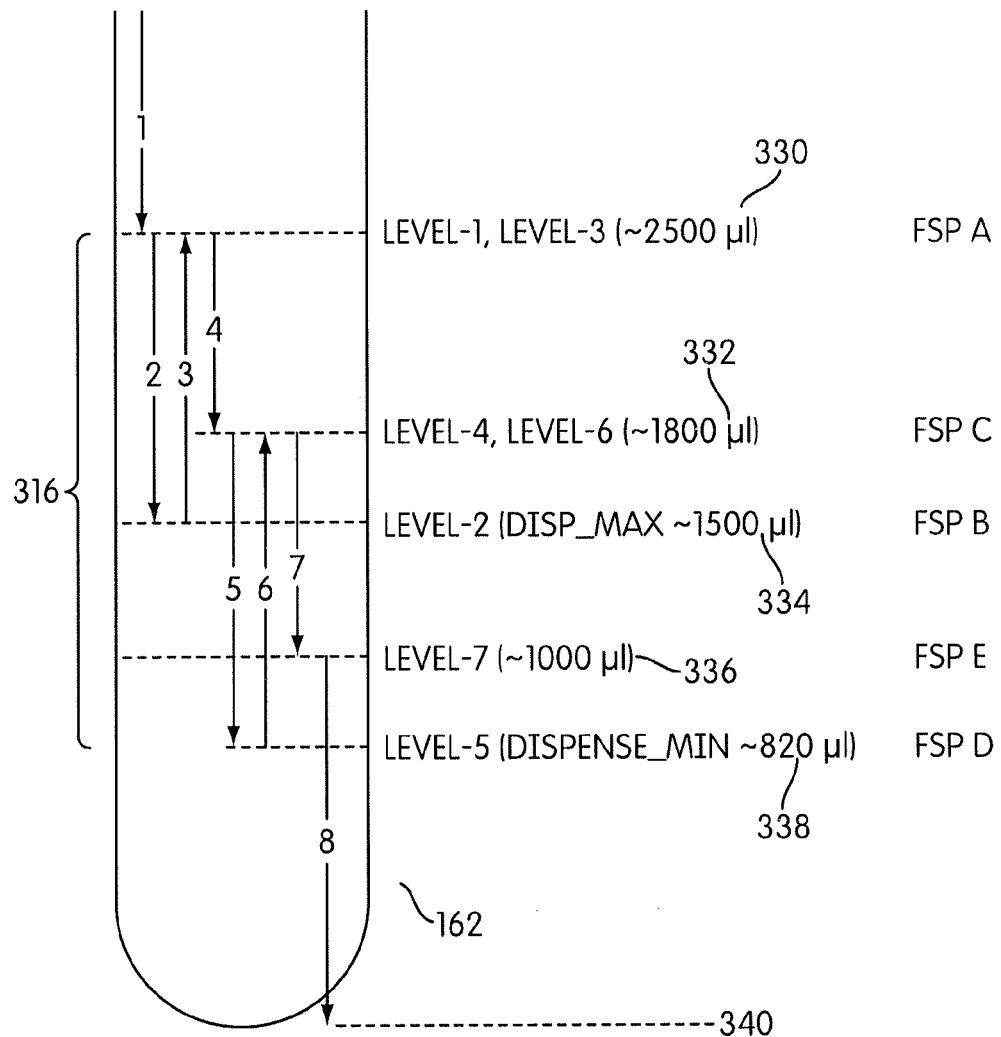
FIG. 23A is a representation of the exemplary receptacle and the sequence of preset heights at which the system analyzes capacitive signal to detect fluid.
Figures 1, 23B:
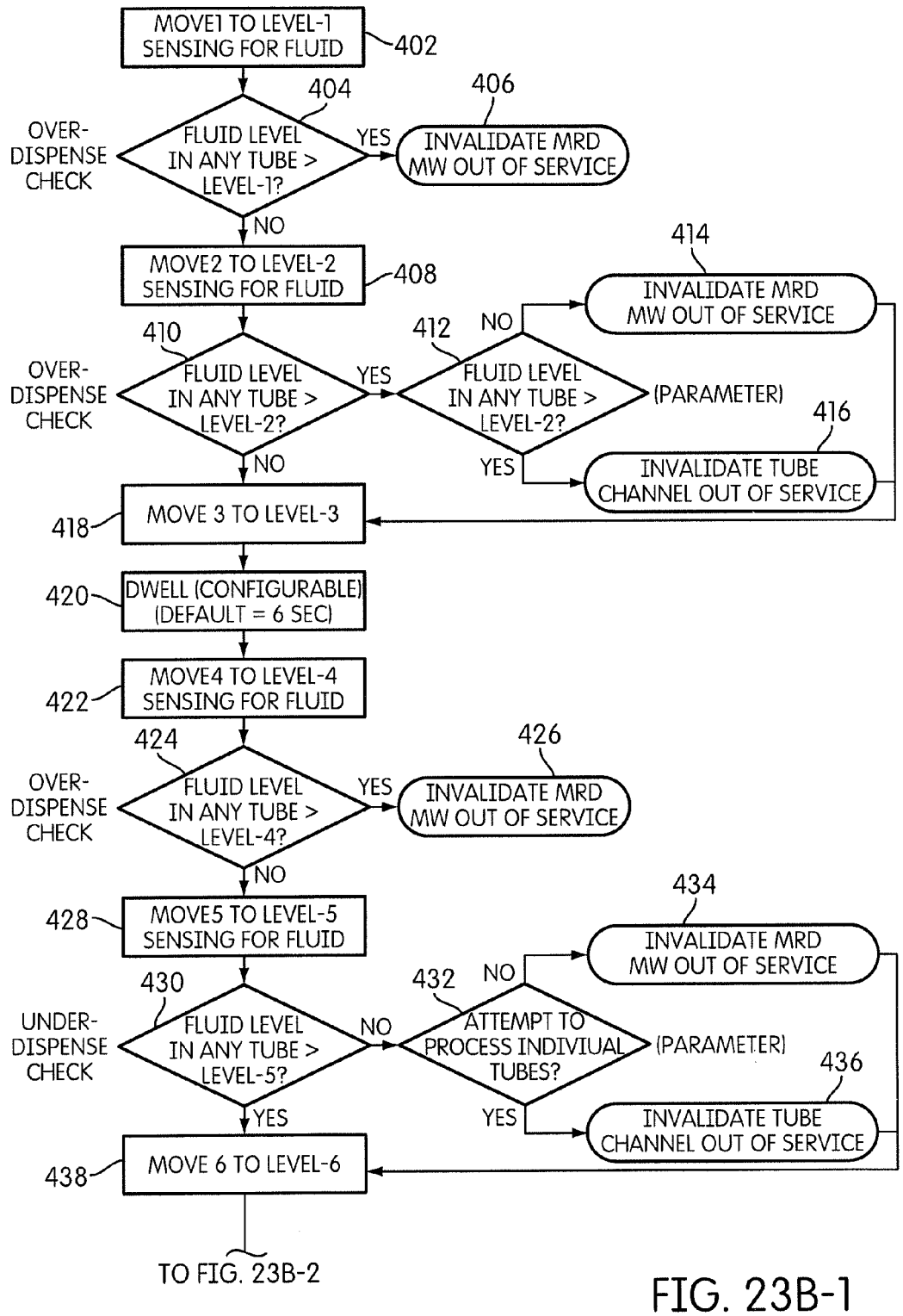
FIG. 1 is a perspective view of a receptacle in the form of a multiple receptacle device employed in combination with an apparatus embodying aspects of the present invention.
FIG. 23B is a flow chart detailing the process steps the device performs when attempting fluid detection in a receptacle.

As shown in FIG. 1, a receptacle in the form of a multiple receptacle device ("MRD") 160 comprises a plurality of individual receptacle vessels 162, preferably five. The receptacle vessels 162 of the MRD 160, preferably in the form of cylindrical tubes with open top ends and closed bottom ends, are connected to one another by a connecting rib structure 164 which defines a downwardly facing shoulder extending longitudinally along either side of the MRD 160.

Alternatively, the receptacle may comprise any container suitable for holding a fluid or liquid, including a cuvette, beaker, microtiter plate, or test tube. Unless explicitly stated, or the context dictates otherwise, the term "receptacle" will interchangeably refer to an entire MRD, one or more individual receptacle vessels of an MRD, a cuvette, beaker, microtiter plate, test tube, or any other suitable container. Similarly, unless explicitly stated or the context dictates otherwise, descriptions of the invention in the context of an MRD or receptacle vessel of an MRD are exemplary and should not be construed as limiting of the scope of the invention, as aspects of the invention are applicable to any suitable "receptacle."

The MRD 160 is preferably formed from injection molded polypropylene, such as those sold by Montell Polyolefins, of Wilmington, Del., product number PD701NW, Huntsman, product number P5M6K-048, or Flint Hills Resources.

An arcuate shield structure 169 is provided at one end of the MRD 160. An MRD manipulating structure 166 extends from the shield structure 169. The manipulating structure is adapted to be engaged by a transport mechanism for moving the MRD 160 between different components of a diagnostic analyzer. An exemplary transport mechanism that is compatible with the MRD 160 is described in U.S. Pat. No. 6,335,166 and in International Patent Application Publication No. WO 2010/132885, the disclosures of which are hereby incorporated by reference. MRD manipulating structure 166 comprises a laterally extending plate 168 extending from shield structure 169 with a vertically extending piece 167 on the opposite end of the plate 168. A gusset wall 165 extends downwardly from lateral plate 168 between shield structure 169 and vertical piece 167.

As shown in FIG. 3, the shield structure 169 and vertical piece 167 have mutually facing convex surfaces. The MRD 160 may be engaged by a transport mechanism and other components, by moving an engaging member laterally (in the direction "A") into the space between the shield structure 169 and the vertical piece 167. The convex surfaces of the shield structure 169 and vertical piece 167 provide for wider points of entry for an engaging member undergoing a lateral relative motion into the space.

A label-receiving structure 174 having a flat label-receiving surface 175 is provided on an end of the MRD 160 opposite the shield structure 169 and MRD manipulating structure 166. Human and/or machine-readable labels, such as scannable bar codes, can be placed on the surface 175 to provide identifying and instructional information on the MRD 160.

The MRD 160 preferably includes tip holding structures 176 adjacent the open mouth of each respective receptacle vessel 162. Each tip holding structure 176 provides a cylindrical orifice within which is received a conduit that is adapted to be placed onto the end of an aspirating tube, such as contact-limiting tip 170. The construction and function of the tip 170 will be described below. In one embodiment, each holding structure 176 is constructed and arranged to frictionally receive a tip 170 in a manner that prevents the tip 170 from falling out of the holding structure 176 when the MRD 160 is inverted, but permits the tip 170 to be removed from the holding structure 176 when engaged by a pipette.

Figures 2, 23B:
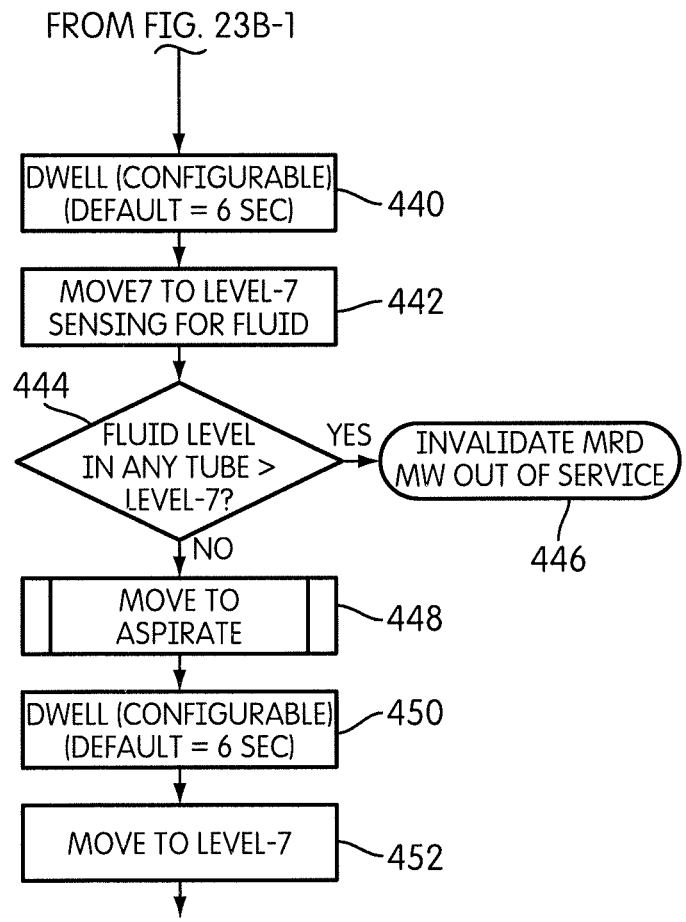
FIG. 2 is a side elevation of a contact-limiting pipette tip employed in combination with an instrument for performing a magnetic separation procedure and carried on the multiple receptacle device shown in FIG. 1.

As shown in FIG. 2, the tip 170 comprises a generally cylindrical structure having a peripheral rim flange 177 and an upper collar 178 of generally larger diameter than a lower portion 179 of the tip 170. The tip 170 is preferably formed from electrically conductive polypropylene. When the tip 170 is inserted into an orifice of a holding structure 176, the flange 177 contacts the top of structure 176 and the collar 178 provides a snug but releasable interference fit between the tip 170 and the holding structure 176. Alternatively, each holding structure 176 may be configured to loosely receive a tip 170 so that the tip is more easily removed from the holding structure when engaged by a pipette.

An axially extending through-hole 180 passes through the tip. Hole 180 includes an outwardly flared end 181 at the top of the tip 170 which facilitates insertion of a pipette tubular probe (not shown) into the tip 170. Two annular ridges 183 may be provided on the inner wall of hole 180. Ridges 183 provide an interference friction fit between the tip 170 and a tubular probe inserted into the tip 170.

The bottom end of the tip 170 preferably includes a beveled portion 182. When tip 170 is used on the end of an aspirator that is inserted to the bottom of a receptacle, such as a receptacle vessel 162 of an MRD 160, the beveled portion 182 prevents a vacuum from forming between the end of the tip 170 and the bottom of the receptacle.

Further details regarding the MRD 160 may be found in U.S. Pat. No. 6,086,827, the disclosure of which is hereby incorporated by reference.

Specimen Preparation Procedure

For nucleic acid tests, it may be necessary to lyse or permeabilize cells to first release a targeted nucleic acid and make it available for hybridization with a detection probe. See, e.g., Clark et al., "Method for Extracting Nucleic Acids from a Wide Range of Organisms," U.S. Pat. No. 5,786,208. The methods and systems of the present invention are not limited in their novel and useful implementation in any particular extraction procedure, thus any of a variety of extraction procedures are contemplated. For example, extraction procedures described in U.S. Pat. Nos. 7,267,950, 6,268,128, 5,945,515, 5,643,767, and 5,234,809, among others known or developed in the art, may be utilized. If the cells are lysed, the contents of the resulting lysate may include, in addition to nucleic acids, organelles, proteins (including enzymes such as proteases and nucleases), carbohydrates, and lipids, which may necessitate further purification of the nucleic acids. Additionally, for pathogenic organisms, chemical or thermal inactivation of the organisms may be desirable. Cells may be lysed or permeabilized by a variety of means well known to those skilled in the art, including by chemical, mechanical (e.g., sonication) and/or thermal means.

Various methods for capturing nucleic acids using magnetically-responsive solid supports are known in the art and can be employed in the present invention. These methods may be specific or non-specific for the targeted nucleic acid. One such method is Solid Phase Reversible Immobilization, which is based on the selective immobilization of nucleic acids onto magnetic microsolid support having carboxyl group-coated surfaces. See U.S. Pat. No. 5,705,628. In another method, magnetic particles having poly(dT) sequences derivatized thereon bind to capture probes having 5' poly(dA) tails and 3' target binding sequences. See U.S. Pat. No. 6,534,273. Still another approach is based on the ChargeSwitch® Technology, which is a magnetic bead-based technology that provides a switchable surface that is charge dependent on the surrounding buffer pH to facilitate nucleic acid purification (Invitrogen Corporation, Carlsbad, Calif.; Cat. No. CS12000). In low pH conditions, the ChargeSwitch® Magnetic Beads have a positive charge that binds the negatively charged nucleic acid backbone. Proteins and other contaminants that are not bound can be washed away. By raising the pH to 8.5, the charge on the surface is neutralized and the bound nucleic acids are eluted.

For approaches involving capture probes, the capture probes may be specific or non-specific for the targeted nucleic acids. A specific capture probe includes a target binding region that is selected to bind to a target nucleic acid under a predetermined set of conditions and not to non-target nucleic acids. A non-specific capture probe does not discriminate between target and non-target nucleic acids under the conditions of use. Wobble capture probes are an example of a non-specific capture probe and may include at least one random or non-random poly(K) sequence, where "K" can represent a guanine, thymine or uracil base. See U.S. Patent Application Publication No. US 2008-0286775 A1. In addition to hydrogen bonding with cytosine, its pyrimidine complement, guanine will also hydrogen bond with thymine and uracil. Each "K" may also represent a degenerate nucleoside such as inosine or nebularine, a universal base such as 3-nitropyrrole, 5-nitroindole or 4-methylindone, or a pyrimidine or purine base analog such as dP or dK. The poly(K) sequence of a wobble capture probe is of sufficient length to non-specifically bind the target nucleic acid, and is preferably 6 to 25 bases in length.

Sample material is prepared for a magnetic separation procedure by dispensing a specified amount of a target capture reagent into each sample-holding receptacle of a receptacle device. Dispensing may be performed manually or by an automated, robotic pipetting apparatus—into each of the receptacles 162 of the MRD 160. The target capture reagent includes a solid support material able to directly or indirectly bind to an analyte, such as through a capture probe, thereby immobilizing the analyte on the solid support comprises magnetically-responsive particles or beads. The amount dispensed into each receptacle 162 is typically in the range of 100-500 µL.

Magnetic Separation Wash Stations

In an exemplary implementation of a fluid transfer system incorporating the fluid level and tip detection methods and systems of the present invention, the system may be incorporated into a magnetic separation apparatus, or wash station, configured to perform a magnetic separation procedure for separating a target nucleic acid or other analyte from fluid specimen sample. An exemplary magnetic separation apparatus is described in U.S. Pat. No. 6,335,166, the disclosure of which is incorporated by reference, and incorporation of the methods and systems of the present invention into such a magnetic separation apparatus is described below. As previously noted, however, the methods and systems of the present invention are not limited in their novel and useful implementation to a magnetic separation apparatus but could be incorporated into any fluid transfer apparatus in which automated fluid level detection and/or detection of a protective tip are desired.

Figure 4:
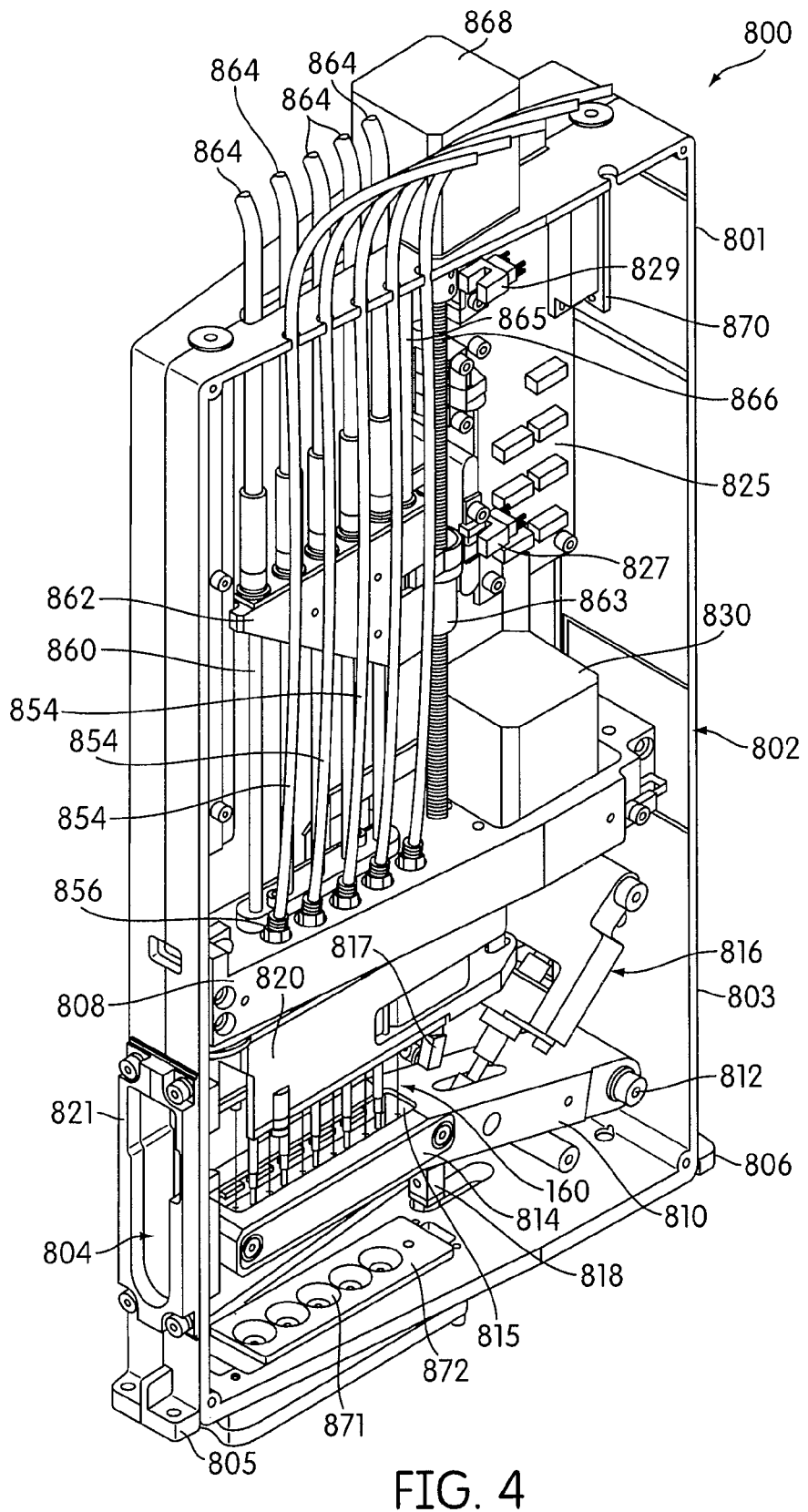
FIG. 4 is a perspective view of a magnetic separation wash station with a side plate thereof removed.
Figure 5:
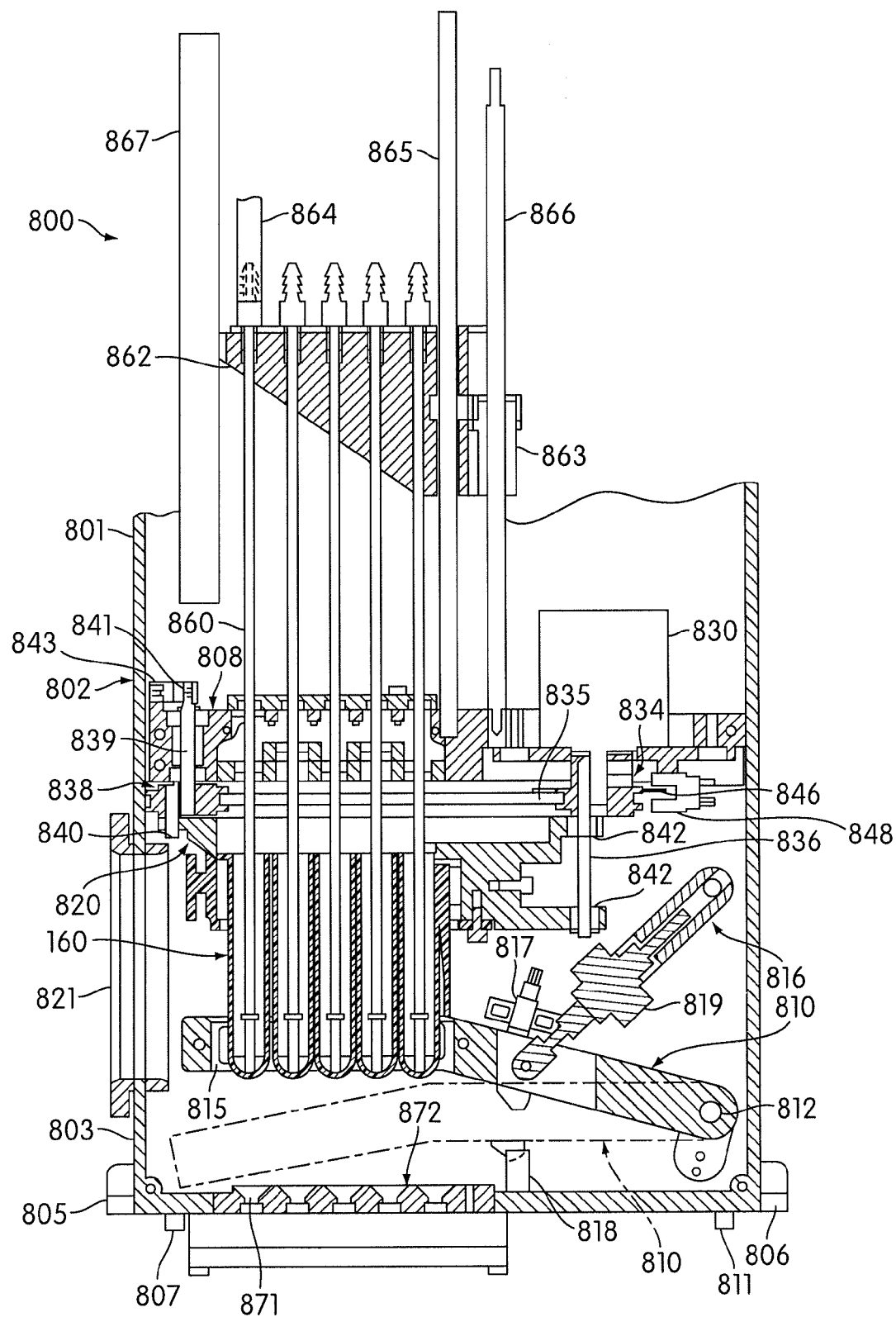
FIG. 5 is a partial transverse cross-section of the magnetic separation wash station.

Turning to FIGS. 4-5, a magnetic separation wash station 800 includes a module housing 802 having an upper section 801 and a lower section 803. Mounting flanges 805, 806 extend from the lower section 803 for mounting the magnetic separation wash station 800 to a support surface by means of suitable mechanical fasteners. Locator pins 807 and 811 extend from the bottom of lower section 803 of housing 802. Pins 807 and 811 register with apertures (not shown) formed in the support surface to help to locate the magnetic separation wash station 800 on the support surface before the housing 802 is secured by fasteners.

Cables bring power and control signals to the magnetic separation wash station 800, via one or more connectors (one such connector is shown at reference number 870). Monitoring and control of devices within the station 800, such as, for example, the various motors and sensors associated with the station, may be effected in whole or in part by an embedded controller, such as embedded controller 825, mounted within the upper housing 801 of the station 800. The embedded controller may communicate with a microprocessor controller of the diagnostic analyzer of which the magnetic separation wash station 800 is a part.

A loading slot 804 extends through the front wall of the lower section 803 to allow a transport mechanism (not shown) to place an MRD 160 into and remove an MRD 160 from the magnetic separation station 800. A tapered slot extension 821 may be provided around a portion of the loading slot 804 to facilitate MRD insertion through the slot 804. A midplate 808 separates the upper section 801 from the lower section 803.

Figure 7:
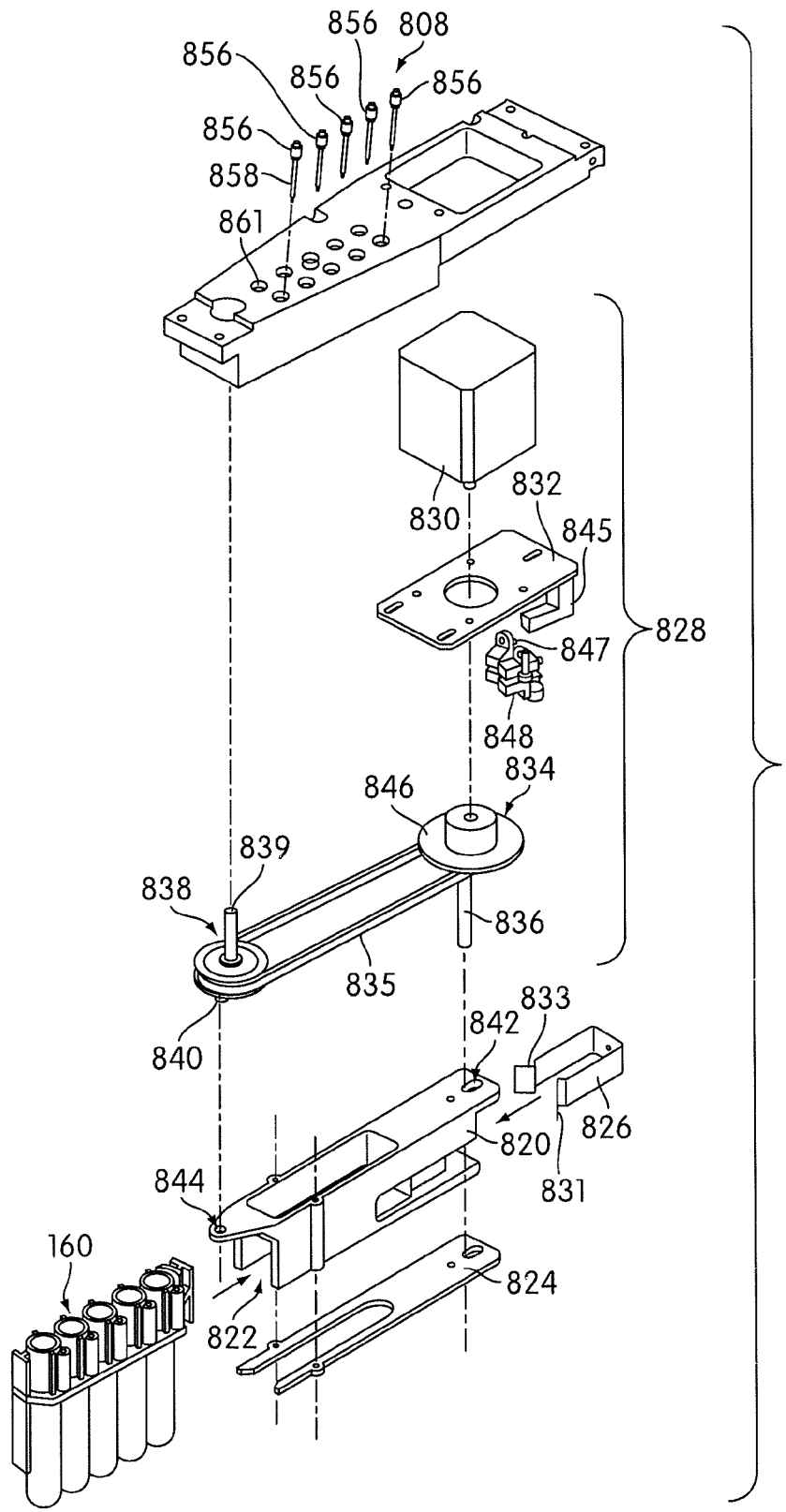
FIG. 7 is an exploded perspective view of a receptacle carrier unit, an orbital mixer assembly, and a midplate of the magnetic separation wash station.

An MRD carrier unit 820 is disposed adjacent the loading slot 804, below the midplate 808, for operatively supporting an MRD 160 disposed within the magnetic separation wash station 800. Turning to FIG. 7, the MRD carrier unit 820 has a slot 822 for receiving the upper end of an MRD 160. A lower fork plate 824 attaches to the bottom of the carrier unit 820 and supports the underside of the connecting rib structure 164 of the MRD 160 when slid into the carrier unit 820 (see FIGS. 8 and 9). A spring clip 826 is attached to the carrier unit 820 with its opposed prongs 831, 833 extending into the slot 822 to releasably hold the MRD within the carrier unit 820.

As an alternative to the arrangement shown in FIG. 7, the MRD carrier unit may comprise a single, injection molded part having an integrally formed ledge for supporting the MRD 160 and an integrally formed plastic spring element for retaining an MRD within the MRD carrier unit.

An orbital mixer assembly 828 is coupled to the carrier unit 820 for orbitally mixing the contents of an MRD held by the MRD carrier unit 820. The orbital mixer assembly 828 includes a stepper motor 830 controlled by the embedded controller 825 and mounted on a motor mounting plate 832, a drive pulley 834 having an eccentric pin 836, an idler pulley 838 having an eccentric pin 840, and a belt 835 connecting drive pulley 834 with idler pulley 838. Stepper motor 830 is preferably a VEXTA, model number PK245-02A, available from Oriental Motors Ltd. of Tokyo, Japan, and belt 835 is preferably a timing belt, model number A 6G16-170012, available from SDP/SI of New Hyde Park, N.Y. As shown in FIGS. 5 and 7, eccentric pin 836 fits within a slot 842 formed longitudinally in the MRD carrier unit 820. Eccentric pin 840 fits within a circular aperture 844 formed in the opposite end of MRD carrier unit 820. As the motor 830 turns the drive pulley 834, idler pulley 838 also rotates via belt 835 and the MRD carrier unit 820 is moved in a horizontal orbital path by the eccentric pins 836, 840 engaged with the apertures 842, 844, respectively, formed in the carrier unit 820. The rotation shaft 839 of the idler pulley 838 preferably extends upwardly and has a transverse slot 841 formed therethrough. An optical slotted sensor 843 in communication with the embedded controller 825 is disposed at the same level as the slot 841 and measures the frequency of the idler pulley 838 via the sensor beam intermittently directed through slot 841 as the shaft 839 rotates. Sensor 843 is preferably an Optek Technology, Inc., model number OPB980T11, sensor, available from Optek Technology, Inc. of Carrollton, Tex.

As an alternative to slot 841 and sensor 843, the frequency of idler pulley 838 may be measured by means of an encoder (not shown) in communication with the embedded controller 825 and mounted on the top of shaft 839.

Drive pulley 834 also includes a locator plate 846. Locator plate 846 passes through slotted optical sensors 847, 848 in communication with the embedded controller 825 and mounted to a sensor mounting bracket 845 extending from motor mounting plate 832. Sensors 847, 848 are preferably Optek Technology, Inc., model number OPB980T11, sensors, available from Optek Technology, Inc. of Carrollton, Tex. Locator plate 846 has a plurality of circumferentially spaced axial openings formed therein which register with one or both sensors 847, 848 to indicate a position of the orbital mixer assembly 828, and thus a position of the MRD carrier unit 820.

As an alternative to locator plate and sensors 847, 848, the frequency and position of drive pulley 834 may be measured by means of an encoder (not shown) in communication with the embedded controller 825 and coupled to the pulley 834.

A pivoting magnet moving apparatus 810 is attached inside the lower section 803 so as to be pivotable about point 812. The magnet moving apparatus 810 carries permanent magnets 814, which are positioned on either side of an MRD slot 815 formed in the magnet moving apparatus 810. The magnet moving apparatus 810, under the control of the embedded controller 825 and/or the microprocessor controller of the diagnostic analyzer, is constructed and arranged to move the magnets 814 between an operational position and a non-operational position with respect to an MRD 160 carried in the MRD carrier unit 820. In the operational position, the magnets 814 are disposed adjacent the MRD 160 and in sufficient proximity to the MRD so that the magnetically responsive particles within each receptacle vessel 162 are drawn out of suspension by the attraction of the magnetic fields of the magnets 814. In the non-operational position, the magnets are disposed at a sufficient distance from the receptacle vessel so as to have no substantial effect on the contents of each receptacle vessel. In the present context, "no substantial effect" means that the magnetically responsive particles are not drawn out of suspension by the attraction of the magnetic fields of the magnets 814.

Preferably five magnets, one corresponding to each individual receptacle vessel 162 of the MRD 160, are held in an aligned arrangement on each side of the magnet moving apparatus 810. The magnets are preferably made of neodymium-iron-boron (NdFeB), minimum grade n-35 and have preferred dimensions of 0.5 inch width, 0.3 inch height, and 0.3 inch depth. An electric actuator, generally represented at 816, pivots the magnet moving apparatus 810 up and down, thereby moving the magnets 814. As shown in FIG. 5, actuator 816 preferably comprises a rotary stepper motor 819 which rotates a drive screw mechanism coupled to the magnet moving apparatus 810 to selectively raise and lower the magnet moving apparatus 810. Motor 819 is preferably an HSI linear stepper actuator, model number 26841-05, available from Haydon Switch and Instrument, Inc. of Waterbury, Conn.

A sensor 818, preferably an optical slotted sensor, is in communication with the embedded controller 825 and is positioned inside the lower section 803 of the housing for indicating the down, or "home", or non-operational, position of the magnet moving apparatus 810. Sensor 818 is preferably an Optek Technology, Inc., model number OPB980T11, available from Optek Technology, Inc. of Carrollton, Tex. Another sensor 817, also preferably an Optek Technology, Inc., model number OPB980T11, optical slotted sensor, is preferably provided to indicate the up, or operational, position of the magnet moving apparatus 810.

The magnetic separation wash station 800 further includes a stripper plate 872 configured for stripping tips 170 off of the fluid transfer probes 860. The stripper plate 872 has a number of aligned stripping holes 871 corresponding in number to the number of fluid transfer probes 860, which is five in the preferred embodiment. Each stripping hole 871 has a keyhole configuration including a first portion, a second portion (the keyhole slot) that is smaller than first portion, and a bevel surrounding the perimeter of the stripping hole 871. The stripper plate 872 is oriented in the bottom of the housing 802 so that the small, second portion of each stripping hole 871 is generally aligned with each associated aspiration tube 860. After the MRD 160 is removed from the station 800, the fluid transfer probes 860 are lowered so that the tip 170 at the end of each probe 860 engages the stripping hole 871. The small portion of each stripping hole 871 is too small to accommodate the diameter of a tip 170, so the bevel surrounding the stripping hole 871 directs the tip 170 and the fluid transfer probe 860 toward the larger portion of the stripping hole 871, which is large enough for the tip 170 to pass therethrough. The fluid transfer probes 860 are made of an elastically flexible material, preferably stainless steel, so that, as the probes 860 continue to descend, the beveled portion of each stripping hole 871 causes each of probe 860 to deflect laterally. The small portion of each stripping hole 871 can accommodate the diameter of the aspirator tube 860, so that after the rim 177 of the tip 170 passes through the large portion of the stripping hole 871 and clears the bottom of stripper plate 872, each of the fluid transfer probes 860 snaps, due to its own resilience, into the small portion of the stripping hole 871. The fluid transfer probes 860 are then raised, and the rim 177 of each tip 170 engages the bottom peripheral edge of the small portion of the stripping hole 871. As the probes 860 ascend further, the tips 170 are pulled off the aspirator tubes 860 by the stripping holes 871. The stripped tips 170 are directed by a chute into a solid waste container.

Figure 10:
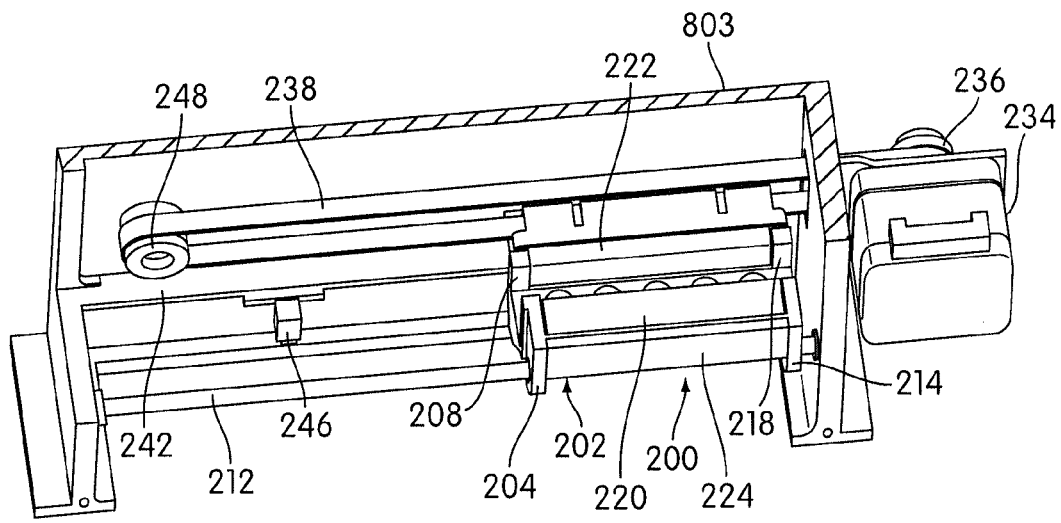
FIG. 10 is a top perspective view of a portion of a magnetic separation wash station illustrating an alternate embodiment of a magnet moving apparatus.
Figure 11:
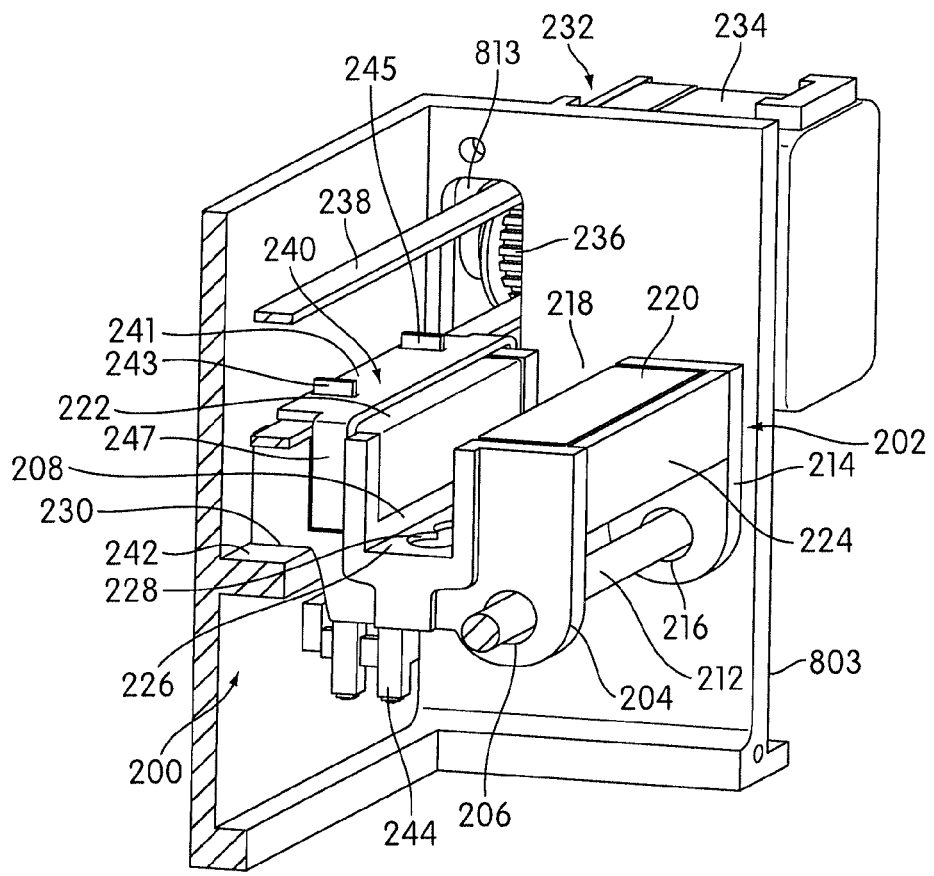
FIG. 11 is a partial perspective view the magnet moving apparatus of FIG. 10.

An alternate embodiment of a magnet moving apparatus for moving the magnets between operational and non-operational positions with respect to the MRD 160 is shown in FIGS. 10 and 11. The magnet moving apparatus comprises magnet slide 200 which comprises a magnet sled 202 that is moved along a linear path by a drive system 232 under the control of the embedded controller 825 and/or the microprocessor controller of the diagnostic analyzer.

More specifically, the magnet sled 202 includes a first wall 204 having a guide rod aperture 206 and a rectangular, U-shaped cutout 208. The magnet sled 202 further comprises a second wall 214 having a guide rod aperture 216 and a rectangular cutout 218 formed therein. A first magnet 220 is positioned between the first wall 204 and the second wall 214 on one side of the respective cutouts 208, 218 and is supported by a first magnet backing plate 224. Similarly, a second magnet 222 is disposed between the first wall 204 and the second wall 214 on an opposite side of the respective rectangular cutouts 208, 218 and is backed by a magnet backing plate (not shown). Magnets 220, 222 may be made from NdFeB, grade n-35 or grade n-40. As an alternative to single magnets 220, 222 on opposite sides of the magnet sled 202, five individual magnets may be provided on each side of the sled 202. In one embodiment, the sled includes five magnets on each side, each magnet having a size of approximately 12 mm×12 mm×8 mm and being made from NdFeB, grade n-40. The number of magnets corresponds to the number of receptacle vessels 162 comprising the MRD 160. Magnet sled 202 further includes a bottom plate 226 with a plurality of tip stripping elements, or tip removal structures, in the form of stripping openings 228 formed therein. Operation of the tip stripping openings 228 will be described below. Finally, the magnet sled 202 includes a guide surface formed in part by a straight laterally extended edge 230 formed in the first wall 204. A similar laterally extending straight edge is formed in the back wall 214. Any of the first and second walls 204, 214, first and second magnet backing plates 224, and bottom plate 226 may be integrally formed with each other. Suitable materials for the first and second walls 204, 214 and bottom plate 226 include non-magnetically responsive materials such as plastics and aluminum. Preferred material for the first and second magnet backing plates 224 include magnetically responsive materials, such as steel, to increase magnetic flux flowing through the magnets.

The drive system 232 comprises a drive motor 234 having a drive pulley 236 and mounted on the outside of the lower housing 803. Motor 234 may comprise a stepper motor under the control of the embedded controller 825 and/or the microprocessor controller of the diagnostic analyzer. A drive belt 238 is carried on the drive pulley 236 and an idler pulley 248 and extends through an opening 813 formed in the lower housing 803. Opposite ends 243, 245 of the drive belt 238 are attached to the magnet sled 202 by means of a coupling bracket 240. Suitable belts are available from Gates Corporation.

The coupling bracket 240 includes a top plate 241 disposed across the top of the second magnet 222 and having belt retaining slots within which opposite ends 243, 245 of the drive belt 238 are inserted and secured. A retainer tab 247 bent transversely with respect to the top plate 241 is positioned within a conforming slot formed in the first wall 204. A similar tab (not shown) is provided on the opposite end of the top plate 241 and extends within a conforming slot formed in the second wall 214 for securing the coupling bracket 240 to the magnet sled 202.

The magnet sled 202 is disposed inside the lower housing 803 with the guide surface 230 supported on a guide ledge 242 extending along an inner surface of the lower housing 803. The opposite side of the magnet sled 202 is supported by a guide rod 212 extending across the lower housing 803 and through the guide rod apertures 206 and 216. A bushing (not shown) may be provided at either or both of the guide rod apertures 206, 216 for securely and slideably supporting the magnet sled 202.

Rotation of the drive pulley 236 by the drive motor 234 turns the drive belt 238 to thereby move the magnet sled 202 between a non-operational position, such as shown in FIGS. 10 and 11, and an operational position whereby the magnet sled 202 is moved to the opposite side of the lower housing 803. When the magnet sled 202 is moved to the operational position, the lower ends of the receptacle vessels 162 of MRD 160 pass through the rectangular cutouts 208, 218 of the first wall 204 and second wall 214, respectively, so as to be disposed between the first magnet 220 and the second magnet 222.

A retracted position sensor 244 is mounted to an inner surface of the lower housing 803 indicates when the magnet sled 202 is in a retracted, or non-operational, position. Similarly, an extended position sensor 246, also mounted to an inner surface of the lower housing 803, indicates when the magnet sled 202 is in an extended, or operational, position. Sensors 244 and 246 are in communication with the embedded controller 825 and may comprise slotted optical sensors which detect the presence of a tab (not shown) projecting from a lower portion of the magnet slide 202.

Figure 12:
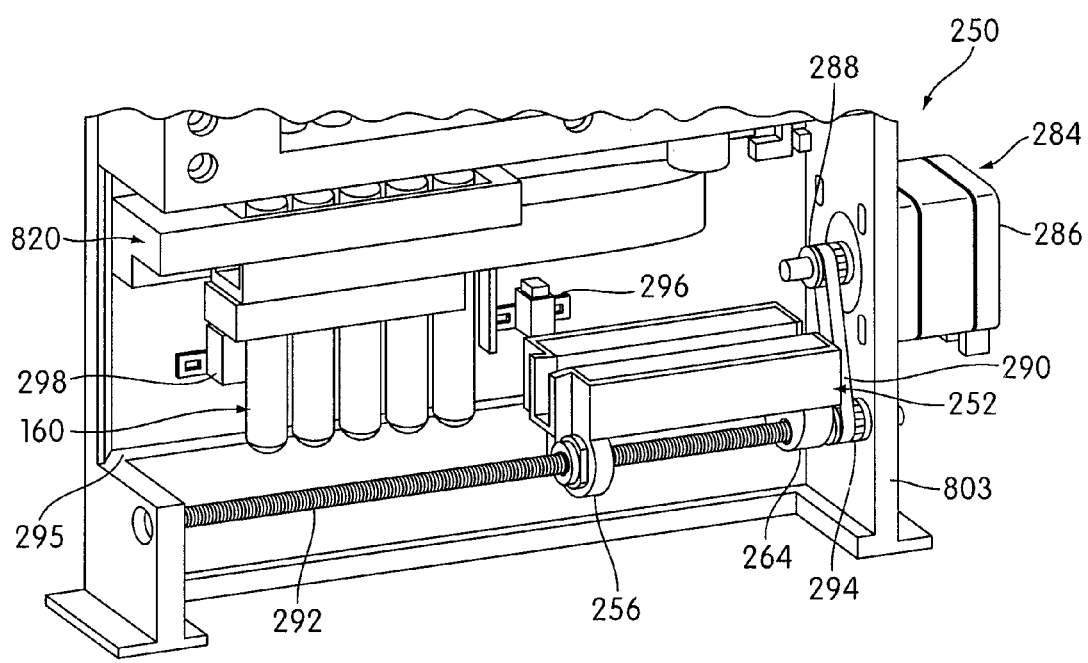
FIG. 12 is a partial perspective view of a magnetic separation wash station illustrating a further alternate embodiment of a magnet moving apparatus.
Figure 13:
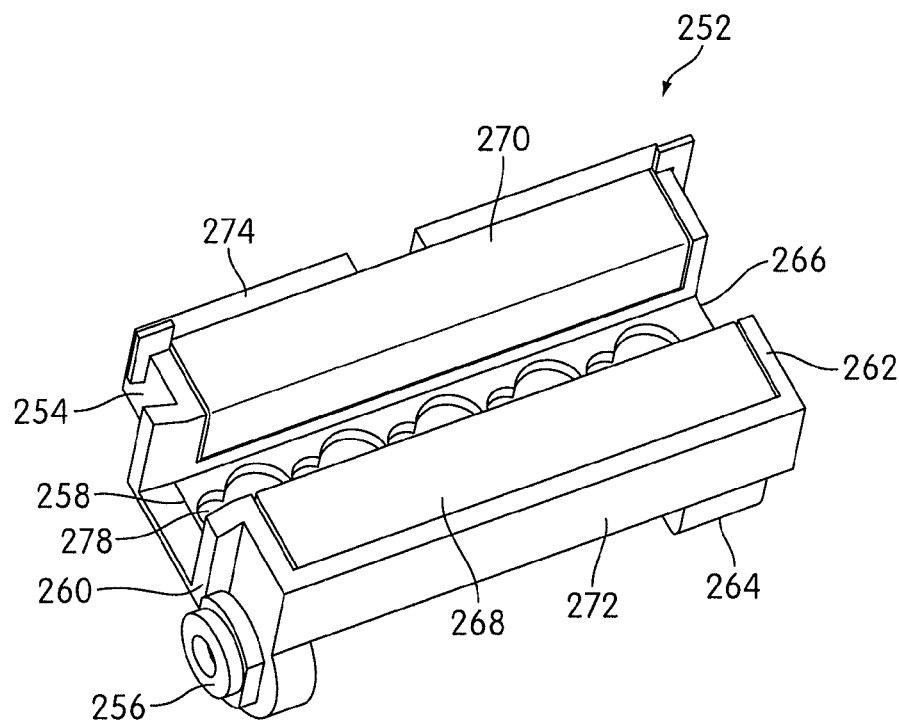
FIG. 13 is a top perspective view of a magnet sled of the magnet moving apparatus of FIG. 12.
Figure 14:
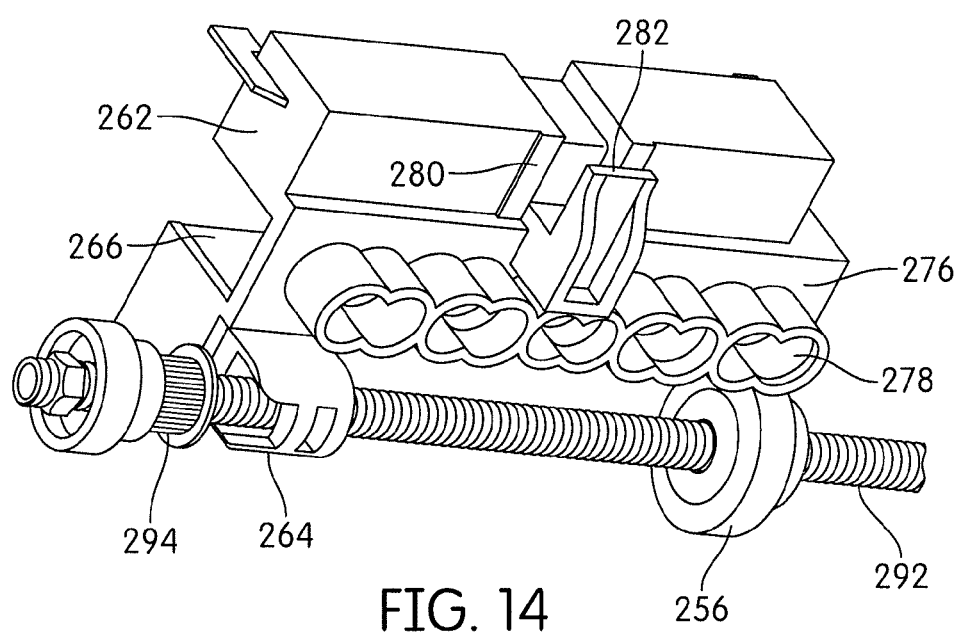
FIG. 14 is a bottom perspective view of the magnet sled of FIG. 13.

A further alternative embodiment of a magnet moving apparatus is shown in FIGS. 12-15. The magnet moving apparatus of FIGS. 12-15 comprises a magnet slide 250 including a magnet sled 252 and a drive system 284, under the control of the embedded controller 825 and/or the microprocessor controller of the diagnostic analyzer, which moves the magnet sled 252 between a non-operational position (as shown in FIG. 12) and an operational position with respect to an MRD 160.

More specifically, the magnet sled 252 comprises a first wall 254 including a screw follower 256 and a rectangular opening 258. An extended flange 260 may be provided around the rectangular opening 258. The magnet sled 252 further comprises a second wall 262 having a guide bushing 264 and a rectangular opening 266. A first magnet 268 is disposed between the first wall 254 and the second wall 262 and is supported by a first magnet backing plate 272. Similarly, a second magnet 270 is disposed between the first wall 254 and the second wall 262 on an opposite side of the rectangular openings 258, 266 and is supported by a second magnet backing plate 274. Again, as an alternative to single magnets 268, 270 on opposite sides of the magnet sled 252, five individual magnets having a size of approximately 12 mm×12 mm×8 mm and made from NdFeB, grade n-40 can be provided on each side of the sled 252.

The magnet sled 252 further includes a bottom plate 276 in which a plurality of tip stripping openings 278 are formed, a guide surface 280, and a retainer bracket 282. Guide surface 280 may comprise two surfaces disposed on opposite sides of the retainer bracket 282.

A drive system 284 includes a drive motor 286, which may comprise a stepper motor, under the control of the embedded controller 825 and/or the microprocessor controller of the diagnostic analyzer, mounted on the exterior of the lower housing 803 and having a drive pulley 288. A threaded drive screw 292 extends across the lower housing 803 and is journaled at its opposite ends to the lower housing wall so as to be rotatable about its longitudinal axis. Threaded drive screw 292 further includes a pulley 294 located at one end thereof. The threaded drive screw 292 is operatively coupled to the drive motor 286 by means of a drive belt 290 carried on the drive pulley 288 of the drive motor 286 and the pulley 294 of the threaded drive screw 292.

The threaded drive screw 292 extends through the screw follower 256 of the first wall 254 and the guide bushing 264 of the second wall 262. The guide surface 280 on the bottom surface of the magnet sled 252 and located on the opposite side of the sled 252 from the screw follower 256 and guide bushing 264 slidably rests on a guide flange 295 extending along an inner wall of the lower housing 803. A lower portion of the retainer bracket 282 extends beneath the guide flange 295 so that the guide flange is disposed between the guide surface 280 and the retainer bracket 282.

Rotation of the drive pulley 288 by the drive motor 286 is transferred to the threaded drive screw 292 by means of the drive belt 290. The rotating drive screw 292 engaged with the screw follower 256 causes linear translation of the magnet sled 252 in a longitudinal direction with respect to the drive screw 292. Rotation of the drive screw 292 in one direction will cause left to right translation of the magnet sled 252, and rotation of the screw 292 in the opposite direction will cause right to left translation of the magnet sled 252. The retainer bracket 282 engaged with the underside of the guide flange 295 prevents the magnet sled 252 from tipping out of contact with the guide flange 295 due to friction between the drive screw 292 and the screw follower 256.

When the magnet sled 252 is moved from the non-operational position, shown in FIG. 12, to an operational position, the MRD 160 passes through the rectangular openings 258, 266 and is disposed between the first magnet 268 and second magnet 270. The extended flange 260 formed around the rectangular opening 258 of the 254 is provided to assist in guiding the MRD 160 through the opening 258.

A retracted position sensor 296 mounted to the inner wall of the lower housing 803 indicates when the magnet sled 252 is in a retracted, or non-operational, position, and an extended position sensor 298, also mounted to the inner wall of the lower housing 803, indicates when the magnet sled 252 is in an extended, or operational, position with respect to the MRD. Sensors 296 and 298 are in communication with the embedded controller 825 and may comprise optical sensors which detect the presence of a tab extending from a portion of the magnet sled 252.

Returning to FIG. 4, wash buffer solution delivery tubes 854 connect to fittings 856 and extend through a top surface of the module housing 802. Wash buffer delivery tubes 854 extend through the midplate 808 via fittings 856, to form a wash buffer delivery network.

Figure 8:
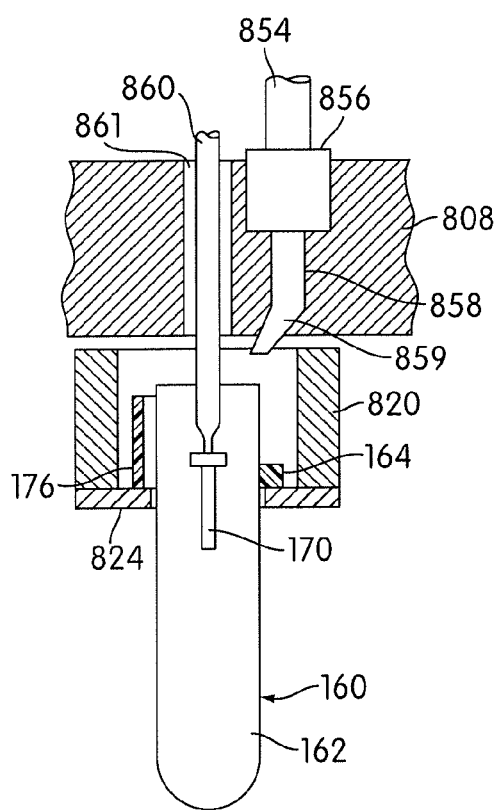
FIG. 8 is a partial cross-sectional view of a wash buffer dispenser nozzle, a fluid transfer probe with a contamination-limiting tip engaged with an end thereof, and a receptacle carrier unit of the magnetic separation wash station, showing a multiple receptacle device carried in the receptacle carrier unit and the fluid transfer probe and contamination-limiting tip inserted into a receptacle vessel of the multiple receptacle device.
Figure 9:
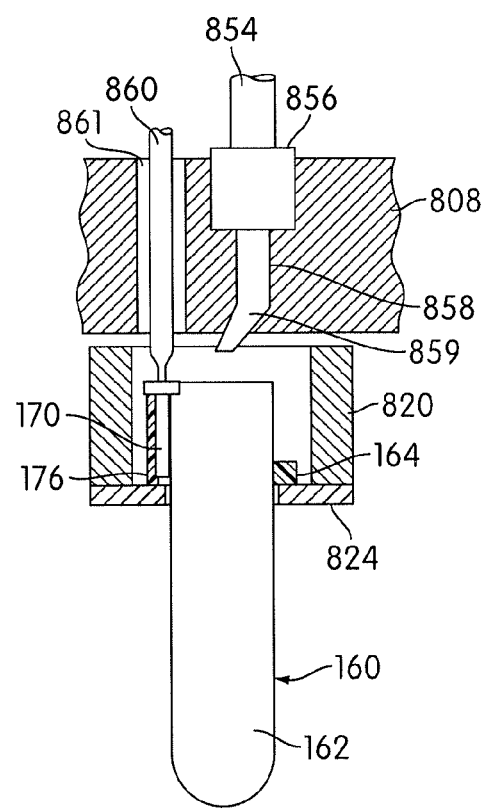
FIG. 9 is a partial cross-sectional view of the wash buffer dispenser nozzle, the fluid transfer probe, and the receptacle carrier unit of the magnetic separation wash station, showing the multiple receptacle device carried in the receptacle carrier unit and the fluid transfer probe engaging the contamination-limiting tip held in a contamination-limiting element holding structure of the multiple receptacle device.

As shown in FIGS. 8 and 9, wash buffer dispenser nozzles 858 extending from the fittings 856 are disposed within the midplate 808. Each nozzle is located above a respective receptacle vessel 162 of the MRD 160 at a laterally off-center position with respect to the receptacle vessel 162. Each nozzle includes a laterally-directed lower portion 859 for directing the wash buffer into the respective receptacle vessel from the off-center position. Dispensing fluids into the receptacle vessels 162 in a direction having a lateral component can limit splashing as the fluid runs down the sides of the respective receptacle vessels 162. In addition, the laterally directed fluid can rinse away materials clinging to the sides of the respective receptacle vessels 162.

As shown in FIGS. 4 and 5, fluid transfer probes, or aspirator tubes, 860 extend through a tube holder 862, to which the tubes 860 are fixedly secured, and extend through openings 861 in the midplate 808. Fluid transfer tubing 864 connected to the fluid transfer probes 860 extend to a vacuum pump (not shown), with aspirated fluid drawn off into a fluid waste container carried (not shown). Each of the fluid transfer probes 860 has a preferred length of 12 inches with an inside diameter of 0.041 inches.

The tube holder 862 is attached to a drive screw 866 actuated by a lift motor 868. Lift motor 868 is preferably a stepper motor, such as a VEXTA, model number PK245-02A, available from Oriental Motors Ltd. of Tokyo, Japan, and the drive screw 866 is preferably a ZBX series threaded anti-backlash lead screw, available from Kerk Motion Products, Inc. of Hollis, N.H. Lift motor 868 is under the control of the embedded controller 825 and/or the microprocessor controller of the diagnostic analyzer. In the illustrated embodiment, the tube holder 862 is attached to a threaded sleeve 863 of the drive screw 866. Rod 865 and slide rail 867 function as a guide for the tube holder 862. Alternatively, a linear bearing (not shown) may be employed as a guide for the tube holder 862.

Z-axis sensors 829, 827 (slotted optical sensors) communicate with the embedded controller 825 and cooperate with a tab extending from the tube holder 862 and/or the threaded sleeve 863 to indicate top and bottom of stroke positions of the fluid transfer probes 860. The Z-axis sensors are preferably Optek Technology, Inc., model number OPB980T11, sensors, available from Optek Technology, Inc. of Carrollton, Tex. In another embodiment, only one Z-axis sensor (829 or 827) and the Z axis position of the tube holder 862, and thus the tubes 860, can be ascertained, for example, by counting steps of the motor 868 relative to a known position, such as the position of sensor 827 or 829.

The magnet moving apparatus 810, 200, 250 is initially in a non-operational position (e.g., as shown in phantom in FIG. 5 and in FIGS. 10 and 12), as verified by the retracted position sensor 818, 244, 296, when the MRD 160 is inserted into the magnetic separation wash station 800 through the insert opening 804 and into the MRD carrier unit 820. When the magnet moving apparatus is in the non-operational position, the magnetic fields of the magnets will have no substantial effect on the magnetically responsive particles contained in the MRD 160. The orbital mixer assembly 828, under the control of the embedded controller 825 and/or the microprocessor controller of the diagnostic analyzer, moves the MRD carrier unit 820 a portion of a complete orbit so as to move the carrier unit 820 and MRD 160 laterally, so that each of the tips 170 carried by the tip holding structures 176 of the MRD 160 is aligned with each of the aspiration tubes 860, as shown in FIG. 9. The position of the MRD carrier unit 820 is verified, for example, by the locator plate 846 and one of the sensors 847, 848. Alternatively, the stepper motor 830 can be moved a known number of steps to place the MRD carrier unit 820 in the desired position, and one of the sensors 847, 848 can be omitted. Note that magnet moving apparatus cannot move to an operational position when the MRD carrier unit 820 has been moved to this tip engagement position because the MRD carried by unit 82 will interfere with movement of the magnet moving apparatus.

The tube holder 862 and fluid transfer probes 860 are lowered by the lift motor 868 and drive screw 866 until each of the fluid transfer probes 860 frictionally engages a conduit, e.g., a tip 170, held in an associated carrying structure 176 on the MRD 160. The tube holder 862, the lift motor 868, and drive screw 866, together with the Z-axis sensors 829, 827 and the embedded controller 825 and/or the microprocessor controller of the diagnostic analyzer, comprise components of an embodiment of a probe control module.

Figure 6:
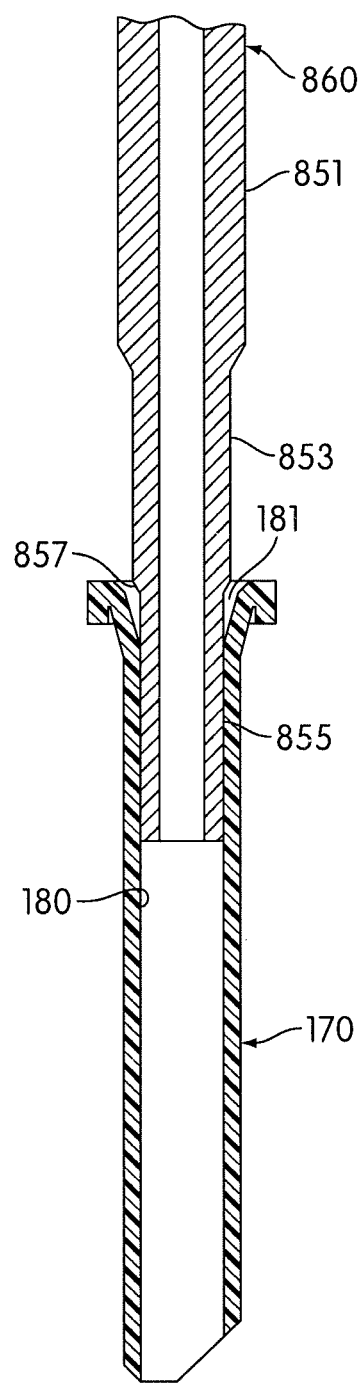
FIG. 6 is a partial transverse cross-section of a tip of an aspirating tube of the magnetic separation wash station with a contamination-limiting tip carried on the end thereof.

As shown in FIG. 6, the lower end of each fluid transfer probe 860 is characterized by a tapering, step construction, whereby the tube 860 has a first portion 851 along most of the extent of the tube, a second portion 853 having a diameter smaller than that of the first portion 851, and a third portion 855 having a diameter smaller than that of the second portion 853. The diameter of the third portion 855 is such as to permit the end of the tube 860 to be inserted into the flared portion 181 of the through hole 180 of the tip 170 and to create an interference friction fit between the outer surface of third portion 855 and a portion of the inner wall of the through hole 180, such as the two annular ridges 183 (see FIG. 2) or alternatively, longitudinally-oriented ridges (not shown), that line the inner wall of hole 180 of tip 170. An annular shoulder 857 is defined at the transition between second portion 853 and third portion 855. The shoulder 857 limits the extent to which the tube 860 can be inserted into the tip 170, so that the tip can be stripped off after use, as will be described below.

The tips 170 may be at least partially electrically conductive, so that the presence of a tip 170 on a fluid transfer probe 860 can be verified by the capacitance of a capacitor comprising a group of components, including the fluid transfer probes 860 and tips 170 as one half of the capacitor and the surrounding hardware of the magnetic separation wash station 800 (e.g., the metal midplate 808) as the other half of the capacitor. Details of a system and method for capacitively detecting the presence—and absence—of a tip at the distal end of each fluid transfer probe 860 is described below.

After successful conduit engagement, the orbital mixer assembly 828 moves the MRD carrier unit 820 back to a fluid transfer position shown in FIG. 8 as verified by the locator plate 846 and one or both of the sensors 847, 848.

The magnet moving apparatus 810, 200, 250 is then moved to the operational position (e.g., as shown in FIG. 4) so that the magnets are disposed adjacent opposite sides of the MRD 160. With the contents of the MRD subjected to the magnetic fields of the magnets, the magnetically responsive particles bound indirectly to the target nucleic acids will be drawn to the sides of the individual receptacle vessels 162 adjacent the magnets. The remaining material within the receptacle vessels 162 should be substantially unaffected, thereby isolating the target nucleic acids. The magnet moving apparatus will remain in the operational position for an appropriate dwell time, as defined by the assay protocol and controlled by the assay manager program, to cause the magnetic particles to adhere to the sides of the respective receptacle vessels 162. In one embodiment, the distance between the opposed magnets on opposite sides of the magnet moving apparatus is about 12.4 mm and the diameter of each receptacle 162 of MRD 160 is 11.4 mm, which means there is a gap of 0-1 mm between the magnet and the side of the receptacle 162 when the magnet moving apparatus is in the operational position. When the magnet moving apparatus is moved to the non-operational position, there is a clearance of at least 30 mm between the magnets and the receptacles 160.

The fluid transfer probes 860 are then lowered into the receptacle vessels 162 of the MRD 160 to aspirate the fluid contents of the individual receptacle vessels 162, while the magnetic particles remain in the receptacle vessels 162, adhering to the sides thereof, adjacent the magnets. The tips 170 at the ends of the fluid transfer probes 860 ensure that the contents of each receptacle vessel 162 do not come into contact with the sides of the fluid transfer probes 860 during the aspirating procedure. Because the tips 170 will be discarded before a subsequent MRD is processed in the magnetic separation wash station 800, the chance of cross-contamination by the fluid transfer probes 860 is minimized.

The electrically conductive tips 170 can be used in a known manner for capacitive fluid level sensing within the receptacle vessels 162 of the MRDs. The fluid transfer probes 860 and the conductive tips 170 comprise one half of a capacitor, the surrounding conductive structure within the magnetic separation wash station comprises the second half of the capacitor, and the fluid medium between the two halves of the capacitor constitutes the dielectric. Capacitance changes due to a change in the nature of the dielectric can be detected.

The capacitive circuitry of the fluid transfer probes 860 can be arranged so that all five fluid transfer probes 860 operate as a single gang level-sensing mechanism. When any of the fluid transfer probes 860 and its associated tip 170 contacts fluid material within a receptacle vessel, capacitance of the system changes due to the change in the dielectric. If the Z-position of the fluid transfer probes 860 at which the capacitance change occurs is too high, then a high fluid level in at least one receptacle vessel is indicated, thus implying an aspiration failure or overdispense. On the other hand, if the Z-position of a fluid transfer probe at which the capacitance change occurs is correct, but one or more of the other tubes has not yet contacted the top of the fluid due to a low fluid level, a low fluid level will be indicated.

Alternatively, the fluid transfer probe capacitive circuitry can be arranged so that each of the five fluid transfer probes 860 operates as an individual level sensing mechanism.

With five individual level sensing mechanisms, the capacitive level sensing circuitry can detect failed fluid aspiration in one or more of the receptacle vessels 162 if the fluid level in one or more of the receptacle vessels is high. Individual capacitive level sensing circuitry can detect failed fluid dispensing into one or more of the receptacle vessels 162 if the fluid level in one or more of the receptacle vessels is low. Furthermore, the capacitive level sensing circuitry can be used for volume verification to determine if the volume in each receptacle vessel 162 is within a prescribed range. Volume verification can be performed by stopping the descent of the fluid transfer probes 860 at a position above expected fluid levels, e.g. 110% of expected fluid levels, to make sure none of the receptacle vessels has a level that high, and then stopping the descent of the fluid transfer probes 860 at a position below the expected fluid levels, e.g. 90% of expected fluid levels, to make sure that each of the receptacle vessels has a fluid level at least that high.

Further details of a system and method for using a capacitive proximity sensor system for detecting the fluid level within a receptacle are described below.

Following aspiration, the fluid transfer probes 860 are raised, the magnet moving apparatus moves to the non-operational position, the MRD carrier unit 820 is moved to the fluid dispense position (FIG. 9), and a prescribed volume of wash buffer is dispensed into each receptacle vessel 162 of the MRD 160 through the wash buffer dispenser nozzles 858. To prevent hanging drops of wash buffer on the wash buffer dispenser nozzles 858, a brief, post-dispensing air aspiration is preferred.

The orbital mixer assembly 828 then moves the MRD carriers 820 in a horizontal orbital path at high frequency to mix the contents of the MRD 160. Mixing by moving, or agitating, the MRD in a horizontal plane is preferred so as to avoid splashing the fluid contents of the MRD and to avoid the creation of aerosols. Following mixing, the orbital mixer assembly 828 stops the MRD carrier unit 820 at the fluid transfer position.

To further purify the targeted nucleic acids, the magnet moving apparatus 810, 200, 250 is again moved to the operational position and maintained in the operational position for a prescribed dwell period. After magnetic dwell, the fluid transfer probes 860 with the engaged tips 170 are lowered to the bottoms of the receptacle vessels 162 of the MRD 160 to aspirate the test specimen fluid and wash buffer in an aspiration procedure essentially the same as that described above.

One or more additional wash cycles, each comprising a dispense, mix, magnetic dwell, and aspirate sequence, may be performed as defined by the assay protocol. Those skilled in the art of nucleic acid-based diagnostic testing will be able to determine the appropriate magnetic dwell times, number of wash cycles, wash buffers, etc. for a desired target capture procedure.

Multiple magnetic separation wash stations 800 can be employed in a diagnostic analyzer to permit separation wash procedure to be performed on multiple MRDs in parallel. The number of magnetic separation wash stations 800 will vary depending on the desired throughput of the analyzer.

After the final wash step, the magnet moving apparatus 810, 200, 250 is moved to the non-operational position, and the MRD 160 is removed from the magnetic separation wash station 800 by a transport mechanism. Prior to removing the MRD from the station 800, and preferably prior to magnet retraction, a final residual volume check may be performed by lowering the fluid transfer probes 860 and tips 170 to a position just above the bottom of each receptacle vessel 162 to determine if any excess fluid volume remains in the vessel 162.

After the MRD 160 is removed from the wash station, the tips 170 are stripped from the aspiration tubes 860 by the tip stripping openings 228, 278.

Figure 15:
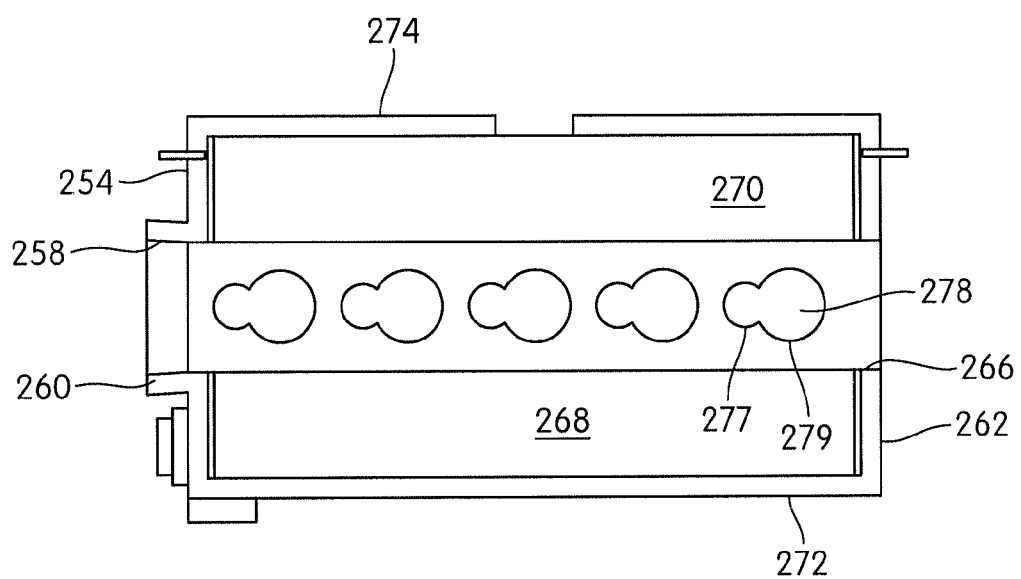
FIG. 15 is a top view of the magnet sled of FIGS. 13 and 14.

The magnet sled 202 of the magnet slide 200 shown in FIG. 10 and the magnet sled 252 of the magnet slide 250 shown in FIG. 12 both include tip stripping openings 228, 278, respectively, formed along a central portion of a lower surface thereof between the first and second magnets. The tip stripping openings, as shown in FIG. 15, comprise keyhole shape openings having a first portion 279 and a second portion 277, with the first portion 279 being larger than the second portion 277. The number of tip stripping openings is equal to the number of aspirating tubes 860, which, in the illustrated embodiment, is five.

To strip the conduits, or tips 170, off of each of the aspirating tubes 860, the magnet sled 202, 252 is positioned beneath the aspirating tubes 860 so that the larger portions 279 of the tip stripping openings 278 are aligned with each of the aspirating tubes 860. The aspirating tubes 860, with the tips 170 disposed thereon, are lowered through the first portions 279 of the stripping openings, which are large enough to permit the tips 170 to pass therethrough. After the tips 170 have passed through the tip stripping openings, the magnet sled is moved slightly so that the aspirating tubes 860 are disposed within the second, smaller portions 277 of the stripping openings, which are large enough to accommodate the aspirating tubes 860, but are smaller than the outside diameter of the rim flange 177 of the tips 170. The aspirating tubes 860 are then raised, and the tips 170 engage the peripheral edges surrounding the second portion 277 of the stripping openings, thereby pulling the tips 170 off of the aspirating tubes 860 as the aspirating tubes ascend. Preferably, the tip stripping openings are disposed at staggered vertical locations so that as the aspirating tubes 860 are raised in unison, the tips 170 encounter the peripheral edges of the stripping openings in a staggered manner. For example, each stripping opening may be at a different vertical position, so that as the fluid transfer probes 860 are moved with respect to the stripping openings, the tips 170 are sequentially removed from the associated fluid transfer probes 860 one at a time.

Sensing Fluid Surface and Tip Presence by Capacitance

Details of a system and method for using capacitance to sense both fluid level within a receptacle 162 and the presence (or absence) of a tip 170 at the distal end of fluid transfer probe, such as fluid transfer probe 860, will now be described.

The magnetic separation wash station 800 can be used to immobilize target nucleic acid and separate the immobilized nucleic acid from non-hybridized nucleic acid through various wash steps. To ensure safety from cross-contamination, the presence of the tip 170 on the probe 860 must be confirmed after the tip engagement step and prior to any fluid transfer, and removal of the used tip must be confirmed after the tip-stripping step. Any errors in fluid dispense, such as under-dispense, over-dispense, or failed transfer of fluids into or out of the reaction receptacle 162, can result in a failed magnetic separation wash procedure. Thus the fluid level within each receptacle 162 must be ascertained at predetermined times to ensure that the fluids have been properly aspirated from or dispensed into the receptacle 162. To accomplish this, for each fluid transfer sequence during the magnetic separation wash procedure, three sensing, or detecting, processes are performed. First, the "tip pick" action of a fluid transfer probe 860 attaching a tip 170 at the distal end must be verified. Second, fluid levels in the reaction receptacle 162 are verified at predetermined times during the magnetic separation wash procedure. And, third, following, the "tip strip" action, absence of the tip 170 at the distal end of the probe 860 must be verified. These sensing processes, performed using a capacitive proximity sensor system in accordance with aspects of the present invention, are described below.

There are different ways to implement a capacitive sensing functionality. One method is to place an unknown capacitance into a circuit controlling the frequency of an oscillator and then measure the oscillator frequency to determine capacitance. Another method, exemplified by an embodiment of the present invention, is to utilize a capacitive voltage divider (CVD) as described herein, and to use the changes in capacitance of the overall capacitive detection system, which changes the impedance of the CVD and thus the output signal, as indications of status changes for the fluid transfer probe 860. In accordance with aspects of the present invention, the capacitive proximity sensor system is used for two different sensing functions: one is liquid level detection and the other is tip 170 presence sensing. Measurement and analysis of waveforms of a capacitive signal determine when the fluid transfer probe 860 is in contact with fluid or when the fluid transfer probe 860 has a tip attached at its distal end.

Figure 16:
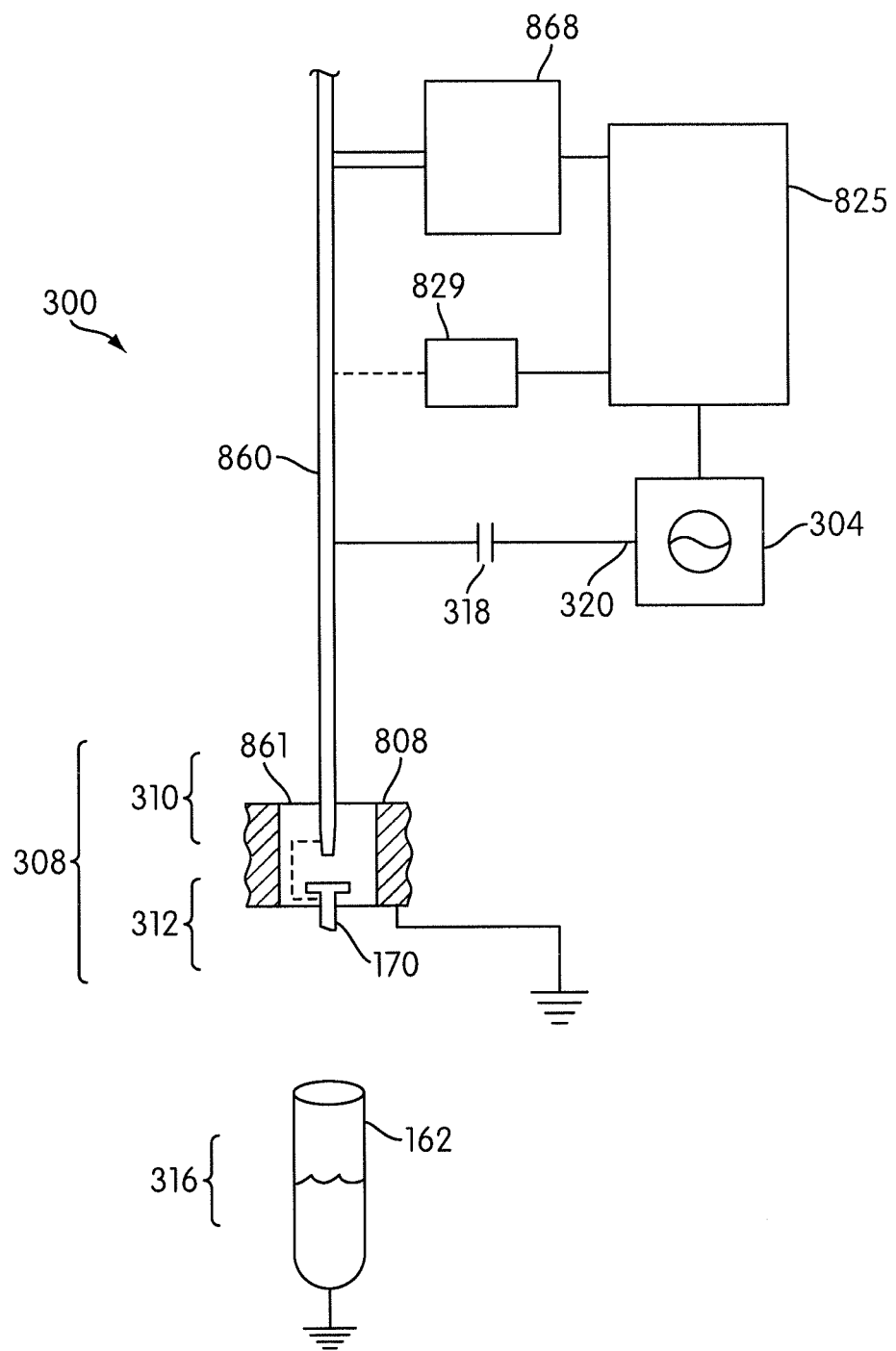
FIG. 16 is a schematic representation of a capacitive sensing system which uses a capacitive voltage divider for the dual purposes of sensing the presence or absence of a protective conduit, such as a contamination-limiting tip, on the distal end of a fluid transfer probe and sensing the level of fluid contents in a receptacle.

FIG. 16 is a schematic representation of a capacitive detection system 300 for tip detection and fluid level sensing using a capacitive proximity sensor. In an embodiment of the invention, as described above, each magnetic separation wash station 800 has five fluid transfer probes 860 that are moved together vertically by the tube holder 862 coupled to the drive screw 866 that is actuated by lift motor 868. Vertical height of the fluid transfer probes 860 is determined by monitoring Z-axis position sensor 829 and the number of steps of the lift motor 868 driving the fluid transfer probes 860. Both the lift motor 868 and the Z-axis position sensor 829 are in communication with the magnetic separation wash station embedded controller 825, as indicated by solid lines between lift motor 868 and sensor 829 and embedded controller 825. Mechanical coupling between lift motor 868 and fluid transfer probe 860—via drive screw 866, threaded sleeve 863, and tube holder 862—is represented in FIG. 16 by double lines. Optical coupling between the sensor 829 and the fluid transfer probe 860 is represented by a dashed line. The controller 825 monitors the Z-axis position of the fluid transfer probes 860 by monitoring the number of steps of the lift motor 868 driving the fluid transfer probe 860. The controller 825 can further correlate that Z-axis height to determine the position of a specific portion of the fluid transfer probe 860, such as the distal end thereof, with respect to a probe hole 314 formed through the midplate 808 or with respect to a reaction receptacle 162. FIG. 16 represents the configuration of a capacitive sensing system for one fluid transfer probe 860 implemented within this system. It will be appreciated that a comparable configuration may be provided for each fluid transfer probe 860.

The capacitive sensing system includes a proximity sensor circuit represented in FIG. 16 by block 304, which is in communication with embedded controller 825. Details of the proximity sensor circuit 304 are described in further detail below. A shield (not shown) surrounds the fluid transfer probe drive circuit (not shown), which minimizes stray capacitance. The proximity sensor circuit 304 propagates a sine wave at the electrode pin 320. The sine wave travels through the series capacitor 318, to the fluid transfer probe 860. The series capacitor 318 is provided for AC coupling to take out any DC offset in the drive signal.

Proximity sensor circuit 304 includes an electric field imaging device ("EFID") configured for non-contact sensing of objects. Suitable devices are available from Freescale Semiconductor of Austin, Tex. (model numbers MC33940 or MC33941). The EFID of the proximity sensor circuit 304 is connected to each fluid transfer probe 860. In an embodiment, a different pin of the EFID is connected, through a series capacitor 318, to each of the fluid transfer probes 860, which function as electrodes for the proximity detection circuit. The EFID generates a sine wave that is transmitted from the EFID to the electrode (i.e., probe 860). Objects that form a capacitor between the fluid transfer probe 860 and ground change the amplitude of this sine wave. The EFID may generate a sine wave at any one of several frequencies that will work for this purpose. In an embodiment of the invention, the EFID generates a sine wave at approximately 240 kHz, but higher or lower frequencies may be used if they offer better performance in alternate implementations of the invention. The proximity sensor circuit 304 further includes a detector for detecting a signal, e.g., voltage, from each probe 860.

Figure 24:
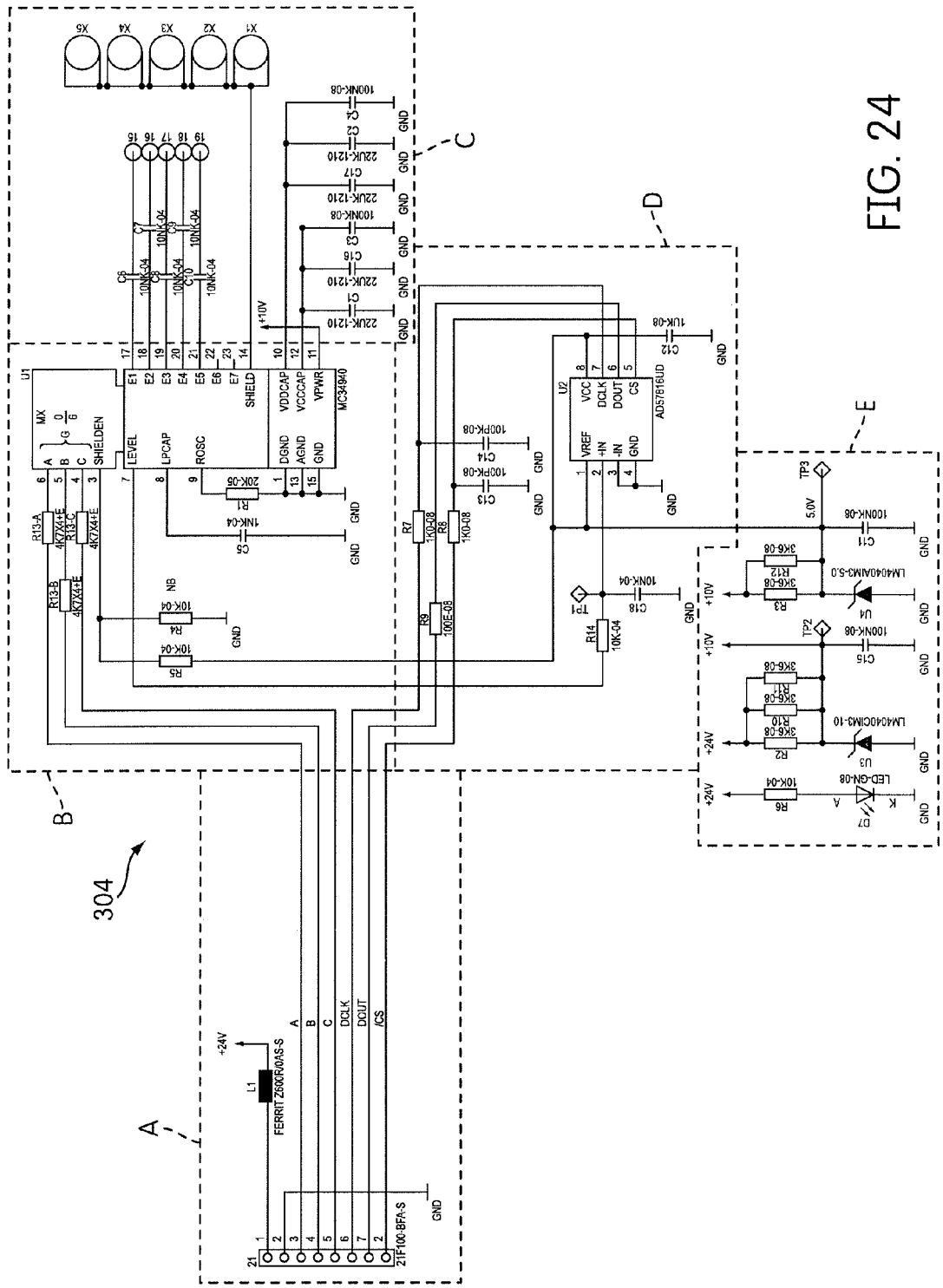
FIG. 24 is schematic view of a proximity sensor circuit.

An embodiment of a proximity sensor circuit 304 is shown schematically in FIG. 24, with different portions of the circuit shown isolated and enlarged in FIGS. 24A-24E. The proximity sensor circuit 304 may be embodied in a capacitive sensing printed circuit board ("PCB"), which may be physically mounted within the housing 802 of the magnetic wash station 800, for example, to the tube holder 862, whereby it is connected to the magnetic separation wash station controller board 825 via a flex cable (not shown).

Figure 24A:
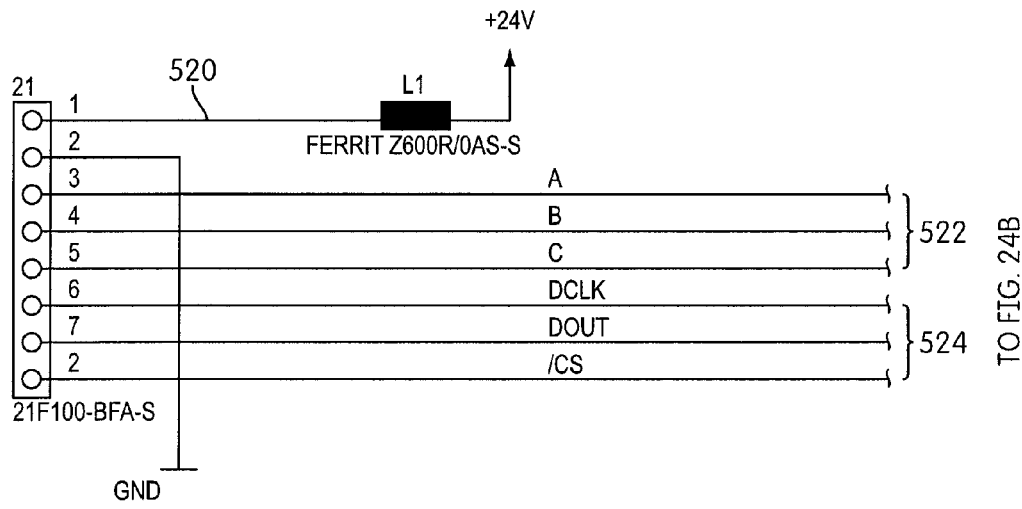
FIG. 24A is an enlarged, isolated view of portion "A" of the circuit shown in FIG. 24.

Referring to FIG. 24A, which shows portion "A" of the proximity sensor circuit 304 shown in FIG. 24, the circuit includes power input at 520. In one embodiment, the power input is 24 V from the diagnostic analyzer in which the proximity sensor circuit 304 is incorporated. Lines A, B, and C—shown at reference number 522—are digital control lines for selecting a channel, thereby selecting fluid transfer probe 860 to be interrogated. Lines DCLK, DOUT, and /CS—shown at reference number 524—are control lines to read the A/D converter.

Figure 24B:
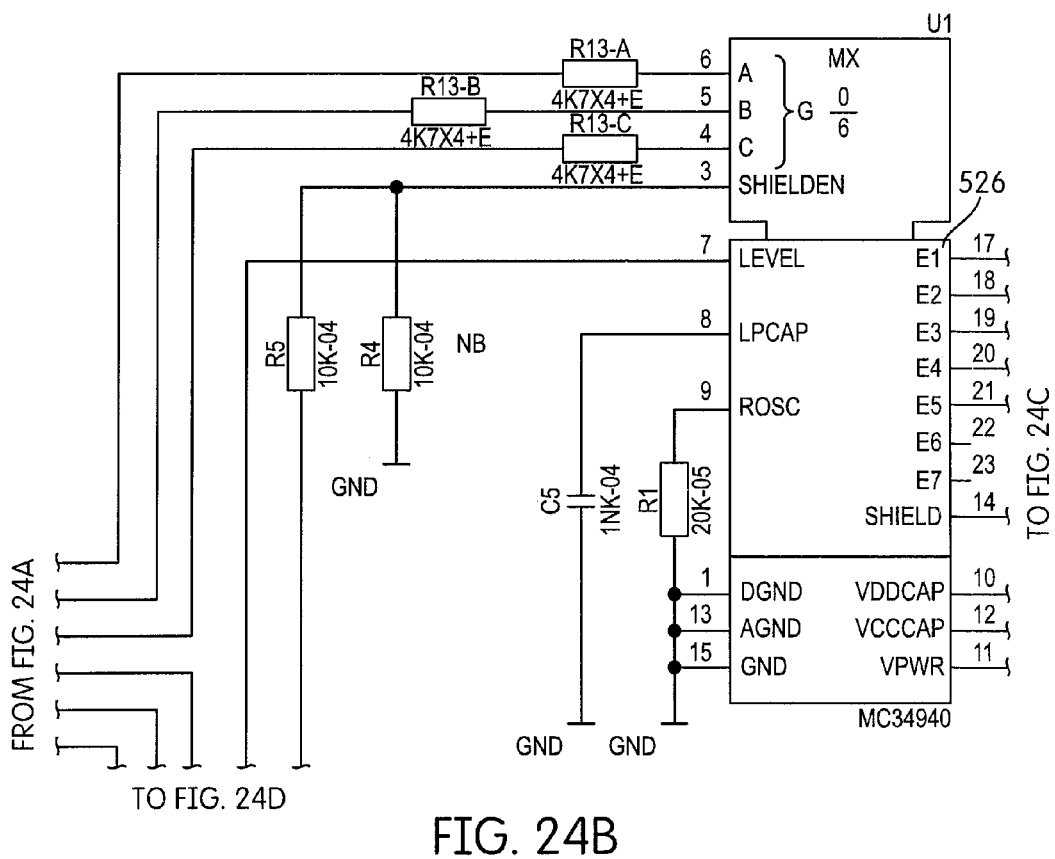
FIG. 24B is an enlarged, isolated view of portion "B" of the circuit shown in FIG. 24.

Referring to FIG. 24B, which shows portion "B" of the proximity sensor circuit 304 shown in FIG. 24, the EFID is shown at reference number 526.

Figure 24C:
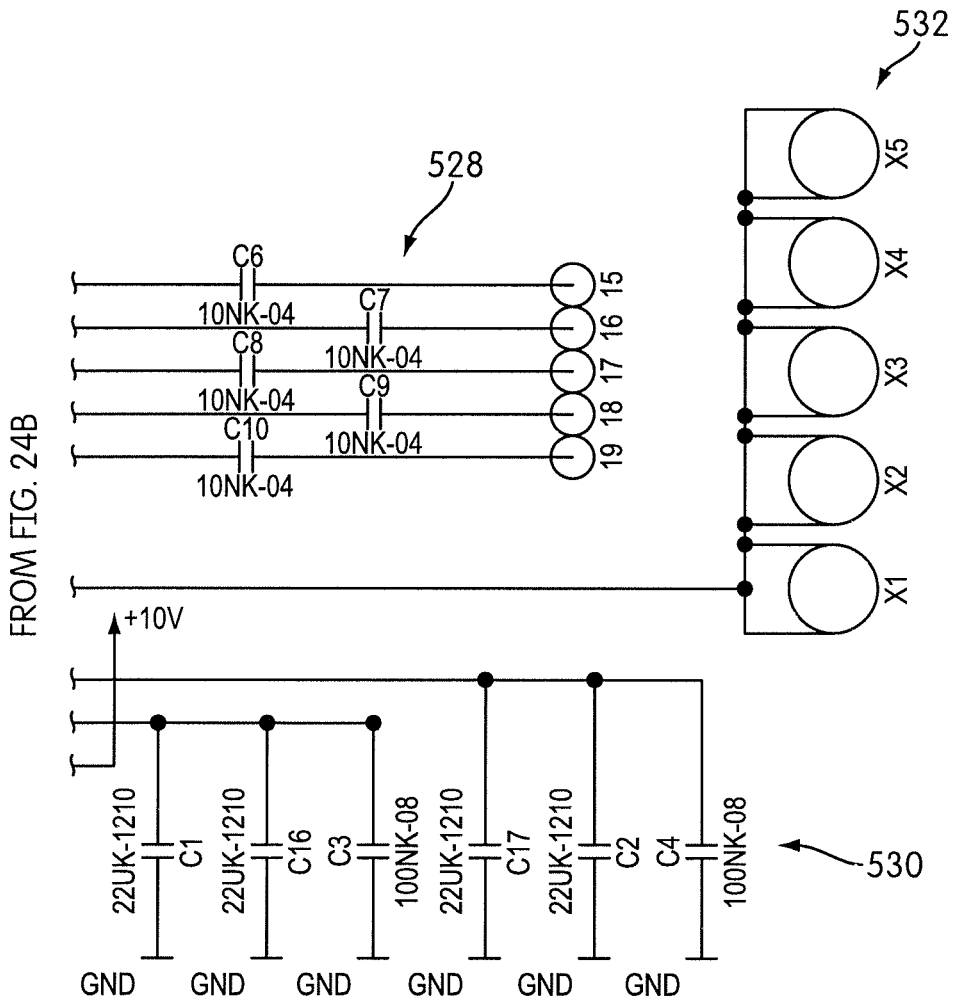
FIG. 24C is an enlarged, isolated view of portion "C" of the circuit shown in FIG. 24.

Referring to FIG. 24C, which shows portion "C" of the proximity sensor circuit 304 shown in FIG. 24, reference number 528 designates electrode I/O at which one or more of the pins E1-E7 of the EFID 526 (see FIG. 24B) are connected to a corresponding one of the fluid transfer probes through a series capacitor. In the exemplary magnetic separation wash station 800, each of the five pins E1-E5 is connected to one of the fluid transfer probes 860. The series capacitor is for AC coupling to take out any DC offset in the drive signal. Reference number 532 designates a shield that surrounds the transfer probe drive circuit traces on the printed circuit board to minimize stray capacitance. The capacitors shown at reference number 530 are used by internal power supplies of the EFID 526.

Figure 24D:
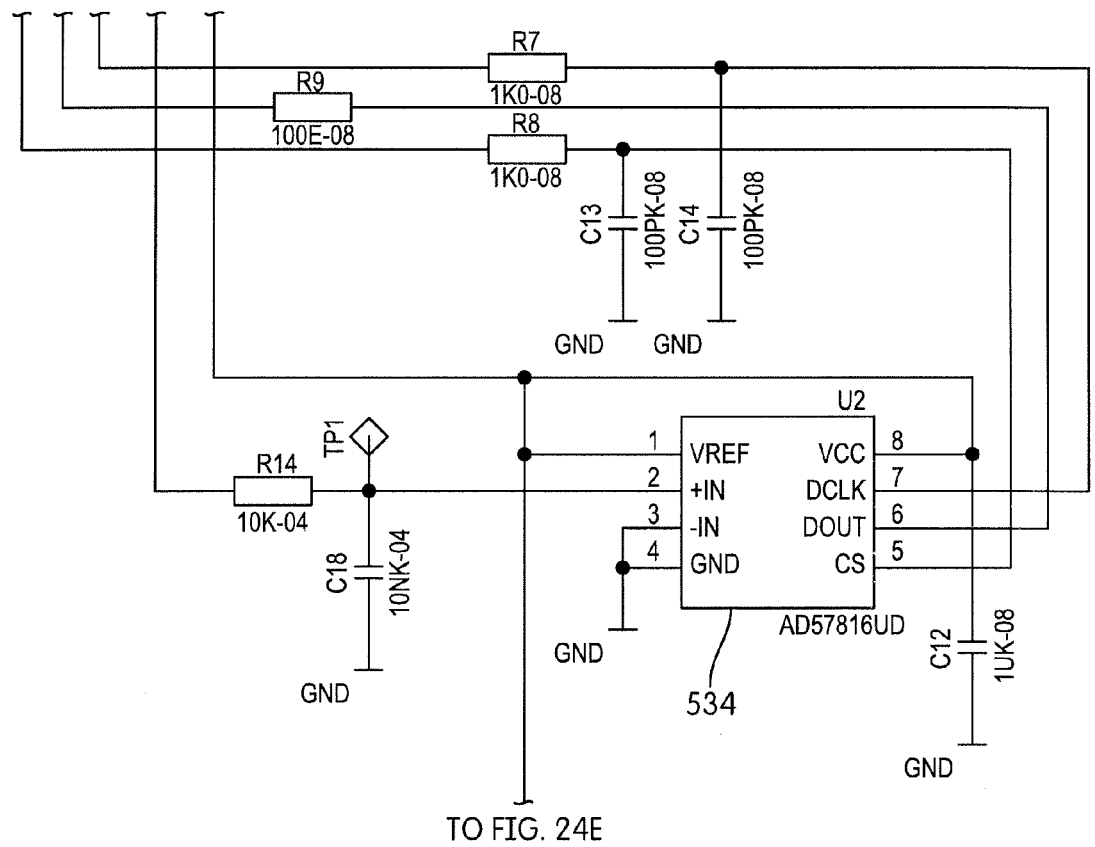
FIG. 24D is an enlarged, isolated view of portion "D" of the circuit shown in FIG. 24.

Referring to FIG. 24D, which shows portion "D" of the proximity sensor circuit 304 shown in FIG. 24, reference number 534 designates the A/D converter that is constructed and arranged to digitize the output of the EFID 526 to give a signal proportional to the capacitance between the selected electrode (e.g., one of the fluid transfer probes 860) and the ground.

Figure 24E:
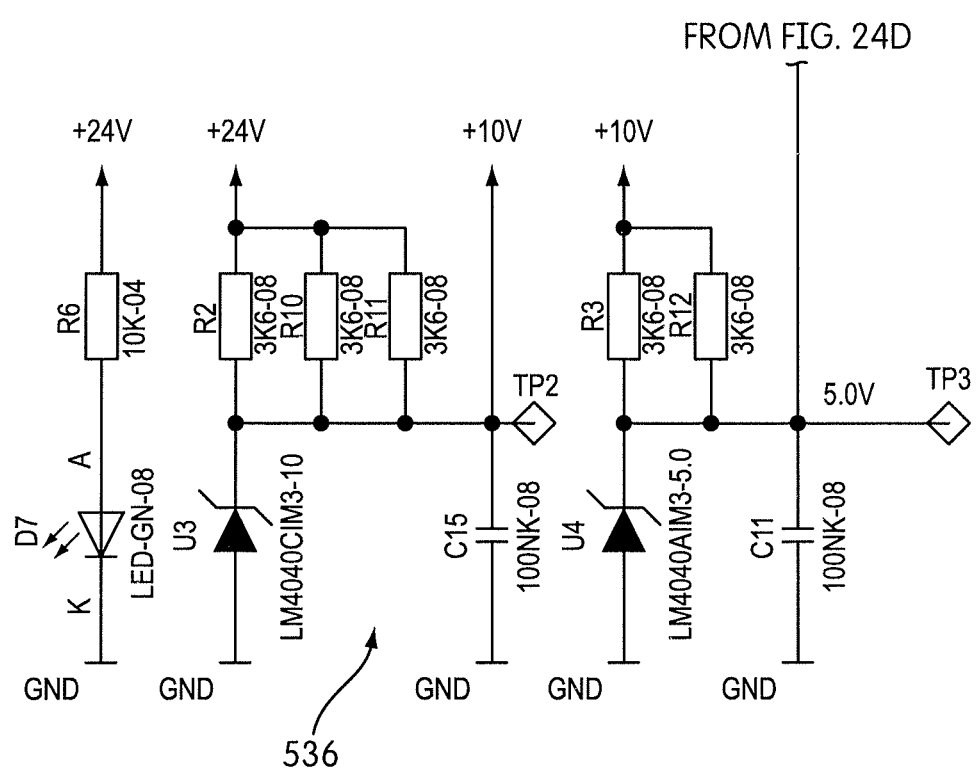
FIG. 24E is an enlarged, isolated view of portion "E" of the circuit shown in FIG. 24.

Referring to FIG. 24E, which shows portion "E" of the proximity sensor circuit 304 shown in FIG. 24, reference number 536 designates power supplies which divides the power input—24 V in one embodiment—between the EFID 526 and the A/D converter 534. In the illustrated embodiment, the EFID 526 requires 10 V and the A/D converter 534 requires 5 V, and portion 536 of the circuit 304 divides the input voltage accordingly.

In an embodiment of the invention, the signal output from the fluid transfer probe 860, as measured at the detector of the proximity sensor circuit 304, is converted to a voltage. The voltage measured is an inverse function of the capacitance between the electrode being measured (probe 860), the surrounding electrodes (the other probes 860), and other objects in the electric field surrounding the electrode. Increasing capacitance results in decreasing voltage. The capacitance measured is proportional to the area of the electrode, the dielectric constant of the material between the electrodes (which in the present implementation is air), and is inversely proportional to the distance between the objects. The proximity sensor circuit 304 further includes an A/D converter (not shown) which digitizes the output of the electrode (probe 860) measured by the detector to give a signal proportional to the capacitance between the selected electrode and the ground. The measured signal can be plotted against encoder counts of the lift motor 868 (which is related to the Z-axis elevation of the probes 860) to generate a signal curve that shows variation in capacitance with vertical movement of the fluid transfer probes 860.

Thus, in an embodiment of the invention, the capacitor for proximity sensing in the proximity sensor circuit 304 is comprised of the fluid transfer probe 860 as the charged plate with a secondary structure, such as the midplate 808, as the grounded plate. The midplate 808 is a solid block made of a conductive material that is electrically grounded and includes holes 314 through which the fluid transfer probes 860 pass when moved vertically within the station 800.

The capacitive signal of the probe 860 is monitored for indication of the presence of a tip 170 as the fluid transfer probe 860 moves with respect to a secondary structure, such as the opening 314 formed in the midplate 808, through a tip sensing range 308 defined by a high tip check position 310 and a low tip check position 312. The high tip check position 310 can be referred to as "in" the midplate 808, and the low tip check position is 312 may be referred to as "below" the midplate 808. As the probe is moved between positions 310 and 312 within the tip sensing range 308, the capacitive signal (in mV) versus the Z-axis position of the probe 860 (as determined by encoder counts of lift motor 868) is recorded.

Figure 17:
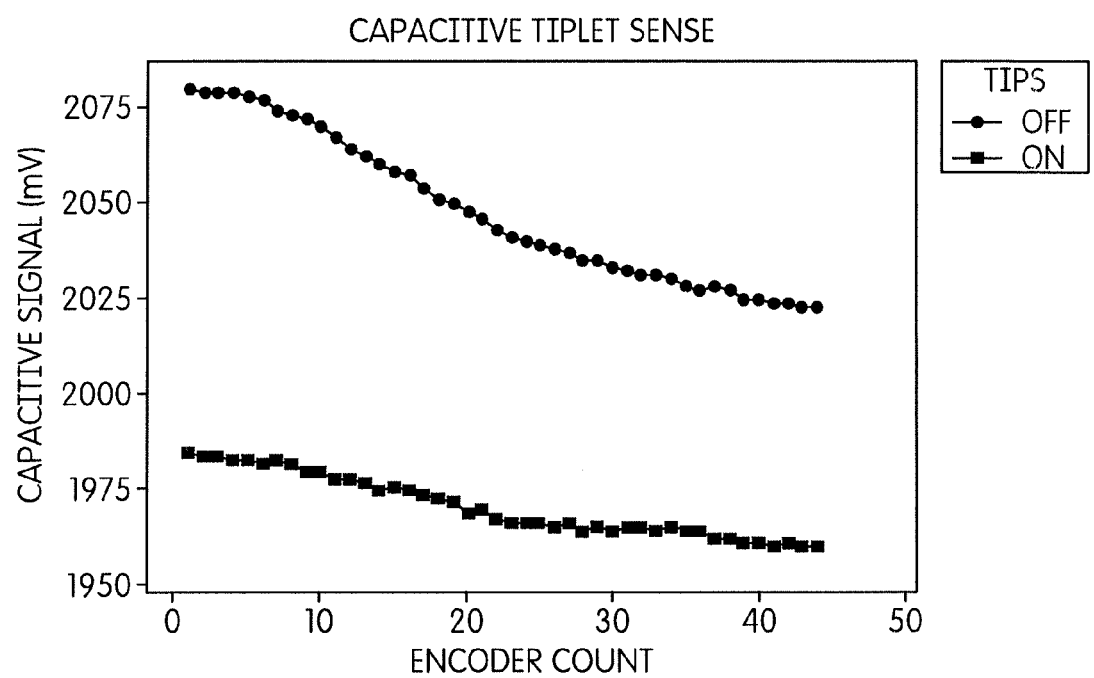
FIG. 17 is a graph showing two waveforms of capacitive signal used for proximity sensing, wherein one waveform represents the signal of a fluid transfer probe with a protective conduit attached and the other waveform represents a fluid transfer probe without a protective conduit attached.
Figure 18A:
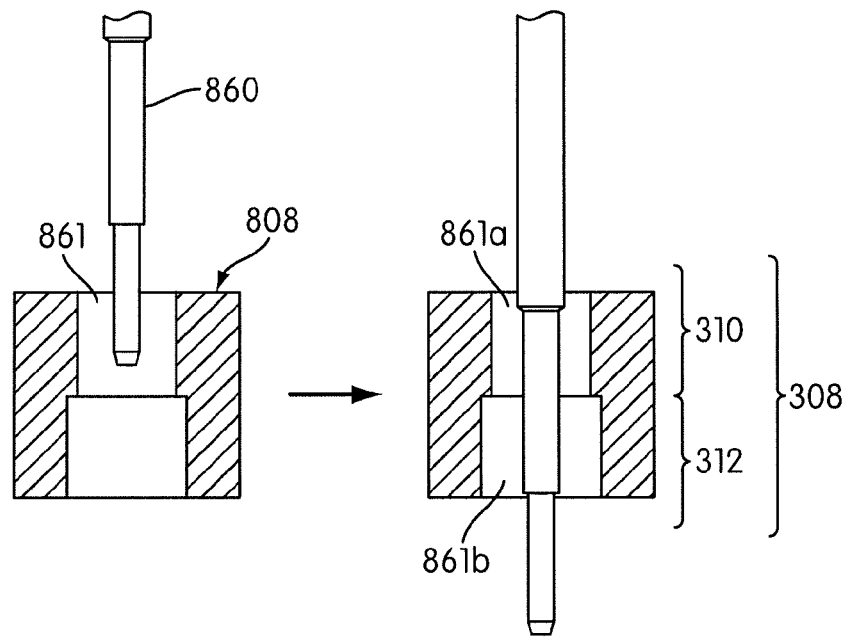
FIGS. 18A and 18B are cross-sectional representations of the progression of a fluid transfer probe as it moves through the a hole in a solid grounded block made of a conductive material during which the presence or absence of a partially capacitive protective conduit is sensed.
Figure 18B:
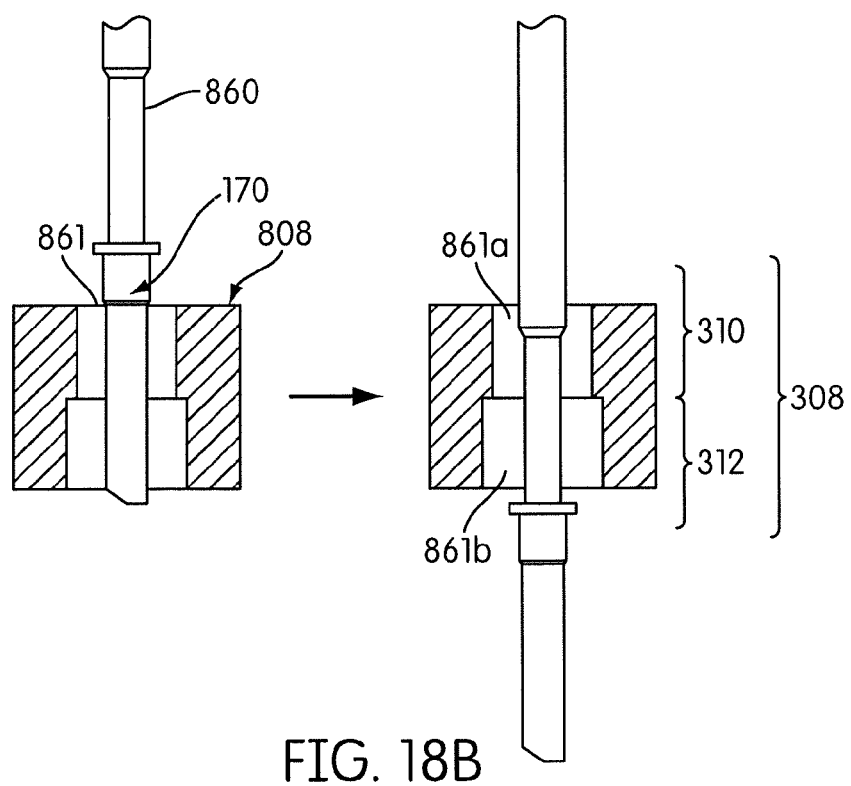

The resulting waveform that is measured and evaluated to determine whether or not there is a tip 170 present on the end of a fluid transfer probe 860 is referred to herein as "the $\alpha$-waveform." Examples of such waveforms are shown in FIG. 17. The upper curve represents the signal from one probe 860 as the probe moves through the tip sensing range 308 with the tip 170 off, and the lower curve represents the signal from one probe 860 moving through tip sensing range 308 with a tip 170 present at the probe's distal end. FIG. 18A shows the progression of the fluid transfer probes 860, without tips 170, starting at the high tip check position 310 at the top of hole 314 in the midplate 808 and moving through hole 314 in the midplate 808 to the low tip check position 312. Similarly, FIG. 18B shows the progression of the fluid transfer probes 860, with tips 170, starting at the high tip check position 310 at the top of a hole 314 in the midplate 808 and moving through hole 314 in the midplate 808 to the low tip check position 312.

In optimizing the design of the midplate 808, there can be a tradeoff between signal strength—which can be improved if each of the holes 314 is relatively small so that the tip 170 and the probe 860 are in close proximity to the side of the hole 314—and avoiding contamination which can occur if sample fluids on the tip 170 touch the side of the hole 314. In one embodiment, as shown in FIGS. 18A and 18B, the hole is formed in a step-wise fashion, with the diameter of an upper portion of the hole 314a being smaller than the diameter of a lower portion of the hole 314b. The smaller upper portion of the hole 314a reduces the distance between the side of the hole 314 and the probe 860 and the tip 170, thereby providing a stronger signal. The larger lower portion 314b provides a larger clearance between the tip 170 and the side of the hole 314. This larger clearance can reduce the possibility of contamination by reducing the likelihood that a lower part of the tip 170—which is the part of the tip 170 that comes into contact with the fluid in each receptacle vessel 162 of the MRD 160—contacts the midplate 808.

The presence of a tip 170 on the probe 860 results in a different capacitive signal output than when the tip 170 is absent from the fluid transfer probe 860. For example, as shown in FIG. 17, the general amplitude of the signal is higher (meaning lower capacitance in the system) as the probe 860 moves through the tip sensing range 308 (as determined from encoder counts of the lift motor 868) when the tip 170 is absent than when the tip 170 is present. Furthermore, the variation in the signal amplitude as the probe 860 moves from the high tip check position 310 to the low tip check position 312 is larger when the tip 170 is absent than when the tip is present 170. Thus, whether a tip 170 is present or absent can be determined by monitoring the general amplitude of the capacitive signal and/or by monitoring the variation in the capacitive signal as the fluid transfer probe moves from the high tip check position 310 to the low tip check position 312.

The $\alpha$-waveform can be analyzed in a number of ways to determine the presence or absence of a tip 170. For example, the starting and ending capacitance can be subtracted from one another and the difference compared to a threshold, and/or the slope of the $\alpha$-waveform can be analyzed, whereby the slope will be different for tip present and tip absent conditions. The fundamental concept is to leverage changes in the $\alpha$-waveform (amplitude and/or slope) that occur when a tip 170 present or absent. Thus, a characteristic of the measured $\alpha$-waveform, such as amplitude or rate of change (slope), can be compared to a reference value, such as a predetermined threshold that can be derived from the amplitude and/or the rate of change (slope) of reference signals that would be expected when the tip is present or absent, to determine if the measured $\alpha$-waveform indicates the presence or absence of a protective tip.

Optionally, to ensure the accuracy of the reading, and to reduce any variation in the signal, a fluid transfer probe 860 may be moved through the capacitive presence sensing range 308 from the high tip check position 310 to the low tip check position 312 multiple times and the recorded signals may be averaged, and the average of the related $\alpha$-waveforms can be analyzed to determine the presence of a tip 170. In an embodiment of the invention, a reading with a sufficient signal-to-noise output should be achieved when the fluid transfer probe 860 repeats the movement between the high tip check position 310 and low tip check position 312 at least three times.

Figure 19:
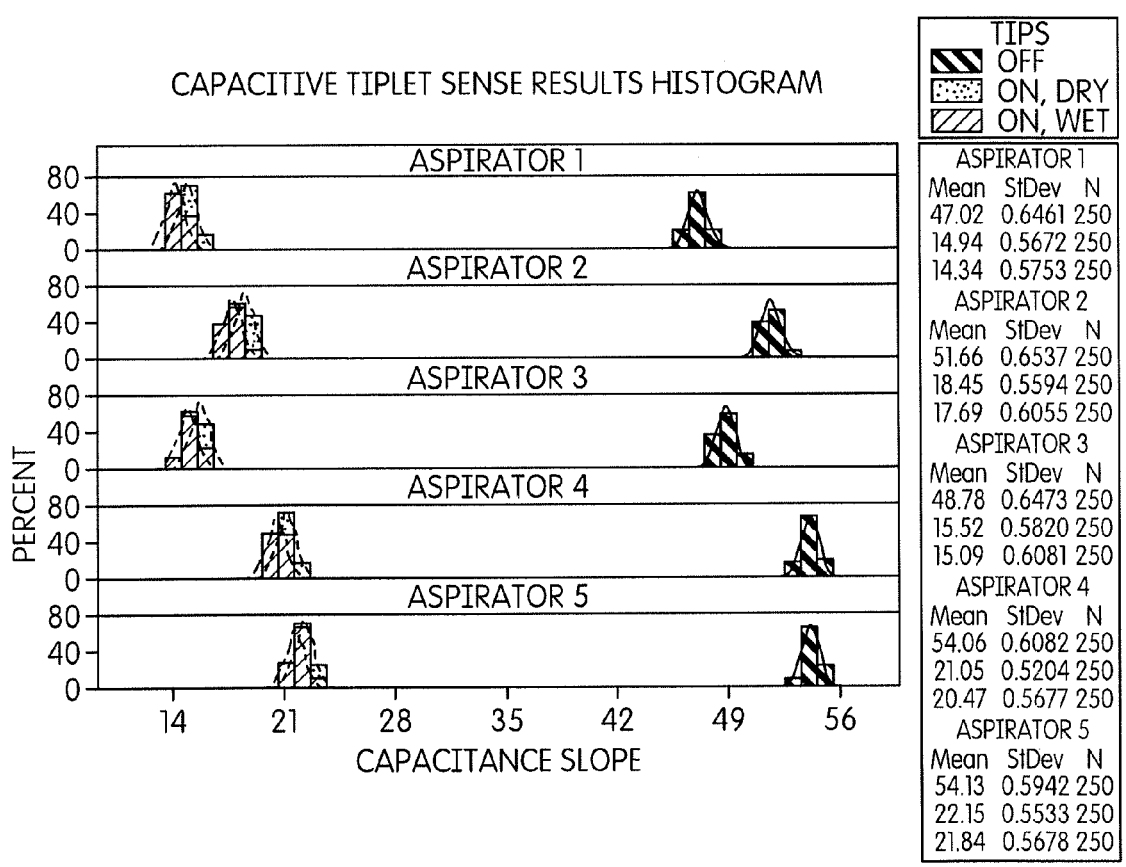
FIG. 19 is a histogram for five fluid transfer probes (e.g., aspirators), wherein the values of the histogram are the slopes of the capacitive proximity sensing waveforms for each fluid transfer probe with and without protective conduits attached, which is used to set threshold values used in analysis indicating the presence or absence of protective conduits.

FIG. 19 is a histogram of the slopes derived from a capacitive proximity sensor circuit, using signal from five fluid transfer probes 860, referred to as aspirators, as an example. The histogram shows that there is a clear difference between slope measurements of the $\alpha$-waveform when tips 170 are on and off. Analysis of the histogram allows for the selection of a reference, or threshold, value of the slope, which can be used for establishing what readings of an $\alpha$-waveform indicate the presence or absence of a tip 170. The threshold is set at a value between the mean of the "on" slopes and the mean of the "off" slopes of these reference signals. This value may be the mean or midpoint between the mean "on" and mean "off" values, or a point that is an equal number of standard deviations away from each respective mean value. A threshold value may be set for all fluid transfer probes 860 in all magnetic separation wash stations 800 in a system. For example, using the data from FIG. 19, for all five fluid transfer tubes 860, a slope value of 37 or greater could be considered a tip-off condition, and a slope value below 37 could be considered a tip-on condition. In other embodiments in which the reference, or threshold, value is determined from the data shown in FIG. 19, the reference, or threshold, value used to discriminate between the tip-off condition and the tip-on condition is any value between 28 and 42. In still other embodiments, the reference, or threshold, value used to discriminate between the tip-off condition and the tip-on condition may be determined from only tip-on reference data (i.e., $\alpha$-waveform) or only tip-on reference data (i.e., $\alpha$-waveform). Alternatively, the multiple fluid transfer tubes 860, which may be referred to as multiple "channels," in a magnetic separation wash station 800 may have a distinct threshold value set for each channel. For example, using the data from FIG. 19, threshold slopes could be set at 33 for channel 1, 38 for channel 2, 33 for channel 3, 37 for channel 4, and at 38 for channel 5. Such a threshold value for each channel may be identical across all magnetic separation wash stations 800 in a system. Each individual magnetic separation wash station 800 may have variation and thus require calibration or setting threshold values for slope that are specific to the fluid transfer probes 860 in individual magnetic separation wash stations 800. This implemented threshold value may be determined based on repeated testing of at least one magnetic separation wash station 800.

As described in more detail below, this sequence of moving the probes 860 through the opening 314 in the midplate while recording the capacitive signal from the probe 860 can be used to confirm the presence of a tip 170 on each probe 860 following a tip pick procedure, and it can be used to confirm the absence of tips 170 from all probes 860 following a tip strip procedure.

Exemplary processing for operating a diagnostic analyzer including a magnetic separation wash station incorporating a proximity sensor system for detecting fluid levels (i.e., fluid volume) and tip presence are described below with references to FIGS. 20, 21, and 23B. In describing the actions taken by the system as shown in flowcharts of FIGS. 20, 21, and 23B, the following terms are used to describe the resulting changes to the processing of reaction receptacles in the diagnostic analyzer.

The status of a magnetic separation wash station 800 is set to "fatal error" by the control system to indicate that no more MRDs 160 will be sent to the magnetic separation wash station 800 that registers the error. The control system as a whole will only perform downstream processing of MRDs 160 that have passed through that particular magnetic separation wash station 800. In this context, the "control system" refers to the embedded controller 825 of the magnetic separation wash station 800 and/or the microprocessor controller of the diagnostic analyzer of which the magnetic separation wash station 800 is a part.

Setting the status of a magnetic separation wash station 800 to "out of service" indicates that the control system will allow the next MRD 160 queued for the magnetic separation wash station 800 that registered the error to attempt processing. The control system, however, will stop scheduling MRDs 160 for this particular magnetic separation wash station 800. Processing may still be attempted for the MRDs 160 that remain queued for this magnetic separation wash station 800, which may potentially bring this magnetic separation wash station 800 back into service if those queued MRDs 160 complete their processes in the station without further errors.

Setting the status of a fluid transfer probe 860 to "channel out of service" indicates that the control system will allow the magnetic separation wash station 800 that registered the error to attempt processing the MRD 160. However, the control system will stop further introduction of fluids into this channel, where the channel corresponds to one of the five receptacle vessels 162 that comprise an MRD 160. The reason for allowing the control system to take a channel of the fluid transfer probes 860 out of service is to allow for continued processing of the other four receptacle vessels in the MRD 160 without risking cross-contamination into the other four fluid transfer probes 860 of the magnetic separation wash station 800. Further, taking a channel of the fluid transfer probes 860 out of service allows for continued processing of subsequent MRDs 160 in the magnetic separation wash station 800 without risking cross-contamination of material in the reaction receptacle 162 corresponding to the channel that has been taken out of service. In one embodiment, if a magnetic separation wash station 800 registers three channels as "channel out of service," the control system will then register an "out of service" error for the whole magnetic separation wash station 800.

In a variation, the control system will not automatically stop dispensing fluids into the channel with an error. Fluids will not be dispensed if the system detects excess fluids in this channel on subsequent MRDs 160. The MRDs 160 will be treated the same as previous MRDs 160, in that the system will make an attempt to process all receptacle vessels 162. The control system will, however, stop scheduling tests for this channel of this magnetic separation wash station 800.

Setting the status of a reaction receptacle being processed to "invalidate tube" indicates that the control system will not add further reagents to or process results for that individual receptacle vessel 162 (in an embodiment in which the receptacle comprises a tube).

Setting the status of an MRD 160 to "invalidate MRD" indicates that processing of the MRD 160 will be aborted and that the control system will not add further reagents to or report results for all five receptacle vessels 162 of that MRD 160.

Figure 20:
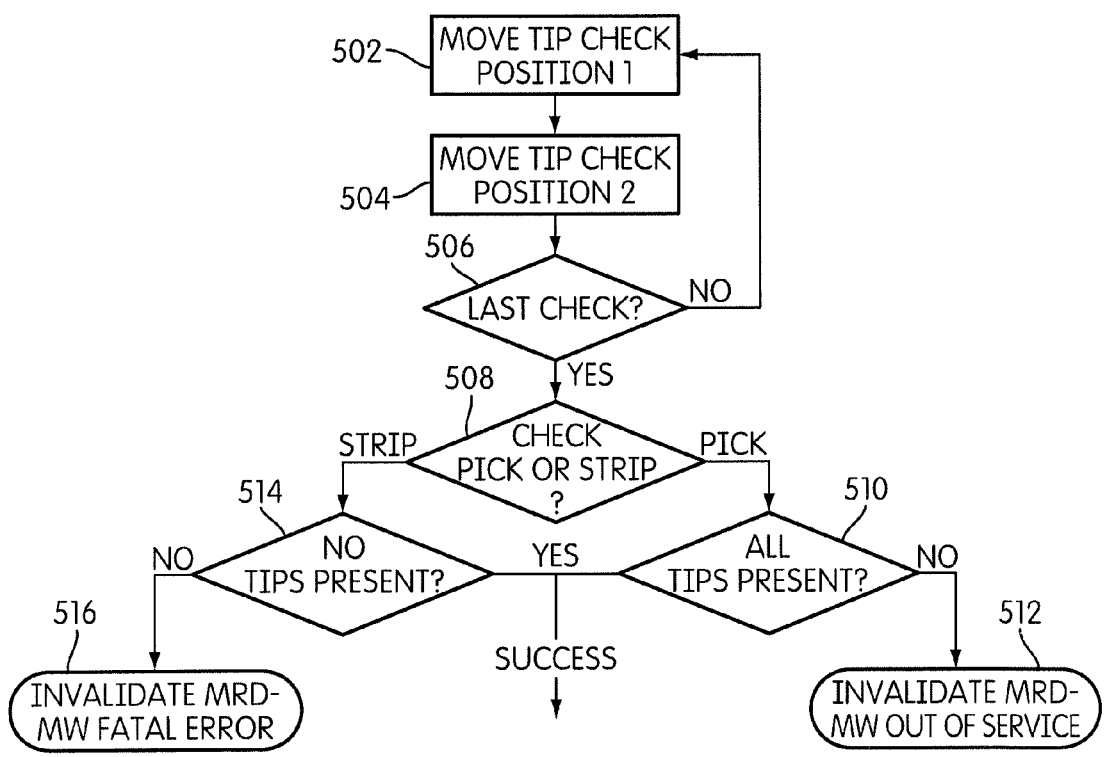
FIG. 20 is a flow chart detailing the decision process when the system evaluates a fluid transfer probe by use of a capacitive voltage divider for the presence or absence of attached protective conduits.

FIG. 20 is a flow chart detailing the decision process for capacitive presence detection of a tip 170 on the distal end of a fluid transfer probe 860 using the midplate 808. The control system moves the fluid transfer probe 860 to the capacitive presence sensing range 308, starting at the high tip check position 310 and ending at the low tip check position 312.

At step 502, the fluid transfer probe 860 is moved to "Tip Check Position 1" corresponding to the high tip check position 310 within the midplate 808. Next, at step 504, the fluid transfer probe 860 is moved down to "Tip Check Position 2" corresponding to the low tip check position 312 below the midplate 808. The Tip Check Positions 1 and 2 can be determined and verified from, for example, input signals from the Z-axis sensors 829, 827 and/or encoder counts of Z-axis steps taken by the lift motor 868. As the fluid transfer probe 860 moves from the high tip check position 310 to the low tip check position 312, the capacitive signal is recorded and plotted against the encoder count of Z-axis steps taken by the lift motor 868, as shown by example in FIG. 17. At process step 506, the control system queries whether this is the last check for the current capacitive presence sense for the tip. This query exists because, as explained above, movement between the high tip check position 310 and low tip check position 312 may be repeated a set number of times. If the parameter which determines if the process is at the last check at step 506 registers "no," then the process returns to step 502 wherein the fluid transfer probe 860 moves back up to the high tip check position 310 and proceeds again to step 504 wherein the fluid transfer probe 860 moves down through the hole 314 in the midplate 808 to the low tip check position 312. The control system again records the capacitive signal from the fluid transfer probe 860 as it moves through the capacitive presence sensing range 308. If the parameter which determines if the process is at the last check at step 506 registers "yes," the control system then queries at step 508 whether it is checking for a successful tip pick (tip present) or a successful tip strip action (tip absent).

If the system is seeking to verify that tips 170 have been picked by the fluid transfer probes 860, then at step 510 the system queries whether all tips are present. This query evaluates the α-waveforms generated and recorded by the proximity sensor circuit 304 for all five fluid transfer probes 860 in the magnetic separation wash station 800—for example, by comparing a characteristic of the α-waveforms, such as rate of change (slope) or amplitude—to a predetermined reference value—, and returns a positive result when the evaluations of all five α-waveforms indicate that a tip 170 is attached to the distal end of each fluid transfer probe 860. If the system registers that all tips are present, then there was a successful tip pick action by all five fluid transfer probes 860, and the capacitive presence sensing tip check sequence concludes. If all tips are not present, then at step 512 the MRD 160 is invalidated, and the magnetic separation wash station ("MW") 800 is taken out-of-service. Alternatively, the status may be changed to channel out of service, invalidate tube, or invalidate MRD, or some other indication of error.

If the system is checking to verify that a tip 170 has been stripped from the distal end of a fluid transfer probe 860, then at step 514 the system queries whether any tips 170 are present on the end any of the five fluid transfer probes 860 of the magnetic separation wash station 800. The system returns a positive result when the evaluations of all five α-waveforms—for example, by comparing a characteristic of the α-waveforms generated and recorded by the proximity sensor circuit 304, such as rate of change (slope) or amplitude—to a predetermined reference value—indicate that a tip 170 is not attached to the distal end of each fluid transfer probe 860. Optionally, following fluid transfer, the system may delay before checking whether or not tips 170 are present. This delay is preferably at least ten seconds. If the control system indicates that no tips are present, then there was a successful tip strip action by all five fluid transfer probes 860, and the capacitive presence sensing tip check sequence concludes. If all tips are not removed, i.e., the capacitive signal of at least one fluid transfer probe 860 registers the presence of a tip 170, then at step 516 the MRD 160 is invalidated, and the status of the magnetic separation wash station 800 is changed to fatal error.

The optional delay before checking whether or not tips 170 have been stripped allows any fluid which is transferred to flow completely past and through the structure of the fluid transfer probe 860 and the fluid transfer tubing 864 connected at the proximal end of the fluid transfer probe. Residual fluid on or within a fluid transfer probe 860 or fluid transfer tubing 864 may form a conductive path between the fluid transfer probe 860 and the environment outside the magnetic separation wash station 800, thus affecting the capacitance measured between a fluid transfer probe 860 and its surrounding environment. The delay increases the probability that no fluid is in contact with the fluid transfer tubing 864 or fluid transfer probe 860 when capacitive presence sensing occurs following fluid transfer, which mitigates against the risk that any fluid transferred will affect the determination of the presence or absence of a tip 170.

When tips 170 are stripped off of the fluid transfer probes 860, there is direct contact between the probe and the tip striping structure, which saturates the capacitive signal output by the fluid transfer probe 860. In the above description, the tip stripping structure is fabricated from a conductive material and is mechanically and electrically coupled to the magnetic separation wash station housing 802, effectively grounding the proximity sensor circuit when contact is made between the fluid transfer probe 860 and the tip stripping structure. Thus, measurement and analysis of such a signal saturation event may be used in addition to, or instead of, performing the capacitive presence detection sequence using the midplate as described above in conjunction with FIG. 20.

Figure 21:
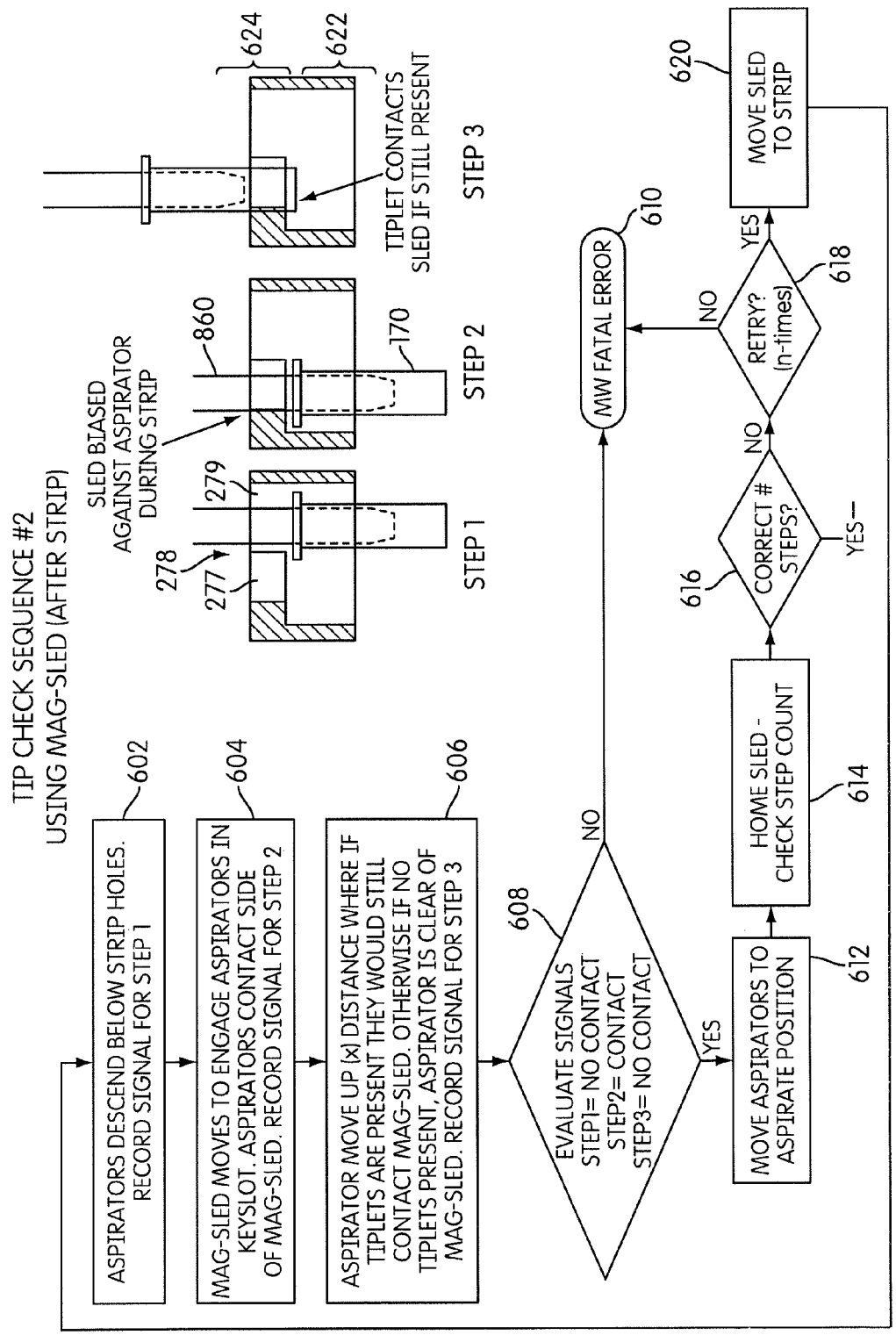
FIG. 21 is a flow chart and schematic diagram detailing the tip stripping process and mechanism using a magnetic sled apparatus.

FIG. 21 is a flowchart describing the process to check for the presence of a tip 170 at the end of a fluid transfer probe 860 in conjunction with a tip stripping procedure using the tip stripping openings 228, 278 of either of the magnetic sleds 202, 252, respectively, described above in conjunction with FIGS. 10-15. As set forth below, FIG. 21 makes reference to magnetic sled 252 and key-hole shaped tip stripping opening 278, but it will be understood that this process is analogous in embodiments using magnetic sled 202 and key-hole shaped tip stripping opening 228.

The cycle begins at step 602 wherein the fluid transfer probe 860 descends into the first, large portion 279 of the key-hole shaped tip stripping opening 278 to a tip strip starting position 622. In this position, neither the fluid transfer probe 860 nor the tip 170 should be in contact with the bottom plate 276, and the control system records the capacitive signal from the fluid transfer probe 860. The position of the fluid transfer probe 860 can be determined and verified from, for example, input signals from the Z-axis sensors 829, 827 and/or encoder counts of Z-axis steps taken by the lift motor 868.

Next, at step 604, the magnetic sled 252 is moved laterally, as described above, to engage the fluid transfer probes 860 in the small portion 277 of the keyhole opening 278. The position of the magnetic sled can be determined and verified from, for example, input signals from the sensors 296, 298 and/or encoder counts of the drive motor 286. At this step, the fluid transfer probe 860 should contact the side of the bottom plate 276, i.e. the magnetic sled 252 is biased against the fluid transfer probe 860, and the control system records the capacitive signal from the fluid transfer probe 860 as generated and recorded by the proximity sensor circuit 304. The capacitive signal should be saturated (i.e., at or above a maximum level) due to the direct contact between the fluid transfer probe 860 and the magnet sled 252.

Subsequently, at step 606, the fluid transfer probe 860 moves up to a tip strip ending position 624 (again, the position of the fluid transfer probe 860 can be determined and verified from, for example, input signals from the Z-axis sensors 829, 827 and/or encoder counts of Z-axis steps taken by the lift motor 868). If any tips 170 are still present on the distal end of the fluid transfer probes 860, the tip(s) 170 will be in contact with the magnetic sled 252 and specifically in contact with the bottom plate 276, and the capacitive signal from the fluid transfer probe 860 as generated and recorded by the proximity sensor circuit 304 will still be saturated. If no tips 170 are still attached to the probes 860, then the fluid transfer probe 860, which is up at the tip strip ending position 624, is clear of and not in contact with the magnetic sled 252. The control system monitors the capacitive signal generated and recorded by the proximity sensor circuit 304 for step 606, again evaluating whether the fluid transfer probe 860 is in contact or not in contact with the magnetic sled 252.

At the step 608 the system evaluates the three signals recorded at steps 602, 604, and 606. If step 602 returns a no contact signal, step 604 returns a contact signal, and step 606 returns a no contact signal, this indicates that the tip stripping sequence has been successful. If any one these evaluations registers a signal that is the opposite of what it should be, then the control sequence moves to step 610, which changes the status of the magnetic separation wash station ("MW") 800 to a fatal error (e.g., out of service, channel out of service, invalidate tube (e.g., receptacle vessel), or invalidate MRD). If the evaluation of the signals at step 608 register as expected, then the control sequence moves to step 612. At step 612, the fluid transfer probes 860 are moved to an aspirate position above the magnet sled. At step 614 the magnetic sled 252 is moved to its retracted, or home, position, as verified by the retracted position sensor 296. At step 616, the control system checks the step count of magnet sled drive motor 284 in moving the sled 252 to the home position to ensure that the sled 252 moved the correct distance and was, in fact, in the correct, tip stripping position, during the tip stripping procedure. If the number of steps was correct, then the tip stripping cycle is completed and concludes. If not, then, at step 618, the control system evaluates whether or not a tip strip retry should be attempted. The control system is programmed to retry tip stripping a specified number of times N, where N is a configurable value. If the query regarding retry registers as no, i.e., N retries have been attempted, then the control sequence moves to step 610 and registers a magnetic separation wash station fatal error. If the retry registers a yes, the control sequence proceeds to step 620. Step 620 instructs the magnetic sled to move to its stripping position and restarts the cycle for tip stripping back at step 602.

The system 300 shown in FIG. 16 is also configured to perform capacitive liquid level sensing. The fundamental concept is to leverage the fact that system capacitance will change dramatically as the fluid transfer probe 860 with tip 170 attached is moved through a fluid sensing range 316 from a position above the fluid level within the receptacle 162 to a position below the fluid level. As the fluid transfer probe 860 moves through the fluid sensing range 316, the capacitive signal (in mV) is measured and plotted against encoder counts of the lift motor 868 (which reflects vertical position of the probe 860).

Figure 22A:
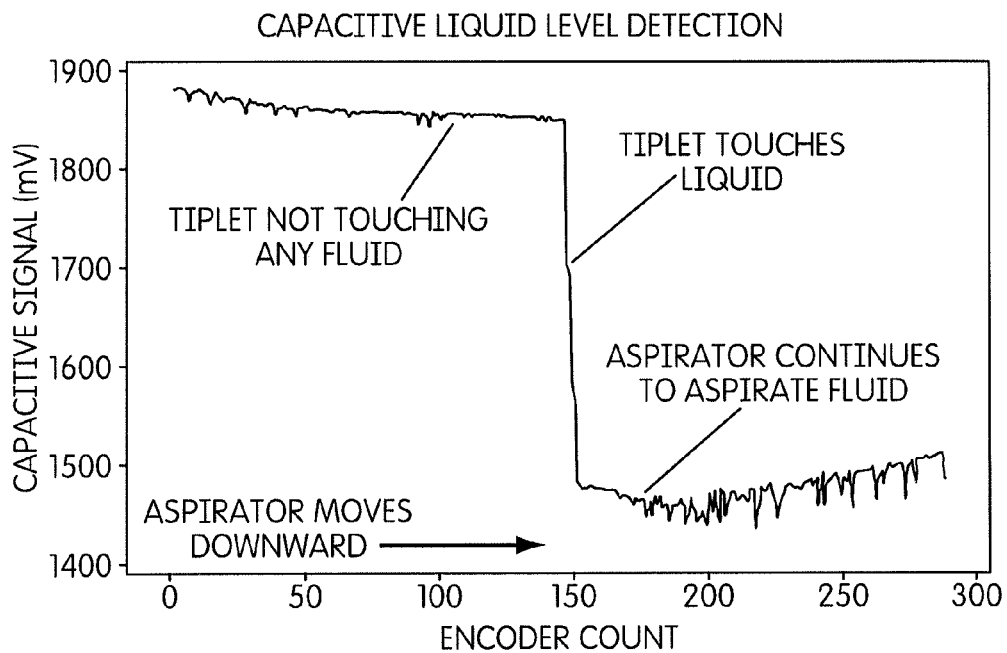
FIG. 22A is a graph of the waveform showing capacitive signal from a fluid transfer probe, during a period of time where the probe with a protective conduit attached contacts a fluid dielectric resulting in a rapid change in capacitive signal.

The waveform that is measured and evaluated to determine whether or not a fluid transfer probe 860 has contacted fluid in a receptacle is referred to herein as "the β-waveform." An example of such a waveform is shown in FIG. 22A, which shows the digitized level sense signal for one fluid transfer probe 860 and tip 170. The voltage signal decreases as capacitance increases. The X-axis of the graph, in units of encoder counts, represents the steps of the lift motor 868 and corresponds to the Z-axis position of the fluid transfer probe 860 as it descends to within the receptacle. Representative signals generated by the fluid sensing capability of the system 300, such as the one shown in FIG. 22A, are used to determine when the fluid transfer probe 860 and tip 170 make contact with the fluid contents of a reaction receptacle 162.

As the fluid transfer probe 860 touches liquid, which is a different dielectric than air, an almost instantaneous change in capacitance occurs because there is an instantaneous change in the coupling of the tip 170 to the surrounding environment. The capacitance, measured as the β-waveform, jumps up (causing the measured voltage signal to drop) when the fluid transfer probe 860 makes the transition from just above to just below liquid. This is clearly illustrated in FIG. 22A. As the probe 860 moves downwardly, the capacitive signal is relatively constant at between 1800 mV and 1900 mV. Then, at an encoder count of about 150—representing downward movement of the probe 860—the capacitive signal drops almost instantaneously to below 1500 mV, indicating a sudden increase in capacitance due to the probe 860 (and the capacitive tip 170 secured thereto) contacting the fluid level.

The signal processing circuitry of proximity sensor circuit 304 is configured to detect rapid changes in the signal. A rapid change of capacitive signal that is greater than a threshold value is considered an event where the tip 170 contacts the fluid level. For example, in the data shown in FIG. 22A, the amplitude is relatively constant prior to and after fluid surface contact, but, at the instance of fluid surface contact, the amplitude drops by about 300 to 400 mV (or more) nearly instantaneously (in less than 10 encoder counts in the illustrated data). In an embodiment in which the threshold value is based on data such as that shown in FIG. 22A, such a threshold could be predefined as a change in amplitude of between 200 and 350 mV that occurs in 10 or less encoder counts.

The processing of the β-waveform may be done by an encoder which includes an analog circuit which forms a high pass filter into a comparator, wherein the high pass filter passes only fast changes and the comparator tests the amplitude of the change against a threshold value. Alternatively, the processing may be done by digitizing the analog signal and implementing the high pass filter as a digital signal-processing algorithm in the encoder. The output of the digital filter is compared to a pre-determined threshold that establishes when fluid is sensed.

Figure 22B:
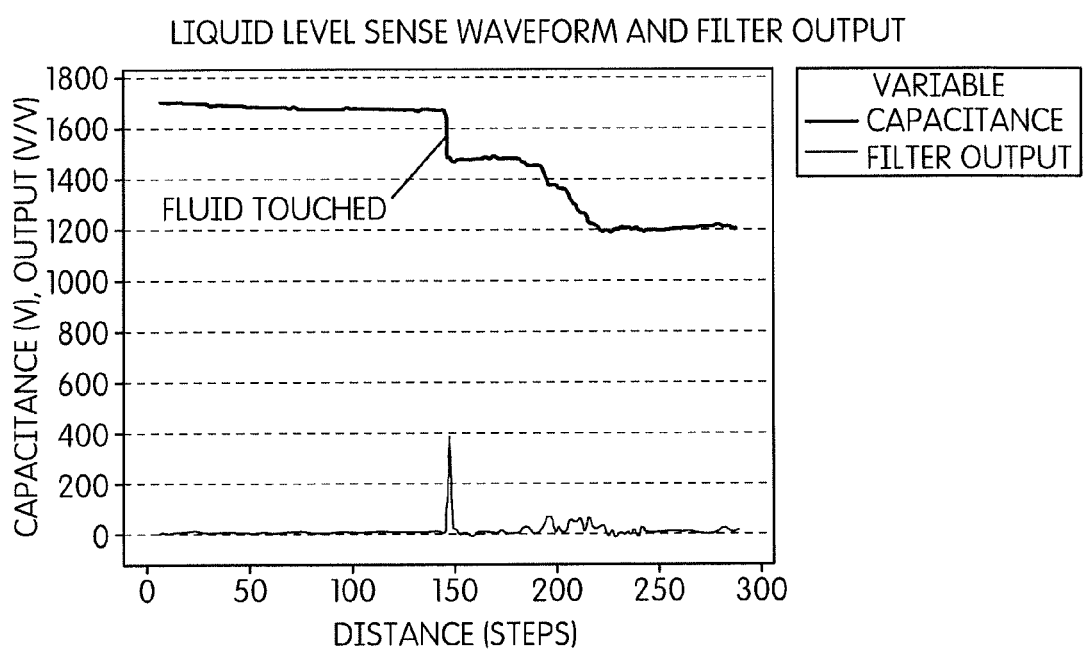
FIG. 22B is a graph of the waveform showing capacitive signal from a fluid transfer probe, during a period of time where the probe with a protective conduit attached contacts a fluid dielectric resulting in a rapid change in capacitive signal, plotted alongside the derivative of that waveform.

In an embodiment of the invention, the fluid-sensing threshold is determined according to rapid changes in the slope of the β-waveform signal. As shown by example in FIG. 22B, both the capacitance signal of a probe 860, represented by the upper trace, and the derivative of the capacitance signal, represented by the lower trace and referred to as the filter output, are measured against the distance, i.e., the number of steps as tracked by the encoder 825, that the fluid transfer probe 860 and tip 170 are moved by the lift motor 868. The filter operates as an edge detector; the value of the lower trace is typically near zero, but when contact with the edge of fluid occurs, there is a spike in the value of the filter. FIG. 22B further shows changes in capacitance after the fast transition caused by a fluid transfer probe 860 coming into contact with fluid. These later variations in capacitance are smaller in magnitude and are caused in part by the fluid moving through the fluid transfer probe 860 and fluid transfer tubing 864. The filter also rejects the slower change in capacitance after the fluid transfer probe 860 and tip 170 make contact with the fluid.

Based on the filter signal, a threshold may be set such that when the output of the filter crosses the specific threshold value, the system will indicate that fluid has been detected. For example, in an embodiment in which the threshold is based on data such as that shown in FIG. 22B, in which the slope (filter output) is approximately zero prior to and after fluid surface contact, but jumps to nearly 400 mV at the instance of fluid surface contact, such a threshold slope could be a value between 200 and 400 mV. A threshold value for general use by fluid transfer probes 860 may be determined and calibrated by performing liquid level detections with fluid transfer probes 860 across several magnetic separation wash stations 800 and measuring the mean and standard deviation of the amplitude of the maximum value of the output of the filter. The threshold value may be set relative to the measured maximum amplitude values of the filter signal.

As shown in FIG. 23A, the fluid level detection process of an embodiment of the invention comprises movement of the fluid transfer probe 860—with a tip 170 attached thereto—to a number of specified Z-axis positions, known as reference levels, within each reaction receptacle 162 of an MRD 160. These reference levels are referred to as "fluid sense positions" ("FSP") which the control system uses to determine when the fluid in the receptacle (e.g., receptacle vessel 162) is too high or too low, thus indicating an error in dispensing and/or aspirating.

Each of the fluid sense positions may be altered to account for differences in device construction or assay chemistry. The following heights and volumes of fluid for each fluid sense position in the receptacle are exemplary. Fluid sense position A 330 corresponds to a volume of approximately 2500 µL, in the receptacle. Fluid sense position B 334 corresponds to a volume of approximately 1500 µL, in the receptacle. Fluid sense position C 332 corresponds to a volume of approximately 1800 µL, in the receptacle. Fluid sense position D 338 corresponds to a volume of approximately 820 µL, in the receptacle. Fluid sense position E 336 corresponds to a volume of approximately 1000 µL, in the receptacle. The position just above the bottom of the receptacle, as indicated by position 340, corresponds to no volume of fluid remaining in the receptacle. In other words, for a receptacle of known geometry and dimensions, the FSP corresponds to a known volume of fluid within the receptacle. Generally, the system checks for fluid in an incremental manner, where the distance of a distinct movement is shorter than the length of the tip 170, so that if the fluid transfer is not occurring the tip 170 does not become completely submerged and the fluid transfer probe 860 will not become contaminated by fluid within the receptacle contacting the exterior of the fluid transfer probe. In one embodiment the control system includes repeat checks starting at the 2500 µL, fluid level and at the 1800 µL, fluid levels in order to distinguish between an errantly high fluid level caused by either a faulty fluid pump or a clogged fluid transfer probe 860. In the case of a faulty fluid pump the control system would recognize the presence of fluid at a higher than expected level, however the fluid transfer probe 860 would remove much of the excess fluid during the course of the check. The repeat check would therefore detect no fluid. By contrast in the case of a clogged fluid transfer probe 860, both the initial and repeat check would recognize the presence of fluid at a higher than expected level.

EXAMPLE

FIG. 23B is a flowchart that describes an exemplary process for detecting fluid level and verifying fluid volume in a receptacle vessel 162 during a magnetic separation wash cycle. In describing the process shown by FIG. 23B, it is assumed that the fluid transfer probe 860 has successfully engaged a partially conductive tip 170 which is secured to the distal end of the probe 860 by a frictional, interference fit. FIG. 23B describes a series of fluid levels optimized for operation with a fluid transfer probe tip 170 with a length equivalent to the cylinder height of approximately 1200 µL, of fluid in the MRD 160 receptacle vessel 162, and for operation with an expected fluid level of approximately 1000 µL which has shown to be optimal for current employed assays. Alternatively, the fluid levels may be changed to optimize for operation with a different geometry MRD 160 or tip 170, or a different expected fluid level.

Beginning at step 402, "Move 1" comprises activation of the lift motor 868 an appropriate number of steps to position the fluid transfer probe 860 and tip 170 at "Level 1" which corresponds to fluid sense position A 330 in FIG. 23A. Step 402 starts the move and starts the collection of the β-waveform during the move. The air to fluid transition can happen at any time for the fluid transfer probe 860, and the controller 825 monitors the motor step, i.e. Z-axis position, at which the air-to-fluid transition occurs. At step 404, to check for an over-dispense, the capacitive signal of each fluid transfer probe 860 and tip 170 is evaluated at fluid sense position A 330 to determine if there is fluid at that height in any receptacle vessel 162 (referred to as "tube" in FIG. 23B). The evaluation is effectively whether the β-waveform measured is similar to the waveform shown in FIG. 22, which indicates liquid surface contact which causes a jump in capacitance, resulting in a drop in the capacitive signal voltage. If fluid level is detected at fluid sense position A 330, or higher, then the sequence proceeds to step 406, wherein the MRD 160 being processed is invalidated, the magnetic separation wash station ("MW") 800 is taken out of service, and the magnetic separation wash sequence is ended. Detection of fluid at fluid sense position A 330 indicates that there is sufficient fluid in the receptacle vessel 162 to have caused spillage and contamination of the magnetic separation system during a previous step where the MRD 160 is subjected to high-speed orbital mixing. Thus, detection of fluid at fluid sense position A 330 indicates an over-dispense error which merits taking the magnetic separation wash station 800 out of service.

If no fluid is contacted at fluid sense position A 330 by the fluid transfer probe 860, then the fluid sense sequence proceeds to step 408, wherein "Move 2" positions the fluid transfer probe 860 at "Level 2" which corresponds to fluid sense position B 334 in FIG. 23A. To check for an over-dispense, at step 410, the capacitive signal of each fluid transfer probe 860 and tip 170 is evaluated at fluid sense position B 334 to determine if there is any fluid at that height in the receptacle vessel 162. Detection of fluid at fluid sense position B 334, when no fluid was detected at fluid sense position A 330, indicates that there was an over-dispense error, but that the tip 170 is not submerged. This allows the system to optionally take a single fluid transfer probe 860 channel out of service and continue processing with other channels in a magnetic wash separation station 800. If the fluid level is detected at fluid sense position B 334, or higher, in any receptacle vessel 162, the sequence proceeds to step 412 and checks a set processing parameter as to whether or not the magnetic separation wash station 800 should attempt to process the individual receptacle vessel 162. The set processing parameter may be implemented as a selectable mode of operation that can be turned on or off in the software controlling the analyzer. If the processing parameter is set to allow individual receptacle vessel processing, the sequence proceeds to step 416, wherein the single receptacle vessel 162, which is only one of five receptacle vessels 162 that comprise the MRD 160, is invalidated and the corresponding channel is taken out of service. If the processing parameter is set to not allow individual receptacle vessel processing, then the sequence proceeds to step 414, wherein the entire MRD 160 is invalidated and the magnetic separation wash station 800 is taken out of service.

After the magnetic separation wash station 800 either attempts to process the individual receptacle vessels, or not, as described by steps 412-416, or if in step 410 no fluid is detected at fluid sense position B 334, then the sequence proceeds to step 418. At step 418, "Move 3" positions the fluid transfer probe 860 and tip 170 at "Level 3" which corresponds to fluid sense position A 330 (i.e., the same position as "Level 1") in FIG. 23A. At step 420, the fluid transfer probe 860 and tip 170 dwell at fluid sense position A 330. The dwell duration is configurable and is preferably six seconds. The dwell period of step 420 allows the fluid being transferred to move completely through the fluid transfer probe 860 and the fluid transfer tubing 864. Dwell periods such as that at step 420 during the capacitive liquid level sensing process ensure that changes in capacitance caused by fluid moving through the system do not interfere with later fluid level detections.

Following the dwell at step 422, at step 424 "Move 4" positions the fluid transfer probe 860 and tip 170 at "Level 4" which corresponds to fluid sense position C 332 in FIG. 23A, while the control system again monitors the capacitive signal from the fluid transfer probe 860 and tip 170 to determine whether or not there is fluid at fluid sense position C 332. If fluid is detected at fluid sense position C 332, the sequence proceeds to step 426, and the MRD 160 is invalidated and the magnetic separation wash station 800 and is taken out of service. Generally, there should not be fluid at fluid sense position C 332, because at this point in the fluid sense cycle, the fluid transfer probe 860 has already descended to a lower height defined by fluid sense position B 334. As noted above, the fluid transfer probe 860 is coupled to a vacuum pump (not shown) and thereby aspirates fluid during its movements within the receptacle vessel 162. Thus any volume of fluid that was originally above a height corresponding to fluid sense position B 334 should already been removed from the receptacle vessel 162. If a fluid transfer probe 860 is partially clogged, then some fluid transfer may have occurred during the prior moves, but the intended volume of fluid may not have been completely transferred. Thus, in this embodiment of the invention, the system determines whether or not there is fluid at fluid sense position C 332, even though the fluid transfer probe 860 has already descended to a point lower in the receptacle vessel 162 during the process, in order to ascertain if only partial fluid transfer is being performed.

If no fluid is detected at fluid sense position C 332 during step 424, the sequence proceeds to step 428, wherein "Move 5" positions the fluid transfer probe 860 and tip 170 at "Level 5" which corresponds to fluid sense position D 338 in FIG. 23A. Next, at step 430, the control system again determines whether or not there is fluid in any receptacle vessel at fluid sense position D 338. If no fluid is detected at fluid sense position D 338, the sequence proceeds to step 432 and checks the set processing parameter, which is the same parameter as used by step 412, as to whether or not the magnetic separation wash station 800 should attempt to process the individual receptacle vessel 162. If the processing parameter is set to allow individual receptacle vessel processing, the sequence proceeds to step 436 wherein the single receptacle vessel 162 is invalidated and the corresponding channel is taken out of service. If the processing parameter is set to not allow individual receptacle vessel processing, then the sequence proceeds to step 434 wherein the entire MRD 160 is invalidated and the magnetic separation wash station 800 is taken out of service.

After the control system either attempts to process the individual receptacle vessels, or not, as described by steps 432-436, or if fluid is detected at fluid sense position D 338 during step 430, the sequence proceeds to step 438, wherein "Move 6" positions the fluid transfer probe 860 and tip 170 at "Level 6" corresponding to fluid sense position C 332 (i.e., the same position as "Level 4") in FIG. 23A. At step 440, the fluid transfer probe 860 and tip 170 dwell at fluid sense position C 332, wherein the dwell duration is configurable and preferably six seconds. Following the dwell at step 440, the fluid wash sequence proceeds to step 442, wherein "Move 7" positions the fluid transfer probe 860 and tip 170 at "Level 7" which corresponds to fluid sense position E 336 in FIG. 23A. At step 444, the control system determines whether or not there is fluid at fluid sense position E 336. If fluid is detected at fluid sense position E 336, then the fluid wash sequence proceeds to step 446 wherein the MRD 160 is invalidated and the magnetic separation wash station 800 is taken out-of-service. If no fluid is detected at fluid sense position E 336, then the fluid wash sequence proceeds to step 448 wherein the fluid transfer probe 860 and tip 170 move to the bottom of the receptacle vessel 162 as indicated by position 340 in FIG. 23A.

At step 450, the fluid transfer probe 860 and tip 170 dwell at position 340 at the bottom of the receptacle vessel 162. The dwell duration is configurable and is preferably six seconds. The purpose of this dwell period is to allow all fluid in the receptacle vessel 162 to be transferred by letting fluid transfer probes 860 to remain at the bottom of the receptacle vessel 162, i.e. at position 340. Even though the bulk of the fluid may be transferred by this point in the fluid transfer process, some fluid may remain on the walls of the receptacle vessel 162 and drip down to the bottom of the receptacle vessel 162 during this dwell period. The duration of this dwell must be long enough to ensure that all fluid is transferred regardless of the strength of the vacuum drawing flow through the fluid transfer probes 860 and fluid transfer tubing 864, yet short enough to prevent the associated airflow from drying out the remaining magnetic beads in the receptacle vessel 162.

Subsequently at step 452, the fluid transfer probe 860 and tip 170 move back to "Level 7" corresponding to fluid sense position E 336. This is the end of a fluid wash sequence. The fluid transfer probe 860 and tip 170 withdraw from the receptacle vessel 162 after this point, and would proceed to a tip stripping process as described above. The fluid wash cycle may be repeated again for an MRD 160 as the magnetic separation wash cycle continues, or the MRD may be removed from the magnetic separation wash station 800, and the fluid wash cycle will begin again for a subsequent MRD 160.

Hardware and Software

Aspects of the invention are implemented via control and computing hardware components, user-created software, data input components, and data output components. Hardware components include computing and control modules, such as microprocessors and computers, configured to effect computational and/or control steps by receiving one or more input values, executing one or more algorithms stored on non-transitory machine-readable media (e.g., software) that provide instruction for manipulating or otherwise acting on the input values, and output one or more output values. Such outputs may be displayed or otherwise indicated to a user for providing information to the user, for example information as to the status of the instrument or a process being performed thereby, or such outputs may comprise inputs to other processes and/or control algorithms. Data input components comprise elements by which data is input for use by the control and computing hardware components. Such data inputs may comprise positions sensors, motor encoders, and the proximity sensor circuit 304, as well as manual input elements, such as key boards, touch screens, microphones, switches, manually-operated scanners, etc. Data output components may comprises hard drives or other storage media, monitors, printers, indicator lights, or audible signal elements (e.g., buzzer, horn, bell, etc).

Software comprises instructions stored on non-transitory computer-readable media which, when executed by the control and computing hardware, cause the control and computing hardware to perform one or more automated or semi-automated processes.

Such software may comprise an algorithm with instructions for performing a tip present check following a tip engagement procedure. The tip present check algorithm receives inputs, such as, one or more fluid transfer probe positions, for example, input signals from the Z-axis sensors 829, 827 and/or encoder counts of the lift motor 868, capacitive signals ($\alpha$-waveforms) generated and recorded by the proximity sensor circuit 304, and one or more predetermined reference values, as may be input by a user or hard-encoded into the software. The algorithm then compares a characteristic of the $\alpha$-waveform, such as rate of change (slope) or amplitude, to the predetermined reference value(s), and outputs an indication that a tip is or is not attached to the distal end of the fluid transfer probe. If the comparison indicates a normal operation, i.e., a tip that should be present is present or a tip is absent when there should be no tip on the fluid transfer probe, the algorithm may not provide an explicit "indication" of normal operation, but may simply enable continued operation of the instrument controlled by the tip present check algorithm.

A specific tip present check algorithm is represented schematically by the flow chart at FIG. 20.

Such software may also comprise an algorithm with instructions for performing a tip absent check following a tip removal procedure. The tip absent check algorithm receives inputs, such as, one or more fluid transfer probe positions, for example, input signals from the Z-axis sensors 829, 827 and/or encoder counts of the lift motor 868, capacitive signals (α-waveforms) generated and recorded by the proximity sensor circuit 304, and one or more positions of the tip removal structure, such as input signals from the sensors 296, 298 and/or encoder counts of the drive motor 286, which indicate the position of the magnetic sled 252. Optionally, the algorithm may receive one or more predetermined reference values as may be input by a user or hard-encoded into the software. The algorithm monitors the α-waveform to determine if it is saturated when the tip removal structure is brought into contact with the fluid transfer probe and the protective tip and to determine if the α-waveform remains saturated after the tip removal procedure—which would indicate a failed removal—and outputs an indication that a tip is or is not attached to the distal end of the fluid transfer probe. If the comparison indicates a normal operation, i.e., a no tip is present, the algorithm may not provide an explicit "indication" of normal operation, but may simply enable continued operation of the instrument controlled by the tip absent check algorithm.

A specific tip present check algorithm is represented schematically by the flow chart at FIG. 21.

Such software may comprise an algorithm with instructions for performing a fluid level sense. The fluid level sense algorithm receives inputs, such as, one or more fluid transfer probe positions, for example, from input signals from the Z-axis sensors 829, 827 and/or encoder counts of the lift motor 868, capacitive signals (α-waveforms) generated and recorded by the proximity sensor circuit 304, and one or more predetermined reference values, as may be input by a user or hard-encoded into the software. The algorithm then compares a characteristic of the α-waveform, such as rate of change (slope) or amplitude, to the predetermined reference value(s), and, if the fluid transfer probe contacts a fluid surface, outputs a data signal indicating that the fluid transfer probe has contacted the fluid surface.

A specific tip present check algorithm is represented schematically by the flow chart at FIG. 23B.

While the present invention has been described and shown in considerable detail with reference to certain illustrative embodiments, including various combinations and sub-combinations of features, those skilled in the art will readily appreciate other embodiments and variations and modifications thereof as encompassed within the scope of the present invention. Moreover, the descriptions of such embodiments, combinations, and sub-combinations is not intended to convey that the inventions requires features or combinations of features other than those expressly recited in the claims. Accordingly, the present invention is deemed to include all modifications and variations encompassed within the spirit and scope of the following appended claims.

The invention claimed is:

1. A method for monitoring the status of a fluid transfer probe, the method comprising:
    (A) moving a fluid transfer probe known to have a protective tip on its distal end with respect to a secondary structure;
    (B) during step (A), measuring a first capacitance reference signal from the fluid transfer probe with the protective tip disposed on its distal end;
    (C) moving a fluid transfer probe known to lack a protective tip on its distal end with respect to the secondary structure;
    (D) during step (B), measuring a second capacitance reference signal from the fluid transfer probe lacking a protective tip;
    (E) deriving a reference value from either or both of the first capacitance reference signal and the second capacitance reference signal; and
    (F) determining whether or not a fluid transfer probe has a protective tip engaged on its distal end by:
        (1) moving the fluid transfer probe with respect to the secondary structure,
        (2) measuring a capacitance signal from the fluid transfer probe as the fluid transfer probe is moved with respect to the secondary structure, and
        (3) comparing at least one characteristic of the measured capacitance signal with the reference value.

2. The method of claim 1, wherein the reference value comprises a value between a mean of the first capacitance reference signal and a mean of the second capacitance reference signal.

3. The method of claim 1, wherein the amplitude of the measured signal from the fluid transfer probe is based on the capacitance between the fluid transfer probe and the secondary structure, and wherein the capacitance between the fluid transfer probe and the secondary structure depends on whether a protective tip is disposed on the fluid transfer probe.

4. The method of claim 1, further comprising detecting when the fluid transfer probe contacts a fluid surface within a receptacle by:
    lowering the fluid transfer probe with a protective tip disposed thereon into the receptacle;
    while lowering the fluid transfer probe into the receptacle, measuring a capacitance signal from the fluid transfer probe; and
    detecting a change in a characteristic of the signal exceeding a threshold value by comparing a value of the characteristic with the threshold value to indicate that the protective tip on the fluid transfer probe has contacted the fluid surface.

5. The method of claim 4, wherein the threshold value comprises a predetermined change in amplitude occurring within a predetermined movement distance of the fluid transfer probe, and detecting a change in a characteristic of the capacitance signal comprises comparing the amplitude of the capacitance signal during movement of the fluid transfer probe into the receptacle with the threshold value.

6. The method of claim 4, wherein the threshold value comprises a predetermined rate of change in amplitude, and detecting a change in a characteristic of the capacitance signal comprises comparing the rate of change of the amplitude of the capacitance signal during movement of the fluid transfer probe into the receptacle with the threshold value.

7. The method of claim 1, wherein comparing at least one characteristic of the measured capacitance signal with the reference value comprises comparing the amplitude of the measured capacitance signal with a reference amplitude, wherein the reference amplitude is derived from an amplitude of the first capacitance reference signal and an amplitude of the second capacitance reference signal.

8. The method of claim 1, wherein comparing at least one characteristic of the measured capacitance signal with the reference value comprises comparing a rate of change of the measured capacitance signal with a reference rate, wherein the reference rate is derived from a rate of change of the capacitance first reference signal and a rate of change of the second capacitance reference signal.

9. The method of claim 8, wherein the reference rate is derived by:
    determining a mean rate of change of the first capacitance reference signal;

determining a mean rate of change of the second capacitance reference signal; and setting as the reference rate a value between the mean rate of change of the first capacitance reference signal and the mean rate of change of the second capacitance reference signal.

10. A method for monitoring the status of a fluid transfer probe, the method comprising:
(A) moving the fluid transfer probe with respect to a secondary structure;
(B) while moving the fluid transfer probe with respect to the secondary structure, measuring a first signal related to capacitance of a group of components including the fluid transfer probe; and
(C) determining if a protective tip is disposed on the fluid transfer probe based on the first signal.

11. The method of claim 10, wherein step (C) comprises comparing at least one of:
(1) the amplitude of the first signal with a capacitance reference amplitude, wherein the capacitance reference amplitude is derived from (a) a first capacitance reference signal measured from a fluid transfer probe with a protective tip on its distal end as the fluid transfer probe and protective tip are moved with respect to the secondary structure and (b) a second capacitance reference signal measured from a fluid transfer probe lacking a protective tip on its distal end as the fluid transfer probe is moved with respect to the secondary structure, and
(2) the amount of variation of the first signal with a capacitance reference variation, wherein the capacitance reference variation is derived from the first capacitance reference signal and the second capacitance reference signal.

12. The method of claim 10, further comprising the steps of:
(D) lowering the fluid transfer probe with a protective tip disposed thereon into a receptacle;
(E) while lowering the fluid transfer probe into the receptacle, measuring a second signal related to the capacitance of a group of components including the fluid transfer probe; and
(F) detecting if the protective tip disposed on the fluid transfer probe has contacted a fluid surface within the receptacle based on the second signal.

13. The method of claim 12, wherein step (F) comprises detecting at least one of: (1) a change in the amplitude of the second signal exceeding a predefined threshold or (2) a change in the rate of change in the amplitude of the second signal exceeding a predefined threshold, to indicate that the fluid transfer probe has contacted a fluid surface.

14. The method of claim 10, wherein:
step (A) comprises moving two or more fluid transfer probes simultaneously with respect to the secondary structure;
step (B) comprises, for each fluid transfer probe moved in accordance with step (A), measuring a first signal related to capacitance of a group of components including that fluid transfer probe as the fluid transfer probes are moved with respect to the secondary structure; and
step (C) comprises determining if a protective tip is disposed on each fluid transfer probe based on the first signal measured for that fluid transfer probe.

15. The method of claim 12, wherein:
step (A) comprises moving two or more fluid transfer probes simultaneously with respect to the secondary structure;

step (B) comprises, for each fluid transfer probe moved in accordance with step (A), measuring a first signal related to capacitance of a group of components including that fluid transfer probe as the fluid transfer probes are moved with respect to the secondary structure;
step (C) comprises determining if a protective tip is disposed on each fluid transfer probe based on the first signal measured for that fluid transfer probe;
step (D) comprises lowering each of the two or more fluid transfer probes simultaneously into a receptacle,
step (E) comprises, for each fluid transfer probe, while lowering the fluid transfer probes into the receptacle, measuring a second signal related to capacitance of a group of components including that fluid transfer probe; and
step (F) comprises detecting if each fluid transfer probe has contacted a fluid surface within the receptacle based on the second signal measured for that fluid transfer probe.

16. The method of claim 10, wherein steps (A) and (B) are performed two or more times before step (C) is performed.

17. The method of claim 16, wherein the signals measured while performing steps (A) and (B) two or more times are averaged before step (C) is performed, and step (C) comprises determining if a protective tip is disposed on the fluid transfer probe based on an average first signal.

18. The method of claim 16, wherein steps (A) and (B) are performed three times before step (C) is performed.

19. The method of claim 12, further comprising monitoring the position of the fluid transfer probe during step (E) to determine an amount of fluid contained within the receptacle when contact with the fluid surface is detected according to step (F).

20. The method of claim 10, wherein step (A) comprises moving the fluid transfer probe one or more times between a first position with respect to the secondary structure and a second position with respect to the secondary structure.

21. The method of claim 20, wherein step (C) comprises subtracting the first signal measured at the first position with respect to the secondary structure and the first signal measured at the second position with respect to the secondary structure and comparing the difference to a predetermined threshold.

22. The method of claim 10, wherein step (C) comprises determining the slope of the first signal and comparing the slope of the first signal to a predetermined threshold.

23. The method of claim 22, wherein determining the predetermined threshold comprises:
(A) moving a fluid transfer probe known to have a protective tip on its distal end with respect to the secondary structure, and, while moving the fluid transfer probe and protective tip with respect to the secondary structure, measuring a first capacitance reference signal related to capacitance of the fluid transfer probe and protective tip;
(B) moving a fluid transfer probe known to lack a protective tip on its distal end with respect to the secondary structure, and, while moving the fluid transfer probe with respect to the secondary structure, measuring a second capacitance reference signal related to capacitance of the fluid transfer probe;
(C) determining a mean slope of the first capacitance reference signal;
(D) determining a mean slope of the second capacitance reference signal; and
(E) setting as the threshold a value between the mean slope of the first capacitance reference signal and the mean slope of the second capacitance reference signal.

24. A fluid transfer system comprising:
- a fluid transfer probe configured to aspirate fluid from a receptacle and/or dispense fluid into a receptacle;
- a probe control module constructed and arranged to enable the probe to engage a protective tip at a distal end of said fluid transfer probe; and
- a tip detection system configured to determine if a fluid transfer probe has a protective tip engaged on its distal end by:
  - (1) measuring a signal related to capacitance of a group of components including the fluid transfer probe as the fluid transfer probe is moved with respect to a secondary structure, and
  - (2) determining if a protective tip is engaged on the fluid transfer probe based on the measured signal.

25. The fluid transfer system of claim 24, further comprising a liquid level detection system configured to detect if said fluid transfer probe has contacted a fluid surface within a receptacle by measuring a second signal related to capacitance of a group of components including said fluid transfer probe while said fluid transfer probe is being lowered into the receptacle and detecting if the protective tip engaged on said fluid transfer probe has contacted a fluid surface within the receptacle based on the second signal.

26. The fluid transfer system of claim 24, further comprising a protective tip removal structure configured to be engaged by said fluid transfer probe and to remove a protective tip from the fluid transfer probe, and wherein the probe control module is further constructed and arranged to cause said fluid transfer probe to move into engagement with said protective tip removal structure.

27. The fluid transfer system of claim 24, wherein said protective tip detection system comprises a proximity sensor circuit configured to propagate a signal to said fluid transfer probe.

28. The fluid transfer system of claim 27, wherein said proximity sensor circuit comprises an electric field imaging device.

29. The fluid transfer system of claim 27, wherein said proximity sensor circuit is configured to propagate a sine wave signal to said fluid transfer probe.

30. The fluid transfer system of claim 24, wherein said probe control module comprises:
- a threaded drive screw;
- a threaded drive sleeve directly or indirectly connected to said fluid transfer probe and with which said drive screw is operatively coupled; and
- a motor operatively coupled to said drive screw and configured to effect powered rotation of said drive screw, whereby engagement between said drive screw and said drive sleeve converts rotation of said drive screw into translation of said fluid transfer probe.

31. The fluid transfer system of claim 24, wherein said secondary structure comprises a block with an opening formed therein, and wherein said fluid transfer probe extends into said opening when said fluid transfer probe is moved with respect to said secondary structure.

32. The fluid transfer probe of claim 31, wherein said opening comprises a hole formed through said block and said hole is formed to have two different diameters, and wherein the diameter of an upper portion of the hole is smaller than the diameter of a lower portion of the hole.

33. The fluid transfer system of claim 24, comprising two or more fluid transfer probes and wherein said tip detection system is configured to determine if each fluid transfer probe has a protective tip engaged on its distal end by:
- (1) for each fluid transfer probe, measuring a signal related to capacitance of a group of components including the fluid transfer probe as the fluid transfer probe is moved with respect to a secondary structure, and
- (2) determining if a protective tip is engaged on the fluid transfer probe based on the measured signal for that fluid transfer probe.

34. The fluid transfer system of claim 24, wherein said tip detection system is configured to determine if a fluid transfer probe has a protective tip engaged on its distal end by comparing at least one of:
- (1) the amplitude of the measured signal with a capacitance reference amplitude, wherein the capacitance reference amplitude is derived from (a) a first capacitance reference signal measured from a fluid transfer probe with a protective tip on its distal end as the fluid transfer probe and protective tip are moved with respect to the secondary structure and (b) a second capacitance reference signal measured from a fluid transfer probe lacking a protective tip on its distal end as the fluid transfer probe is moved with respect to the secondary structure, and
- (2) the amount of variation of the measured signal with a capacitance reference variation, wherein the capacitance reference variation is derived from the first capacitance reference signal and the second capacitance reference signal.

35. A method for transferring a fluid to and/or from a receptacle with a fluid transfer probe, said method comprising:
- (A) lowering the fluid transfer probe into engagement with a protective tip to removably secure the protective tip on a distal end of the fluid transfer probe:
- (B) confirming that the protective tip was successfully secured to the distal end of the fluid transfer probe during step (A) by:
  - (1) moving the fluid transfer probe with respect to a secondary structure;
  - (2) while moving the fluid transfer probe with respect to the secondary structure, measuring a first signal related to capacitance of a group of components including the fluid transfer probe; and
  - (3) confirming that the protective tip is secured to the fluid transfer probe based on the first signal,
- (C) after step (B), lowering the fluid transfer probe into the receptacle and withdrawing fluid from or dispensing fluid into the receptacle;
- (D) before, during, or after step (C), determining a level of fluid within the receptacle by:
  - (1) lowering the fluid transfer probe with the protective tip secured thereto into the receptacle;
  - (2) while lowering the fluid transfer probe into the receptacle, measuring a second signal related to the capacitance of a group of components including the fluid transfer probe; and
  - (3) detecting if the protective tip secured to the fluid transfer probe has contacted a fluid surface within the receptacle based on the second signal;
- (E) after step (D), moving the fluid transfer probe and protective tip into engagement with a tip removal structure and effecting a relative movement between the fluid transfer probe and the tip removal structure to remove the tip from the distal end of the fluid transfer probe; and
- (F) confirming that the protective tip was successfully removed from the distal end of the fluid transfer probe during step (E) by:

(1) measuring a third signal related to capacitance of a group of components including the fluid transfer probe; and
(2) confirming that the protective tip is absent from the fluid transfer probe based on the third signal.

36. The method of claim 35, wherein step (F) comprises:
moving the fluid transfer probe with respect to the secondary structure; and
measuring the third signal while the fluid transfer probe is moved with respect to the secondary structure.

37. The method of claim 35, wherein step (F) comprises measuring the third signal during step (E) to detect a change in the third signal that is indicative of the absence of the protective tip from the fluid transfer probe after effecting the relative movement between the fluid transfer probe and the tip removal structure.

38. The method of claim 37, wherein the tip removal structure comprises a plate having a keyhole-shaped opening formed therein, the keyhole-shaped opening having a first portion and a second portion, wherein the diameter of the first portion is larger than the diameter of the second portion, and wherein step (E) comprises:
moving the fluid transfer probe with the protective tip secured to the distal end thereof into the first portion of the keyhole-shaped opening;
effecting a lateral relative movement between the plate and the fluid transfer probe to move the fluid transfer probe into the second portion of the key-hole shaped opening, whereby at least one of the fluid transfer probe or the protective tip contacts the plate when the fluid transfer probe is moved into the second portion of the key-hole shaped opening thereby causing a detectable change in the measured third signal; and
moving the fluid transfer probe out of the keyhole-shaped opening,
wherein step (F) comprises determining from the third signal if the protective tip is still in contact with the plate after moving the fluid transfer probe out of the keyhole-shaped opening by a distance that is less than a length of the protective tip.

39. The method of claim 35, wherein step (B)(3) comprises comparing at least one of:
(1) the amplitude of the first signal with a reference amplitude, wherein the reference amplitude is derived from (a) a first reference signal measured from a fluid transfer probe with a protective tip on its distal end as the fluid transfer probe and protective tip are moved with respect to the secondary structure and (b) a second reference signal measured from a fluid transfer probe lacking a protective tip on its distal end as the fluid transfer probe is moved with respect to the secondary structure, and
(2) the amount of variation of the first signal with a reference variation, wherein the reference variation is derived from the first reference signal and the second reference signal.

40. The method of claim 35, wherein step (D)(3) comprises detecting at least one of: (1) a change in the amplitude of the second signal exceeding a predefined threshold or (2) a change in the rate of change in the amplitude of the second signal exceeding a predefined threshold, to indicate that the fluid transfer probe has contacted a fluid surface.

41. The method of claim 35, wherein steps (B)(1) and (B)(2) are performed two or more times before step (B)(3) is performed.

42. The method of claim 41, wherein the signals measured while performing steps (B)(1) and (B)(2) two or more times are averaged before step (B)(3) is performed, and step (B)(3) comprises determining if a protective tip is disposed on the fluid transfer probe based on an average first signal.

43. The method of claim 35, further comprising monitoring the position of the fluid transfer probe during step (D)(3) to determine an amount of fluid contained within the receptacle when contact with the fluid surface is detected according to step (D)(3).

44. The method of claim 35, wherein step (B)(1) comprises moving the fluid transfer probe one or more times between a first position with respect to the secondary structure and a second position with respect to the secondary structure.

45. The method of claim 44, wherein step (B)(3) comprises subtracting the first signal measured at the first position with respect to the secondary structure and the first signal measured at the second position with respect to the secondary structure and comparing the difference to a predetermined threshold.

46. The method of claim 35, wherein step (B)(3) comprises determining the slope of the first signal and comparing the slope of the first signal to a predetermined threshold.

47. The method of claim 46, wherein determining the predetermined threshold comprises:
(A) moving a fluid transfer probe known to have a protective tip on its distal end with respect to the secondary structure, and, while moving the fluid transfer probe and protective tip with respect to the secondary structure, measuring a first reference signal related to capacitance of the fluid transfer probe and protective tip;
(B) moving a fluid transfer probe known to lack a protective tip on its distal end with respect to the secondary structure, and, while moving the fluid transfer probe with respect to the secondary structure, measuring a second reference signal related to capacitance of the fluid transfer probe;
(C) determining a mean slope of the first reference signal;
(D) determining a mean slope of the second reference signal; and
(E) setting as the threshold a value between the mean slope of the first reference signal and the mean slope of the second reference signal.

* * * * *

UNITED STATES PATENT AND TRADEMARK OFFICE
CERTIFICATE OF CORRECTION

PATENT NO. : 9,046,507 B2  
APPLICATION NO. : 13/192828  
DATED : June 2, 2015  
INVENTOR(S) : Knight et al.

Page 1 of 1

It is certified that error appears in the above-identified patent and that said Letters Patent is hereby corrected as shown below:

In the Claims:

Claim 1, Col. 37, line 65: "(B)" should be -- (C) --

Signed and Sealed this
Twenty-second Day of March, 2016

Michelle K. Lee
*Director of the United States Patent and Trademark Office*